United States Patent
Ng et al.

(10) Patent No.: US 12,427,175 B2
(45) Date of Patent: Sep. 30, 2025

(54) FECAL FUNGOME AND THERAPEUTIC EFFICACY OF FECAL MICROBIOTA TRANSPLANTATION

(71) Applicant: The Chinese University of Hong Kong, New Territories (CN)

(72) Inventors: Siew Chien Ng, Hong Kong (CN); Tao Zuo, Qingzhou (CN); Ka Leung Francis Chan, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 128 days.

(21) Appl. No.: 18/090,413

(22) Filed: Dec. 28, 2022

(65) Prior Publication Data

US 2023/0321166 A1  Oct. 12, 2023

Related U.S. Application Data

(62) Division of application No. 16/966,853, filed as application No. PCT/CN2019/074353 on Feb. 1, 2019, now abandoned.

(60) Provisional application No. 62/679,417, filed on Jun. 1, 2018, provisional application No. 62/625,705, filed on Feb. 2, 2018.

(51) Int. Cl.
| | | |
|---|---|---|
| *A61K 36/064* | (2006.01) | |
| *A61P 1/12* | (2006.01) | |
| *C12N 1/16* | (2006.01) | |
| *C12N 1/20* | (2006.01) | |
| *C12R 1/725* | (2006.01) | |

(52) U.S. Cl.
CPC ............ *A61K 36/064* (2013.01); *A61P 1/12* (2018.01); *C12N 1/20* (2013.01); *C12N 1/165* (2021.05); *C12R 2001/725* (2021.05)

(58) Field of Classification Search
CPC .......... A61K 36/064; A61P 1/12; C12N 1/20; C12N 1/165; C12R 2001/725
See application file for complete search history.

(56) References Cited

FOREIGN PATENT DOCUMENTS

| CN | 104922158 A | 9/2015 |
|---|---|---|
| CN | 105451561 A | 3/2016 |
| WO | 2015/170979 A1 | 11/2015 |
| WO | 2017/060178 A1 | 4/2017 |
| WO | 2017/103550 A1 | 6/2017 |
| WO | 2017/210428 A1 | 12/2017 |

OTHER PUBLICATIONS

Allegretti. Jr., et al., "Restoring the gut microbiome for the treatment of inflammatory bowel diseases," World Journal of Gastroenterology, No. 13, vol. 20, pp. 3468-3474 (Apr. 7, 2014).
Oldfield, E.C, .et al. "Clinical update for the diagnosis and treatment of *Clostridium difficile* infection," World Journal of Gastrointestinal Pharmacology and Therapeutics, No. 1, vol. 5, pp. 1-26 (Feb. 6, 2014).
Rossen , N. G. e t al., "Fecal microbiota transplantation as novel therapy in gastroenterology: A systematic review," World Journal of Gastroenterology, No. 17 vol. 21, pp. 5359-5371 (May 7, 2015).
International Search Report and Written Opinion for PCT Application No. PCT/CN2019/074353, mailed Apr. 28, 2019, 9 pages.
Russo, et al., (Clinical Microbiology and Infection, vol. 21, pp. 493.e1-493.e4).
Conceição-neto, et al., (Gut 67.8 (2018): 1558-1559).

*Primary Examiner* — Robert A Zeman
(74) *Attorney, Agent, or Firm* — Kilpatrick Townsend & Stockton LLP

(57) ABSTRACT

The present invention resides in the discovery that altered abundance of fungal species in the gut and feces of both fecal microbiota transplantation (FMT) donors and recipients may influence the outcome of FMT treatment. Thus, novel methods are provided for identifying subjects as suitable donor or recipients for FMT, for assessing the likelihood of FMT treatment success, and for enhancing FMT treatment efficacy. Also provided are kits and compositions for FMT with enhanced efficacy.

15 Claims, 41 Drawing Sheets
Specification includes a Sequence Listing.

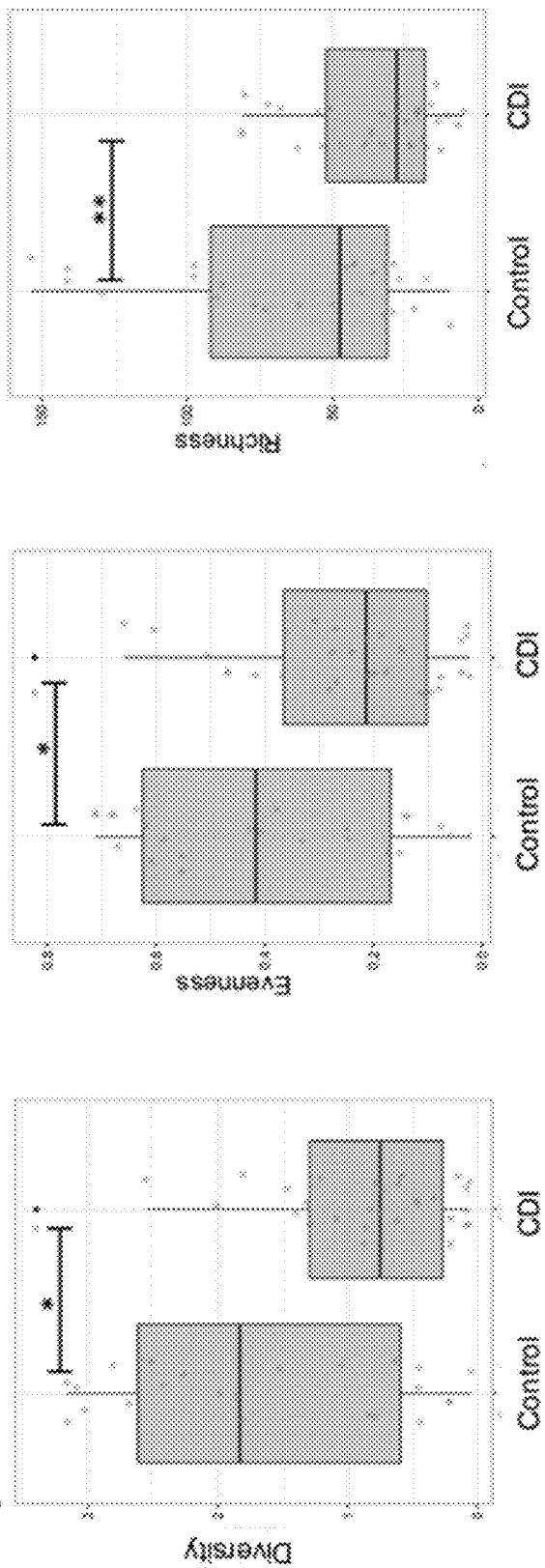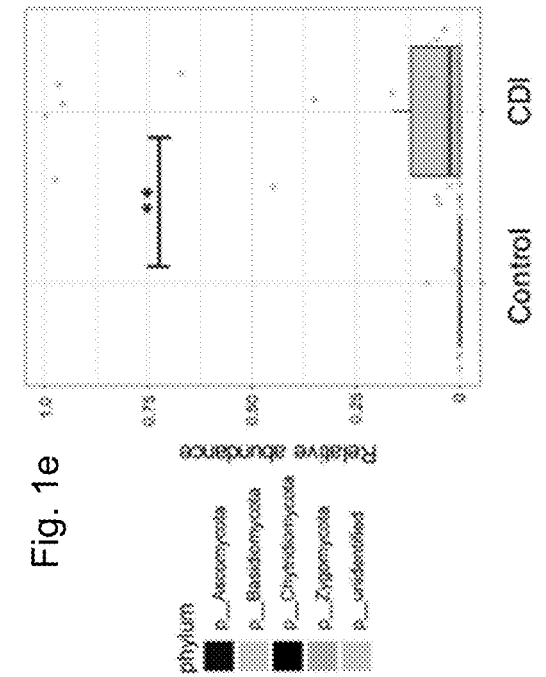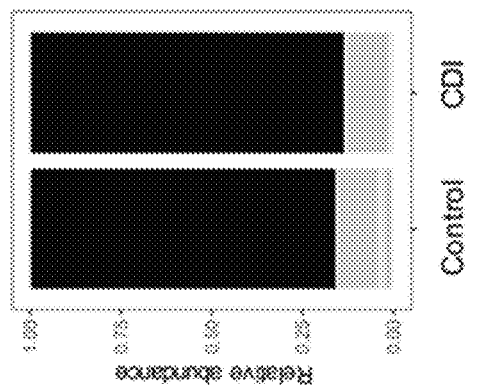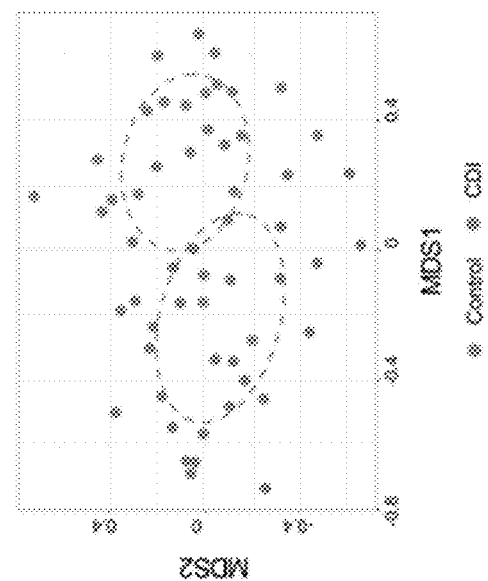

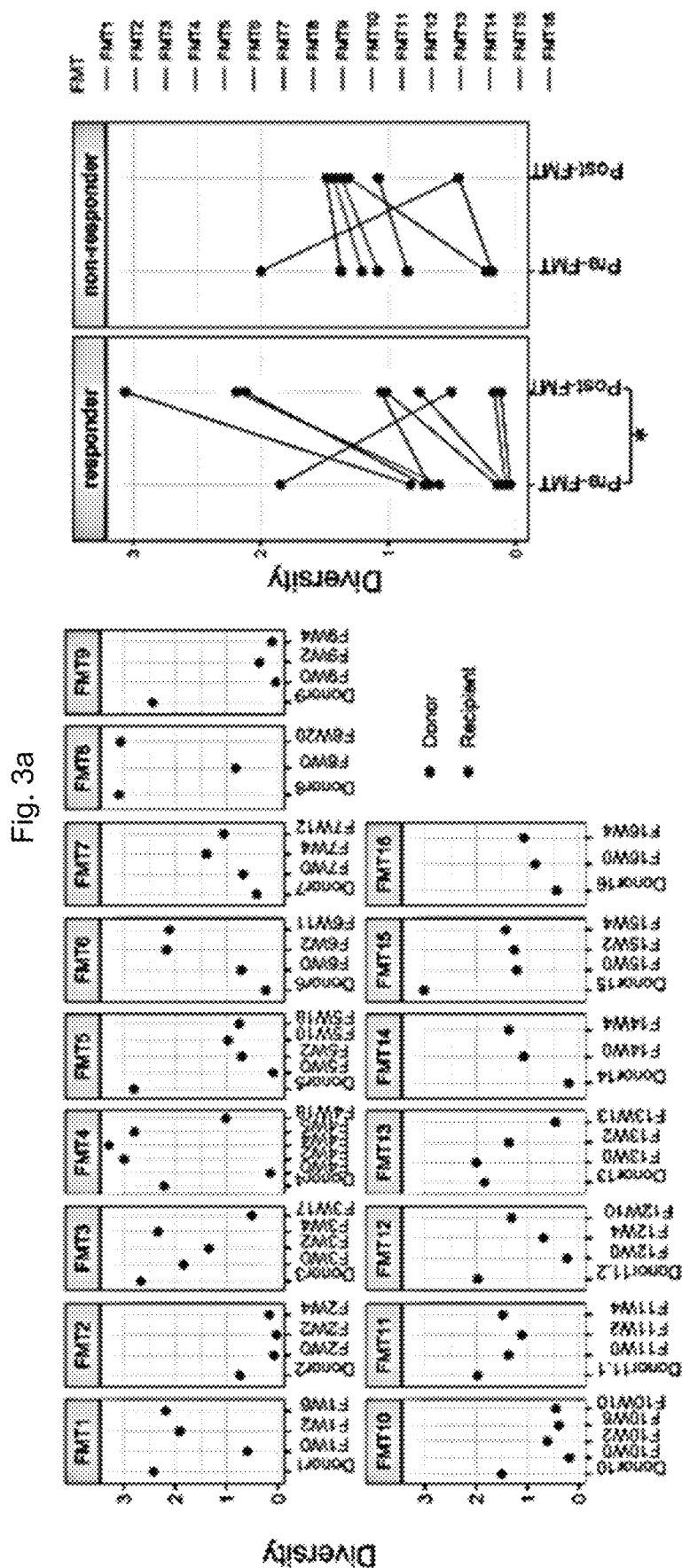

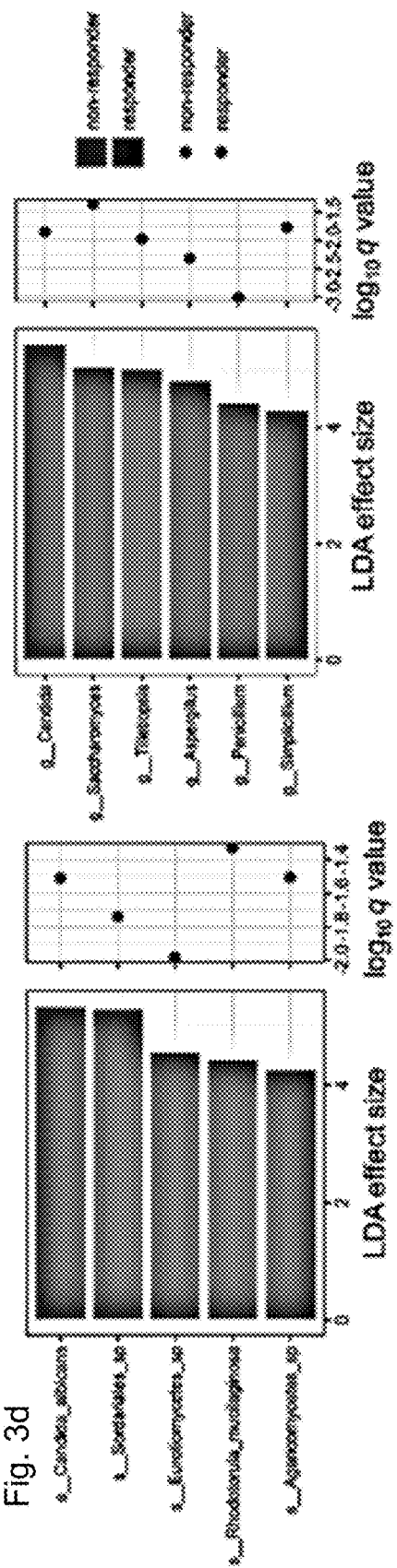
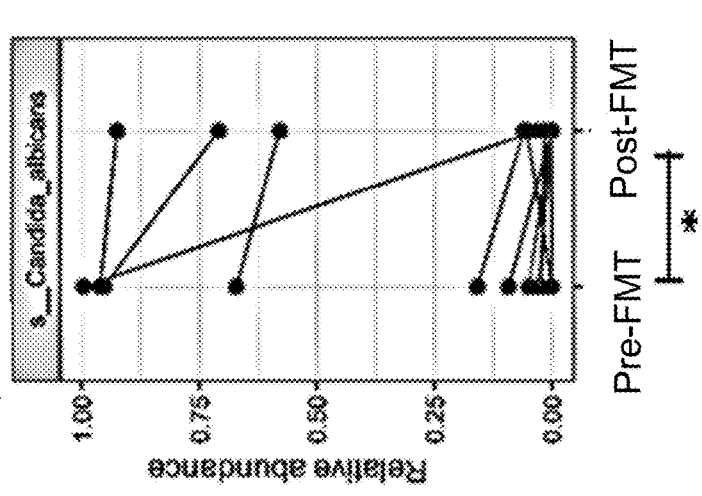
Fig. 3d
Fig. 3e
Fig. 3f
Fig. 3g

Fig. 6

Fig. 9c  Post-treatment alteration in fungal diversity

| | FMT | STD |
|---|---|---|
| Individuals increased in diversity | 13 | 3 |
| Individuals decreased in diversity | 3 | 5 |

Chi-square test: $p=0.032$*

Post-treatment alteration in fungal richness

| | FMT | STD |
|---|---|---|
| Individuals increased in richness | 11 | 3 |
| Individuals decreased in richness | 5 | 5 |

Chi-square test: $p=0.371$

```
SEQUENCE LISTING

Sequence total quantity: 7
SEQ ID NO: 1            moltype = DNA  length = 20
FEATURE                 Location/Qualifiers
misc_feature            1..20
                        note = Description of sequence: Primer: ITS2-F
source                  1..20
                        mol_type = other DNA
                        organism = synthetic construct
SEQUENCE: 1
gcatcgatga agaacgcagc                                                 20

SEQ ID NO: 2            moltype = DNA  length = 20
FEATURE                 Location/Qualifiers
misc_feature            1..20
                        note = Description of sequence: Primer: ITS2-R
source                  1..20
                        mol_type = other DNA
                        organism = synthetic construct
SEQUENCE: 2
tcctccgctt attgatatgc                                                 20

SEQ ID NO: 3            moltype = DNA  length = 21
FEATURE                 Location/Qualifiers
misc_feature            1..21
                        note = Description of sequence: Primer: C. albicans-F
source                  1..21
                        mol_type = other DNA
                        organism = Candida albicans
SEQUENCE: 3
cctgtttgag cgtcgtttct c                                               21

SEQ ID NO: 4            moltype = DNA  length = 25
FEATURE                 Location/Qualifiers
misc_feature            1..25
                        note = Description of sequence: Primer: C. albicans-R
source                  1..25
                        mol_type = other DNA
                        organism = Candida albicans
SEQUENCE: 4
tttggttaga cctaagccat tgtca                                           25

SEQ ID NO: 5            moltype = DNA  length = 20
```

```
FEATURE              Location/Qualifiers
misc_feature         1..20
                     note = Description of sequence: Primer: Fungi-quant-F
source               1..20
                     mol_type = other DNA
                     organism = synthetic construct
SEQUENCE: 5
ggraaactca ccaggtccag                                                   20

SEQ ID NO: 6         moltype = DNA  length = 18
FEATURE              Location/Qualifiers
misc_feature         1..18
                     note = Description of sequence: Primer: Fungi-quant-R
source               1..18
                     mol_type = other DNA
                     organism = synthetic construct
SEQUENCE: 6
gswctatccc cakcacga                                                     18

SEQ ID NO: 7         moltype = DNA  length = 15
FEATURE              Location/Qualifiers
misc_feature         1..15
                     note = Description of sequence: DNA Probe
source               1..15
                     mol_type = other DNA
                     organism = synthetic construct
SEQUENCE: 7
tggtgcatgg ccgtt                                                        15
```

FECAL FUNGOME AND THERAPEUTIC EFFICACY OF FECAL MICROBIOTA TRANSPLANTATION

This application is a divisional of U.S. patent application Ser. No. 16/966,853 filed Jul. 31, 2020, which is the U.S National Stage Entry under § 371 of International Application No. PCT/CN2019/074353, filed Feb. 1, 2019, which claims priority to U.S. Provisional Patent Application No. 62/625,705, filed Feb. 2, 2018, and U.S. Provisional Patent Application No. 62/679,417, filed Jun. 1, 2018, the contents of both are hereby incorporated by reference in the entirety for all purposes.

BACKGROUND OF THE INVENTION

Reference to Sequence Listing

A Sequence Listing conforming to the rules of WIPO Standard ST.26 is hereby incorporated by reference. Said Sequence Listing has been filed as an electronic document via PatentCenter in ASCII format encoded as XML. The electronic document, created on Jun. 27, 2023, is entitled "080015-1362047-024030US_ST26.xml", and is 10,194 bytes in size.

Background of the Invention

*Clostridium difficile* infection (CDI) is a symptomatic infection due to the spore-forming bacterium, *Clostridium difficile*. *C. difficile* infection is spread by bacterial spores found within feces. Risk factors for infection include antibiotic or proton pump inhibitors use, hospitalization, other health problems, and older age. Its symptoms including watery diarrhea, fever, nausea, and abdominal pain, CDI makes up about 20% of cases of antibiotic-associated diarrhea. About 453,000 cases *C. difficile* infection occurred in the United States in 2011, resulting in 29,000 deaths. Each year, *C. difficile* infections accounts for health care cost of approximately $1.5 billion. Globally, rates of *C. difficile* infection have increased between 2001 and 2016, typically with more women than men affected by the infections.

Fecal microbiota transplantation (FMT) is highly effective for the treatment of CDI, especially among patients suffering from recurrent CDI. Also known as stool transplant, FMT involves a process of transplanting fecal matter containing microorganism from a healthy individual into the gastrointestinal tract of a recipient. The goal of FMT is restoration of the gut microflora disrupted due to CDI by introducing (or re-introducing) healthy bacterial flora via various means of infusion of a healthy individual's stool, e.g., by colonoscopy, enema, orogastric tube, or by mouth in the form of a capsule containing freeze-dried material obtained from a healthy donor. Aside from CDI, FMT is increasingly being used to treat other intestinal and extra-intestinal diseases, including other gastrointestinal diseases, such as inflammatory bowel disease (IBD), antibiotic-resistant bacterial infection, diarrhea, constipation, irritable bowel syndrome, autism, depression, obesity, diabetes, alopecia, and the like. In addition, FMT has been used for treating certain neurological conditions, such as multiple sclerosis and Parkinson's Disease. Considering the prevalence of CDI and other conditions treatable by FMT in the human population and their significant economic implications, there exists an urgent need for developing new and improved methods for treating CDI and other disorders by FMT with enhanced efficacy. The present invention fulfills this and other related needs.

BRIEF SUMMARY OF THE INVENTION

The invention relates to novel methods and compositions useful for more effectively treating *Clostridium difficile* infection (CDI) and other diseases suitable by fecal microbiota transplantation (FMT) treatment. In particular, the present inventor discovered that, when elevated level of the yeast species *Candida albicans* is present in the gastrointestinal tract of an FMT recipient or in the stool of an FMT donor, therapeutic efficacy of FMT is negatively impacted. This finding allows the inventors to devise methods and compositions that can improve FMT effectiveness. Thus, in the first aspect, the present invention provides a novel method for assessing the likelihood of effective FMT. The method includes a step of determining *C. albicans* level in a stool sample obtained from a potential recipient prior to FMT is performed, i.e., before the recipient is to receive transplantation of a donor fecal material.

In some embodiments, the *C. albicans* level is a percentage relative abundance, or is expressed as a percentage over the total level of all fungal species in the sample. In some embodiments, when the *C. albicans* level is determined as greater than 10% of total fungi in the sample of the recipient, FMT is assessed as unlikely to be effective for the potential recipient. Under such a determination, the recipient in some cases will not receive FMT treatment but will receive another different therapy; in other cases, the recipient is administered an effective amount of an antifungal agent that suppresses *C. albicans* growth before FMT is performed. Optionally, after the administration of the antifungal agent, the *C. albicans* level in the recipient (e.g., in a recipient's stool sample) is again measured and determined to have been lowered before the recipient is transplanted with a composition containing donor fecal material. In some cases, *C. albicans* level is again determined in a stool sample obtained from the recipient after FMT.

In some embodiments, when the *C. albicans* level is no greater than 10% of total fungi in the sample, FMT is assessed as likely to be effective for the potential recipient. In some cases, the potential recipient is then immediately given FMT, without any further treatment or preparation such as administration of an antifungal agent in the effective amount. In some embodiments, the method further involves a step of determining total fungal load in the stool sample. A potential recipient whose total fungal load in his stool sample is found to be relatively lower than that of a second potential recipient is expected to have a higher likelihood of having a successful FMT than the second recipient. In some embodiments, multiple potential recipients of FMT are tested prior to FMT using this method for assessing their relative likelihood of success upon receiving FMT treatment. For instance, *C. albicans* level is determined in a first stool sample obtained from a first potential recipient prior to FMT, and in the meantime *C. albicans* level is determined in a second stool sample obtained from a second potential recipient prior to FMT. In some embodiments, when the first potential recipient has a lower *C. albicans* level than the second potential recipient and is therefore assessed to have a higher likelihood of effective FMT than the second potential recipient. In some embodiments, the second potential recipient is then administered an effective amount of an antifungal agent that suppresses *C. albicans* growth before FMT, whereas the first potential recipient may or may need antifungal agent treatment prior to FMT. In some embodiments, *C. albicans* level is determined by quantitative polymerase chain reaction (PCR). In some embodiments, the levels of all fungal species present in the sample is determined by the Internal transcribed spacer 2 (ITS2) sequencing. In some embodiments, the recipient or recipients suffer from inflammatory bowel disease (IBD) with concurrent *Clostridium difficile* infection (CDI). The *C. albicans* level in the stool may be determined before and after their FMT process. An elevated *C. albicans* level before or after FMT is indicative of a higher likelihood of poor outcome or ineffective FMT.

In a second aspect, the present invention provides a novel, improved method for identifying a suitable donor who would provide stool or fecal material for FMT. The method includes the step of determining *C. albicans* level in a stool sample obtained from a candidate who is being considered as a potential donor for FMT.

In some embodiments, the *C. albicans* level determined in this method is a percentage relative abundance. In some cases, when the *C. albicans* level is no greater than 0.1% of all fungi present in the sample, the candidate is identified as a suitable donor for FMT. Optionally, fecal matter such as stool is immediately collected from the candidate for use in FMT. In some cases, when the *C. albicans* level is greater than 0.1%, the candidate is deemed unsuitable as a donor for FMT. As a result, either no fecal matter is collected from the candidate at all; or fecal matter is collected for processing to be used in FMT after the candidate is given an effective amount of an antifungal agent that suppresses *C. albicans* growth and again tested to find a satisfactorily reduced *C. albicans* level in the stool sample (e.g., no greater than 0.1% of total fungi in the sample). In some embodiments, the stool sample of a candidate is tested for *Saccharomyces* level and *Aspergillus* level in addition to *C. albicans* level. In some embodiments, *C. albicans* level is determined by quantitative PCR. In some embodiments, the levels of all fungi present in the sample is determined by ITS2 sequencing. In some embodiments, the method includes the additional step of determining *Escherichia* level and *Proteus* level in the stool sample of a potential donor. Among multiple potential donors, one with a relatively high *Escherichia* level and a relatively low *Proteus* level is deemed a more suitable donor than one with a relatively low *Escherichia* level and/or a relatively high *Proteus* level. In some embodiments, the method further includes a step of determining the total fungal load in the stool sample taken from the potential donor. A potential donor whose total fungal load in his stool sample is found to be relatively lower than that of a second potential donor is expected to be a more desirable donor, i.e., provide a higher likelihood of a successful FMT, than the second donor.

In a third aspect, the present invention provides a method for improving FMT efficacy. The method includes the step of administering to an FMT recipient prior to FMT being performed an effective amount of an antifungal agent that suppresses *C. albicans* growth. In some embodiments of this method, *C. albicans* level is first determined in a stool sample from the FMT recipient prior to administration of the antifungal agent. In some embodiments, *C. albicans* level is determined in a stool sample from the FMT recipient after administration of the antifungal agent. In some embodiments, *C. albicans* level is determined by quantitative PCR. In some embodiments, the levels of all fungi present in the sample is determined by ITS2 sequencing. In some embodiments, the method further includes a step of administering to the recipient prior to FMT an effective amount of an agent (e.g., an anti-fungal agent, such as a broad-spectrum fungicide), which reduces total fungal load in a stool sample taken from the recipient prior to FMT. In some embodiments, the recipient is a patient suffering from inflammatory bowel disease (IBD) with concurrent *Clostridium difficile* infection (CDI).

In a fourth aspect, the present invention provides kits and compositions useful for enhanced FMT treatment with improved efficacy. In some embodiments, a kit for improving FMT efficacy includes a first composition comprising a donor stool material and a second composition comprising an effective amount of an antifungal agent capable of suppressing the growth of *C. albicans*. Typically, the first and second compositions are kept in two separate containers. In some embodiments, the first composition contains processed donor fetal matter and is formulated for FMT by direct transfer to the GI tract (e.g., via colonoscopy or via nasal intubation) or by oral ingestion. In some embodiments, the first composition comprises donor fecal matter further fortified with an additional and effective amount of one or more fungal species belonging to the genus *Saccharomyces* and/or the genus *Aspergillus*. In some embodiments, the second composition is formulated for administration of the antifungal agent (such as fluconazole) to the recipient by injection, oral ingestion, or rectal deposit. In some embodiments, the kit may further comprise, either in the second composition or in a third composition, an effective amount of an agent that reduces total fungal load. In the alternative, the kit may comprise a third composition, which comprises an effective amount of an agent that reduces total fungal load, but not the second composition. In some cases, the kit may further include printed user instructions.

Related compositions useful in FMT with improved efficacy may comprise (1) a donor stool material containing live fecal microorganisms and (2) an antifungal agent that specifically suppresses the growth or proliferation of *C. albicans* but exhibits no such suppressive or inhibitory effect against other fungal species. Instead of a broad-spectrum fungicide, such specific anti-*C. albicans* agent may be short polynucleotide in nature of (e.g., a small inhibitory RNA, microRNA, miniRNA, lncRNA, or an antisense oligonucleotide that is capable of disrupting the expression of a key gene in the life cycle of *C. albicans*) that is capable of specifically targeting the species only but not other closely related fungal species.

BRIEF DESCRIPTION OF THE DRAWINGS

FIG. 1a-FIG. 1e Fungal alterations in CDI. (FIG. 1a) Comparison of the fecal mycobiota based on Shanon diversity, evenness, Chao1 richness in controls and CDI subjects. The bars are shown in median and interquartile range. The dots indicate individual values of the studied subjects. Statistical significance was determined by Mann-Whitney test, *P<0.05, **P<0.01. (FIG. 1b) Fungal community structure difference between controls and CDI by NMDS (Non-metric multidimensional scaling) plot based upon Bray-Curtis distance among all samples. (FIG. 1c) Comparison of the fecal mycobiota composition between controls and CDI subjects at the phylum level. (FIG. 1d) Differentially enriched fungal species between controls and CDI. Statistical significance was determined by LefSe analysis with FDR correction (only those species with q values <0.05 and LDA effect size >2 are shown). Heatmap of the presence of these differential fungal species is shown in relative abundance intensity. LDA effect size, q value (FDR-adjusted P value) and species annotation are shown. Green bars and dots indicate species enriched in controls, while red bar and dot indicate species enriched in CDI. (FIG. 1e) Comparison of the relative abundance of fecal *C. albicans* in controls and CDI subjects. The bars are shown in median and interquartile range. Statistical significance was determined by Mann-Whitney test, *P<0.05.

(FIG. 2a) Presence of fungal operational taxonomic units (OTUs) in FMT recipients at the last follow-up. The color of the bar indicates the origin of the bacterial OTUs in the recipient. Purple indicates donor-derived OTUs colonized in the recipient, orange indicates OTUs exclusively present in recipient at baseline but not in donor at baseline, while green indicates OTUs present both in donor and in recipient before FMT. Comparison of the frequency of donor derived bacterial OTUs in FMT responders and in non-responders is shown. Statistical significance was determined by Mann-Whitney test, **P<0.01. (FIG. 2b) Presence of bacterial OTUs in FMT recipients at the last follow-up. Comparison of the frequency of donor-derived bacterial OTUs in FMT responders and in non-responders is shown. Statistical significance was determined by Mann-Whitney test, *P<0.05. (FIG. 2c) Heatmap of the abundance of differentially presented fungal genera in donor, pre-FMT and post-FMT last follow-up samples. Fungal genera with disparate presence between FMT responders and non-responders, as determined by LefSe analysis, are labeled with asterisk (genera with LDA effect size >2 and q value <0.01).

FIG. 3a-FIG. 3g Post-FMT alterations in the enteric mycobiota of CDI recipients in association with FMT response. Fecal fungal richness (FIG. 3a) and diversity (FIG. 3b) alterations in FMT recipients over the course of longitudinal follow-up and in their corresponding donors at baseline. Comparison of the fungal richness and diversity of pre-FMT samples and post-FMT samples collected at the last follow-up are shown in FMT responders and FMT non-responders respectively. Statistical significance was determined by paired Wilcox signed rank test, *P<0.05. "F" indicates FMT treated subject. "W" indicates weeks post treatment. (FIG. 3c) Alterations in the fecal fungal composition at the genus level in CDI recipients after FMT at different time points up to the last follow-up. (FIG. 3d) Differentially enriched fungal taxa across post-FMT fecal samples of FMT responders versus non-responders at the genus and species level respectively. Statistical significance level was determined by LefSe analysis with FDR correction (only those taxa with q values <0.05 and LDA effect size >2 are shown). Green bars and dots indicate taxa enriched in controls, while red bar and dot indicate taxa enriched in CDI. (FIG. 3e) Alterations of the relative abundance of fecal *C. albicans* after FMT at the last follow-up in FMT recipients. Statistical significance was determined by paired Wilcox signed rank test, *P<0.05. (FIG. 3f) Relative abundance of *C. albicans* in donor stool corresponding to FMT responders and non-responders. Statistical significance was determined by Chi-square test. (FIG. 3g) Relative abundance of *C. albicans* in stool of recipients before FMT in association with FMT response. Statistical significance was determined by Chi-square test.

(FIG. 4a) Schematic diagram of *C. albicans* administration and stool infusion (FMT) in a murine *C. difficile* infection (CDI) model. Antibiotic treatment was ceased before gavage of *C. albicans* (CA) and *C. difficile*. (FIG. 4b) Diarrhoea in mice on day 1 after stool infusion. (FIG. 4c) Representative H&E-stained colonic sections on day 2 after stool infusion (shaded star denotes inflammatory cells infiltration, hallowed star denote ulceration, asterisk denotes oedema, arrow denotes goblet cell loss and triangle denotes herniated crypts). Scale bar, 150 μm. n=5 mice per group. (FIG. 4d) Enumeration of *C. difficile* in feces of mice on day 0 before FMT and day 1 post FMT (n=9 mice per group). Statistical significance post FMT (n=9 mice per group). Statistical significance represents comparisons between FMT-treated mice with *C. difficile* infection versus other groups by unpaired Mann-Whitney test. * P<0.05, ** P<0.01. (FIG. 4e) Enumeration of *C. albicans* in feces of mice both on day 0 before FMT and day 1 post FMT (n=9 mice per group). Statistical significance represents comparison between *C. albicans* load on day 0 before FMT and day 1 post FMT, by paired Mann-Whitney test. * P <0.05. Dot graphs show means±s.e.m, performed at least two times independently.

(FIG. 5a), qPCR detection of *C. albicans* on CDI subjects and healthy controls from the discovery cohort. Comparison of the fecal *C. albicans* level between control and CDI was determined by Mann-Whitney test, ****P<0.0001. (FIG. 5b), qPCR detection of *C. albicans* on an additional set of subjects (17 healthy individuals, 12 CDI subjects with and 12 without antibiotic use at inclusion). Statistical significance was tested by unpaired Mann-Whitney test. * P<0.05, ** P<0.01. Graphs are shown in mean±s.e.m. ND denotes no detectable *C. albicans* in the feces as determined by quantitative PCR.

FIG. 6 Longitudinal timeline of stool sample collection (expressed in weeks). "F" indicates FMT treated subject. "Donor" indicates FMT donor. "S" indicates subject treated with standard therapy (STD, vancomycin). "W" indicates weeks post treatment. Red dots indicate donor samples, green dots indicate FMT recipient samples sampled at different time points.

(FIG. 8a) Comparison of the fecal bacterial shanon diversity, evenness, chao1 richness in healthy controls and in CDI subjects. The bars are shown in median and interquartile range. The dots indicate individual values of the studied subjects. Statistical significance was determined by Mann-Whitney test, **P<0.01. Fecal bacterial richness (FIG. 8b) and diversity (FIG. 8c) alterations in FMT recipients over the course of longitudinal follow-up and in their corresponding donors at baseline. Comparison of the fungal richness and diversity of pre-FMT samples and post-FMT samples collected at the last follow-up are shown in FMT responders and FMT non-responders respectively. Statistical significance was determined by paired Wilcox signed rank test, *P<0.05. "F" indicates FMT treated subject. "W" indicates weeks post treatment.

FIG. 9a-FIG. 9f Post-antibiotic alterations in the enteric mycobiota of CDI subjects treated with vancomycin in association with treatment response. Fecal fungal richness (FIG. 9a) and diversity (FIG. 9b) alterations over the course of longitudinal follow-up in CDI subjects who received vancomycin treatment. "S" indicates CDI subject received vancomycin treatment (standerd therapy, STD). "W" indicates weeks post vancomycine treatment. (FIG. 9c) Frequencies of CDI individuals increased or decreased in fungal diversity and richness post treatment with respect to FMT and STD treatment. Statistical significance was determined by Chi-square test, *P<0.05. (FIG. 9d) Comparison of post-FMT fold change (FC) of the fecal fungal diversity relative to the pre-FMT sample in FMT responders and STD responders. Statistical significance was determined by Chi-square test, *P<0.05. (FIG. 9e) Comparison of post-FMT fold change (FC) of the fecal fungal richness relative to the pre-FMT sample in FMT responders and STD responders. Statistical significance was determined by Man-whitney test, *P<0.05. (FIG. 9f) Alterations in the fecal fungal composition at the genus level in CDI subjects on vancomycin regime at different time points up to the last follow-up.

(FIG. 15a) Schematic diagram of antifungal treatment and stool infusion (FMT) in a murine model with di-colonisation of C. albicans and C. difficile. Antifungal (fluconazole) treatment was ceased at day 4 after administration of C. albicans when C. albicans was determined negative by cultivation. "CCfF", mouse group with di-colonisation of C. albicans and C. difficile and treatments of fluconazole and FMT; "CCF", mouse group with di-colonisation of C. albicans and C. difficile and treatment of FMT; "CC", mouse group with di-colonisation of C. albicans and C. difficile. (FIG. 15b) Enumeration of C. difficile in feces of mice on day 0 before FMT and day 1 post FMT (n=10 mice per group). Statistical significance was determined by unpaired Mann-Whitney test. * P <0.05,  P<0.01. (FIG. 15c) Enumeration of C. albicans in feces of mice both on day 0 before FMT and day 1 post FMT (n=10 mice per group). Statistical significance represents comparison between C. albicans load on day 0 before FMT and day 1 post FMT, by paired Mann-Whitney test.  P<0.01. Dot graphs show means±s.e.m, performed at least two times independently.

(FIG. 18a) Comparison of the total fungal load in the feces of controls and IBD subjects, including patients with CD and UC. Statistical significance was determined by Mann-Whitney test, ***P<0.001, *P<0.05. (FIG. 18b) Comparison of C. albicans levels in the feces of controls and CDI subjects.

(FIG. 20c), Heatmap of the relative abundance of differentially presented bacterial genera in donor, pre-FMT and post-FMT last follow-up samples. (FIG. 20d), Differentially presented bacteria taxa across post-FMT samples of FMT responders versus non-responders at the phylum, family, and genus levels. Statistical significance level was determined by LefSe analysis with FDR correction (only those taxa with q values <0.05 and LDA effect size >2 are shown).

DEFINITIONS

Figure 1D:
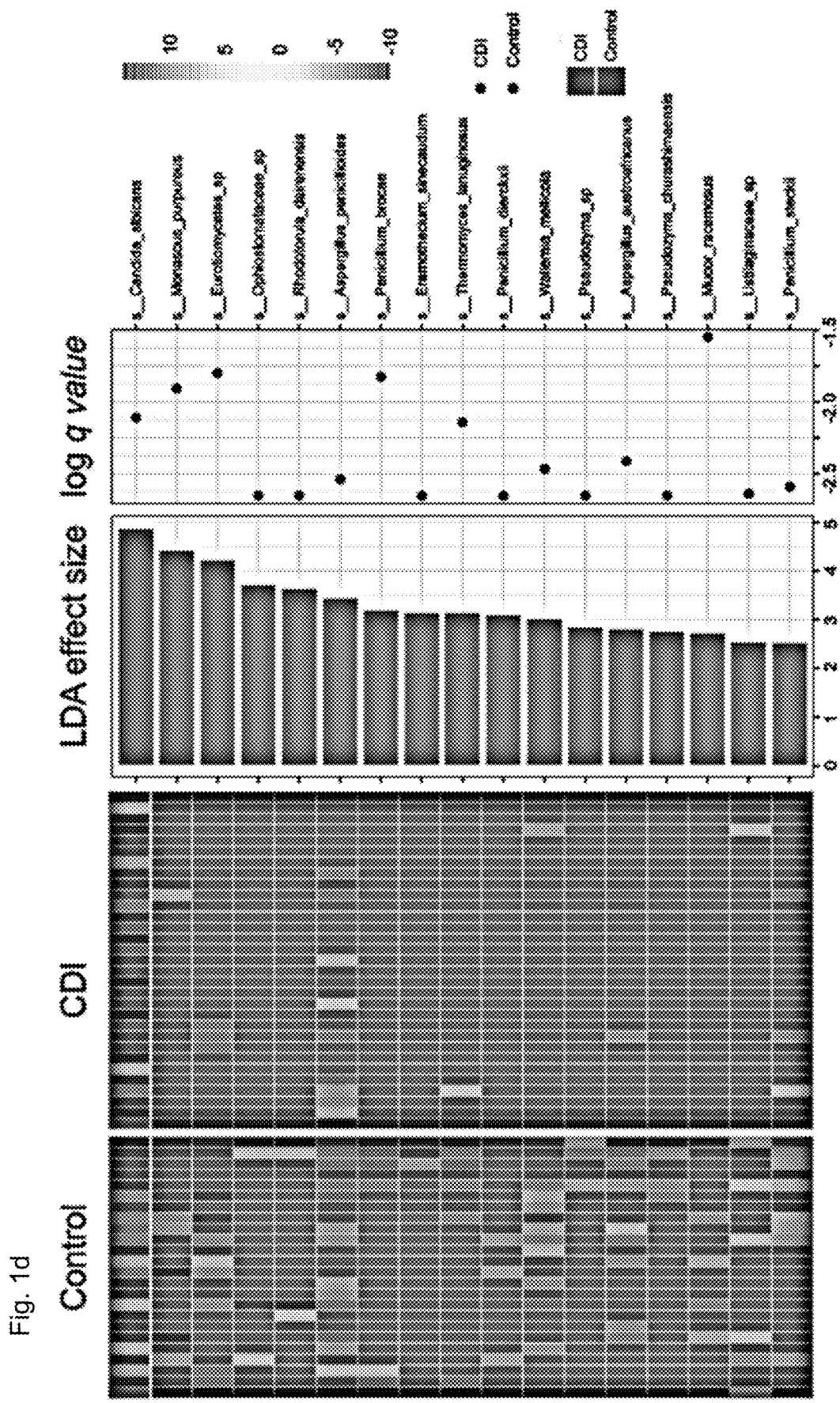

The term "fecal microbiota transplantation (FMT)" or "stool transplant" refers to a medical procedure during which fecal matter containing live fecal microorganisms (bacteria, fungi, and the like) obtained from a healthy individual is transferred into the gastrointestinal tract of a recipient to restore healthy gut microflora that has been disrupted or destroyed by a variety of medical conditions. Typically, the fecal matter from a healthy donor is first processed into an appropriate form for the transplantation, which can be made through direct deposit into the lower gastrointestinal tract such as by colonoscopy, or by nasal intubation, or through oral ingestion of an encapsulated material containing dried and frozen fecal matter. Clostridium difficile infection (CDI) is the condition most commonly treated by FMT, although a number of other diseases and disorders including in the digestive system and in the nervous system have been reported to be successfully treated by FMT.

The term "inhibiting" or "inhibition," as used herein, refers to any detectable negative effect on a target biological process, such as RNA/protein expression of a target gene, the biological activity of a target protein, cellular signal transduction, cell proliferation, and the like. Typically, an inhibition is reflected in a decrease of at least 10%, 20%, 30%, 40%, 50%, 60%, 70%, 80%, 90% or greater in the target process (e.g., growth or proliferation of fungal cells), or any one of the downstream parameters mentioned above, when compared to a control. "Inhibition" further includes a 100% reduction, i.e., a complete elimination, prevention, or abolition of a target biological process or signal. The other relative terms such as "suppressing," "suppression," "reducing," and "reduction" are used in a similar fashion in this disclosure to refer to decreases to different levels (e.g., at least 10%, 20%, 30%, 40%, 50%, 60%, 70%, 80%, 90% or greater decrease compared to a control level) up to complete elimination of a target biological process or signal. On the other hand, terms such as "activate," "activating," "activation," "increase," "increasing," "promote," "promoting," "enhance," "enhancing," or "enhancement" are used in this disclosure to encompass positive changes at different levels (e.g., at least 10%, 20%, 30%, 40%, 50%, 60%, 70%, 80%, 90%, 100%, 200%, or greater such as 3, 5, 8, 10, 20-fold increase compared to a control level) in a target process or signal.

As used herein, "C. albicans" refers to a fungal species belonging to the Candida genus, Saccharomycetaceae family, Saccharomycetales order, Saccharomycetes class, and Ascomycota division. A common member of the human gut flora, C. albicans is a potential yeast pathogen capable of causing opportunistic infection in humans, especially in those with compromised immune system.

The term "antifungal agent" refers to any substance that is capable of inhibiting, suppressing, or preventing the growth or proliferation of fungal species, especially those of the Ascomycota division, such as C. albicans. Known agents with fungicidal activity include amphotericin B, echinocandin, fluconazole, nystatin, and clotrimazole.

"Percentage relative abundance," when used in the context of describing the presence of a particular fungal species (e.g., C. albicans) in relation to all fungal species present in the same environment, refers to the relative amount of the fungal species out of the amount of all fungal species as expressed in a percentage form. For instance, the percentage relative abundance of C. albicans can be determined by comparing the quantity of C. albicans-specific DNA (e.g., determined by quantitative polymerase chain reaction) in one given sample with the quantity of all fungal DNA (e.g., determined by quantitative PCR and sequencing based on the Internal transcribed spacer 2 or ITS2 sequence) in the same sample.

"Absolute abundance," when used in the context of describing the presence of a particular fungal species (e.g., C. albicans) in the feces, refers to the amount of DNA derived from the fungal species out of the amount of all DNA in a fecal sample. For instance, the absolute abundance of C. albicans can be determined by comparing the quantity of C. albicans-specific DNA (e.g., determined by quantitative polymerase chain reaction) in one given sample with the quantity of all fecal DNA in the same sample.

"Total fungal load" of a fecal sample, as used herein, refers to the amount of all fungal DNA out of the amount of all DNA in the fecal sample. For instance, the absolute abundance of fungi can be determined by comparing the quantity of fungal specific DNA (e.g., 18S rDNA determined by quantitative polymerase chain reaction) in one given sample with the quantity of all fecal DNA in the same sample.

The term "effective amount," as used herein, refers to an amount of a substance that produces a desired effect (e.g., an inhibitory or suppressive effect on C. albicans growth) for which the substance (e.g., an antifungal agent) is used or administered. The effects include the prevention, inhibition, or delaying of any pertinent biological process during C. albicans growth or development to any detectable extent. The exact amount will depend on the nature of the substance (the active agent), the manner of use/administration, and the purpose of the application, and will be ascertainable by one skilled in the art using known techniques as well as those described herein.

As used herein, the term "about" denotes a range of value that is +/−10% of a specified value. For instance, "about 10" denotes the value range of 10+/−10×10%, i.e., 9 to 11.

DETAILED DESCRIPTION OF THE INVENTION

I. Introduction

The invention provides a novel approach for assessing the likelihood of effective FMT prior to the procedure being performed as well as for improving the effectiveness of the FMT procedure. During their studies, the present inventors discovered that the presence and relative abundance of certain fungal species both in a recipient's gastrointestinal tract and in a donor's stool directly correlate with the outcome of FMT. In particular, the fungal species Candida albicans of the Saccharomycetaceae family is found to negatively impact the effectiveness of FMT. The detection of C. albicans in a potential donor's stool thus can be used to guide donor selection, whereas analysis of C. albicans level in an FMT recipient can determine whether the subject is immediately ready for FMT or should be treated with an antifungal agent that suppresses C. albicans growth prior to FMT in order to optimize the therapeutic outcome.

II. FMT Donors and Recipients

Patients suffering from CDI, especially recurring CDI, are often considered as recipients for FMT treatment. Aside from CDI, other diseases and conditions, including those of digestive system or nervous system such as colitis, irritable bowel syndrome, multiple sclerosis, Parkinson's Disease, diabetes mellitus, and obesity are also beginning to be considered for FMT treatment.

Fecal matter used in FMT is obtained from a healthy donor and then processed into appropriate forms for the intended means of delivery in the upcoming FMT procedure. Up until now, the general criterion for an FMT donor is simply that the donor is a healthy individual without any known diseases or disorders especially in the digestive tract, although some preference is often given to the members of the same household as the recipient.

The present inventors have discovered in their studies that elevated presence of one particular fungal species, C. albicans, in a recipient's gastrointestinal tract or in a donor stool (which is used in the transplantation after being processed) can significantly reduce efficacy of FMT treatment in a patient. In contrast, successful FMT has been observed as correlating with elevated presence of other fungal species, such as those belonging to the genus of *Saccharomyces* or *Aspergillus*, in a recipient or in a donor stool. This revelation enables the initial screening of individuals as appropriate FMT donors as well as the initial screening of patients as likely candidates for successful FMT treatment: if a candidate donor's stool contains an elevated level of *C. albicans* (e.g., greater than 0.1% of total fungi), the candidate is deemed as unsuitable as an FMT donor, and his stool should not be taken or used in FMT; if a candidate's stool sample shows no or only low level of *C. albicans* (e.g., no greater than 0.1% of total fungi), then the candidate is deemed an appropriate FMT donor and his fecal material can be immediately retrieved for processing and later used in FMT. On the other hand, if a patient who has been proposed to receive FMT treatment, and his stool sample shows an elevated level of *C. albicans* (e.g., greater than 10% of total fungi), then the patient is deemed to be unsuitable to receive FMT and is therefore not to be given FMT, as the therapy is likely to be unsuccessful; if a patient's stool sample shows no or only a low level of *C. albicans* (e.g., no greater than 10% of total fungi), the patient is deemed an appropriate recipient for FMT who is likely to enjoy therapeutic success from FMT, and thus can start FMT treatment immediately without other steps of preparation or pre-treatment.

Various methods have been reported in the literature for determining the levels of all fungal species in a sample, for example, amplification (e.g., by PCR) and sequencing of fungal polynucleotide sequence by using the Internal transcribed spacer 2 (ITS2) sequence. On the other hand, the level of any given fungal species may be determined by amplification and sequencing of its signature 18S rRNA sequence. A percentage abundance is often used as a parameter to indicate the relative level of a fungal species in a given environment.

III. Methods for Improving FMT Efficacy

The discovery by the present inventors revealing the direct correlation between an elevated level of *C. albicans* in FMT donor or recipient and reduced efficacy of FMT treatment not only allows one to devise an initial screening process to identify appropriate donors and recipients for the FMT procedure, it also enables different methods for improving FMT efficacy by reducing the level of *C. albicans* in a donor and in a recipient prior to the FMT treatment.

As discussed in the above section, when a candidate donor's stool is tested and found to contain an elevated level of *C. albicans* (e.g., greater than 0.1% of total fungi), the candidate is deemed as unsuitable as an FMT donor, and his stool should not be taken for use in FMT as it is unlikely to result in a successful FMT treatment if used. Similarly, when a patient or proposed FMT recipient whose stool is tested and found to contain an elevated level of *C. albicans* (e.g., greater than 10% of total fungi), the patient is deemed as an unsuitable recipient for FMT, and he should not immediately undergo FMT due to the high probability of an ineffective outcome. Yet these cases of expected unsuccessful treatment outcome can be readily improved in view of the inventors' discovery.

First, for a patient who has been considered for receiving FMT but who has also been deemed an unsuitable recipient of FMT due to an elevated level of *C. albicans* (e.g., above 10% of total fungi) found in his/her stool sample, which indicates a diminished chance of a successful FMT, measures can be taken to lower his/her level of *C. albicans* before FMT is commenced so that a much greater efficacy can be achieved for the FMT procedure. For instance, an antifungal agent capable of suppressing the growth or proliferation of *C. albicans* can be administered to the patient in an effective amount such that the level of *C. albicans* in the patient's digestive track and in the feces is significantly reduced (e.g., no more than 10% of total fungi) prior to the start of the FMT procedure. In this case, the patient's *C. albicans* level is to be determined twice: once at the initial screening stage, a second time after the initial level is deemed too high for an effective FMT and after an antifungal agent has been given to the patient. Once the *C. albicans* level is confirmed as lowered to a percentage that would allow satisfactory FMT outcome, the patient is then ready to undergo FMT treatment.

Second, for a candidate who has been deemed improper to serve as an FMT donor due to a higher level of *C. albicans* in his stool, the expected undesirable FMT outcome can be remedied by treating the candidate donor with an effective amount of an antifungal agent capable of suppressing the growth or proliferation of *C. albicans* can be administered. Since the donor's body, especially the gastrointestinal track, contains a vast collection of microorganisms many of which are important for the health of gut microflora and for the success of FMT, a useful antifungal agent for this purpose cannot be a broad-spectrum fungicide. Rather, it should be an agent that narrowly and precisely targets the species of *C. albicans* without significantly affecting other fungal species, including those closely related to *C. albicans*. Although the agent may be of any chemical compound in nature, small polynucleotides (e.g., siRNAs, miRNAs, miniRNAs, lncRNAs, or antisense DNAs/RNAs) may be the most effective in achieving the specific task of disrupting the expression of one or more key genes in the life cycle of *C. albicans* so as to specifically inhibit the proliferation of the target species only without significant impact on other closely related fungal species.

Immediately upon completion of FMT procedure, the recipient may be further monitored by continuous testing of the level of *C. albicans* in the stool samples on a daily basis for up to 5 days post-FMT while the clinical symptoms of the condition being treated are also being monitored in order to assess FMT outcome and the corresponding *C. albicans* level in the recipient.

IV. Kits and Compositions for Improved FMT

The present invention also provides novel kits and compositions that can be used for improving FMT efficacy. For example, in a kit for treating a patient in need of FMT, a first composition intended for transplantation into a patient or FMT recipient and a second composition intended to be administered to the recipient for reducing the level of *C. albicans* in the recipient. The first composition comprises a fecal material from a donor, which has been processed, formulated, and packaged to be in an appropriate form in accordance with the delivery means in the FMT procedure, which may be by direct deposit in the recipient's lower gastrointestinal track (e.g., wet or semi-wet form) or by oral ingestion (e.g., frozen dried encapsulated). The second composition comprises an antifungal agent capable of suppressing the growth/proliferation of *C. albicans*, which may be a broad-spectrum fungicide or a specific inhibitor of the *C. albicans* species, and one or more pharmaceutically acceptable excipient. The composition is formulated for the intended delivery method of the antifungal agent, for example, by injection (intravenous, intraperitoneal, intramuscular, or subcutaneous injection) or by oral ingestion or by local deposit (e.g., suppositories). The first and second compositions are often kept separately in two different containers in the kit. Typically, the kit will further include printed material providing detailed instructions for users of the kit, such as providing information of the schedule and dosing arrangement for administering the first and second compositions to a recipient.

In another aspect of this invention, alternative compositions useful in FMT with improved efficacy may be devised to contain at least these two components: (1) a donor stool material containing live fecal microorganisms, and (2) an antifungal agent that specifically suppresses the growth or proliferation of *C. albicans* but exhibits no such suppressive or inhibitory effect against other fungal species. Component (2) preferably is not a broad-spectrum fungicide; rather, it should be a specific anti-*C. albicans* agent. For example, it may be short polynucleotide in nature of, e.g., a small inhibitory RNA, microRNA, miniRNA, lncRNA, or an antisense oligonucleotide, that is capable of disrupting the expression of at least one key gene in the life cycle of *C. albicans*, such that the agent is capable of specifically targeting the species only without significantly affecting other closely related fungal species. Component (2) is particularly useful in the case of a donor's stool containing a level of *C. albicans* too high to permit a satisfactory FMT outcome, as it is capable of locally and specifically suppressing the proliferation of *C. albicans* so as to ensure the success of FMT despite the less than desirable quality of the donor fecal material.

EXAMPLES

The following examples are provided by way of illustration only and not by way of limitation. Those of skill in the art will readily recognize a variety of non-critical parameters that could be changed or modified to yield essentially the same or similar results.

Example 1

Introduction

Fecal microbiota transplantation (FMT) is effective in treating recurrent *Clostridium difficile* infection (CDI) and is increasingly being utilized in other human diseases. Whilst bacteria colonization in recipients after FMT has been established, little is known of the role of the gut mycobiota. In this study the present inventors show gut fungal dysbiosis in CDI and identify that donor-derived fungi colonization in recipient is associated with FMT response. Mycobiota profiling in CDI reveals over-presentation of *C. albicans* and decreased fungal diversity, richness and evenness compared with healthy controls. Cure after FMT was observed when donor-derived fungal taxa predominated in recipients' mycobiota. FMT responders display a high prevalence of *Saccharomyces* and *Aspergillus* whilst non-responders and individuals treated with antibiotics display a dominant presence of *Candida*. High abundance of *C. albicans* in recipient before FMT and in donor stool nullifies FMT efficacy in eradicating CDI. Furthermore, *C. albicans* compromises FMT efficacy in a mouse model of CDI, while anti-fungal treatment reestablishes its efficacy. This study furthers the knowledge of human gut mycobiota dynamics and their contribution to FMT, and it enables an understanding of personalized donor-recipient selection in future FMT studies for various human diseases.

The past decade has witnessed an increasing use of fecal microbiota transplantation (FMT) as a promising treatment option for several diseases [1-3], yet success rates are variable with a cure rate of 85-90% in recurrent *Clostridium difficile* infections (CDI) [3-5] and a response rate of 30-40% in inflammatory bowel disease [6-8]. Such variations may be related to disease traits, recipient factors or donor characteristics. The mechanisms underlying a successful FMT and its relationship with gut microbial profiles in donor-recipient pairs remain elusive. To date, the efficacy of FMT has been mostly ascribed to the restoration of the bacterial microbiota and a sustained co-existence of donor and recipient bacterial strains [9-12]. Recently, bacteriophages have been shown to be altered in CDI after FMT and these changes were associated with treatment outcome [13-15]. The human gastrointestinal tract is also colonized by a large population of fungi, collectively referred to as the mycobiota, which play an important role in human health [16,17]. Gut mycobiota contribute to normal human physiology and in some cases can recapitulate the benefit of intestinal bacteria via regulating host immunity and maintaining intestinal homeostasis [16,17,18]. Whether donor-derived mycobiota can colonize a recipient host, the fate of donor and recipient mycobiota after FMT and their relationship with treatment outcomes are unknown. The inventors performed internal transcribed spacer 2 (ITS2) and 16S rDNA sequencing in FMT-treated subjects with CDI to explore the effects of FMT on the gut mycobiome in association with treatment outcome. A proof-of-causality study was conducted in *C. difficile*-infected mice to confirm the role of gut mycobiota in FMT response.

Results

Gut Fungal Dysbiosis in CDI

The fecal mycobiomes were compared between 31 CDI subjects and 23 healthy controls. There was a significant decrease in fungal diversity, evenness and richness in CDI compared with controls (Mann-Whitney test, p=0.0120, 0.0309, and 0.0043, respectively, FIG. 1a). The fungal communities of CDI subjects were significantly separated from those of healthy controls at the OTU level (based on Bray-Curtis distance, adonis test p=0.003, FIG. 1b). At the phylum level, Ascomycota was expanded in CDI compared with controls (Mann-Whitney test, p=0.0083, FIG. 1c). At the species level, 17 fungal species were found to be differentially present between CDI and controls (LefSe analysis with FDR adjusted q<0.05, FIG. 1d). Amongst these species, only *C. albicans* was significantly enriched in CDI (FIG. 1d, e, Mann-Whitney test, p=0.0080), whereas 16 other species were enriched in controls. In line with the observation at the species level, more taxa were enriched in controls than in CDI, as determined by LefSe analysis (9 versus 1 at the order level, 15 versus 2 at the family level, 16 versus 1 at the genus level, Table 2). Altogether, these data indicate dysbiosis of the enteric mycobiota in patients with CDI.

Figure 5B:
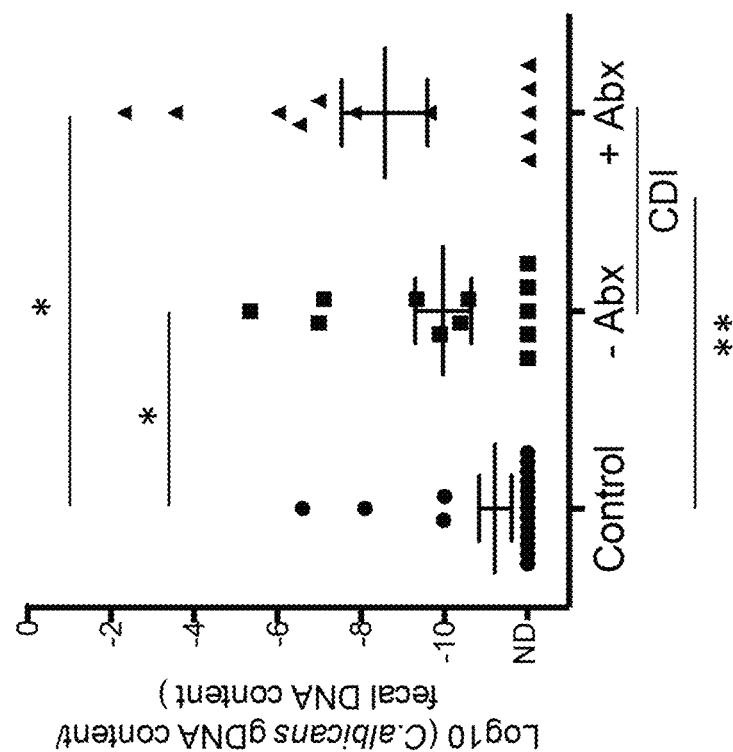
FIG. 5a-FIG. 5b Quantification of fecal *C. albicans* levels in CDI subjects and healthy controls by qPCR.
Figure 5A:
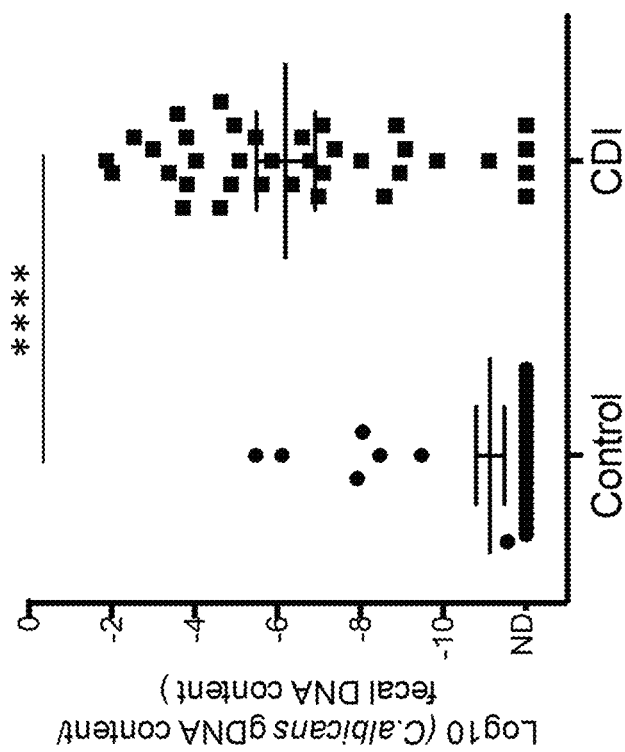

Over-presentation of *C. albicans* in absolute abundance in CDI was confirmed through quantitative PCR (FIG. 5a). Antibiotic use has been shown to be a major contributor to the development of CDI by decreasing bacterial colonization resistance. The effect of antibiotics on *C. albicans* levels in CDI was further assessed. Stool samples were collected from new consecutive CDI patients, including 12 CDI patients with antibiotics exposure, 12 CDI patients with no antibiotics exposure at inclusion, and 17 healthy controls. Significantly higher levels of fecal *C. albicans* were found in CDI subjects exposed to antibiotics at inclusion, compared with controls (FIG. 5b, Mann-Whitney test, p=0.0131). *C. albicans* levels were also significantly higher in CDI subjects not exposed to antibiotics at inclusion when compared with controls (FIG. 5b, Mann-Whitney test, p=0.0469). These data indicate that both CDI and antibiotics are contributors to increased levels of *C. albicans*.

Donor Fungi Colonization in Recipient is Associated with FMT Response

Figures 2A, 2B:
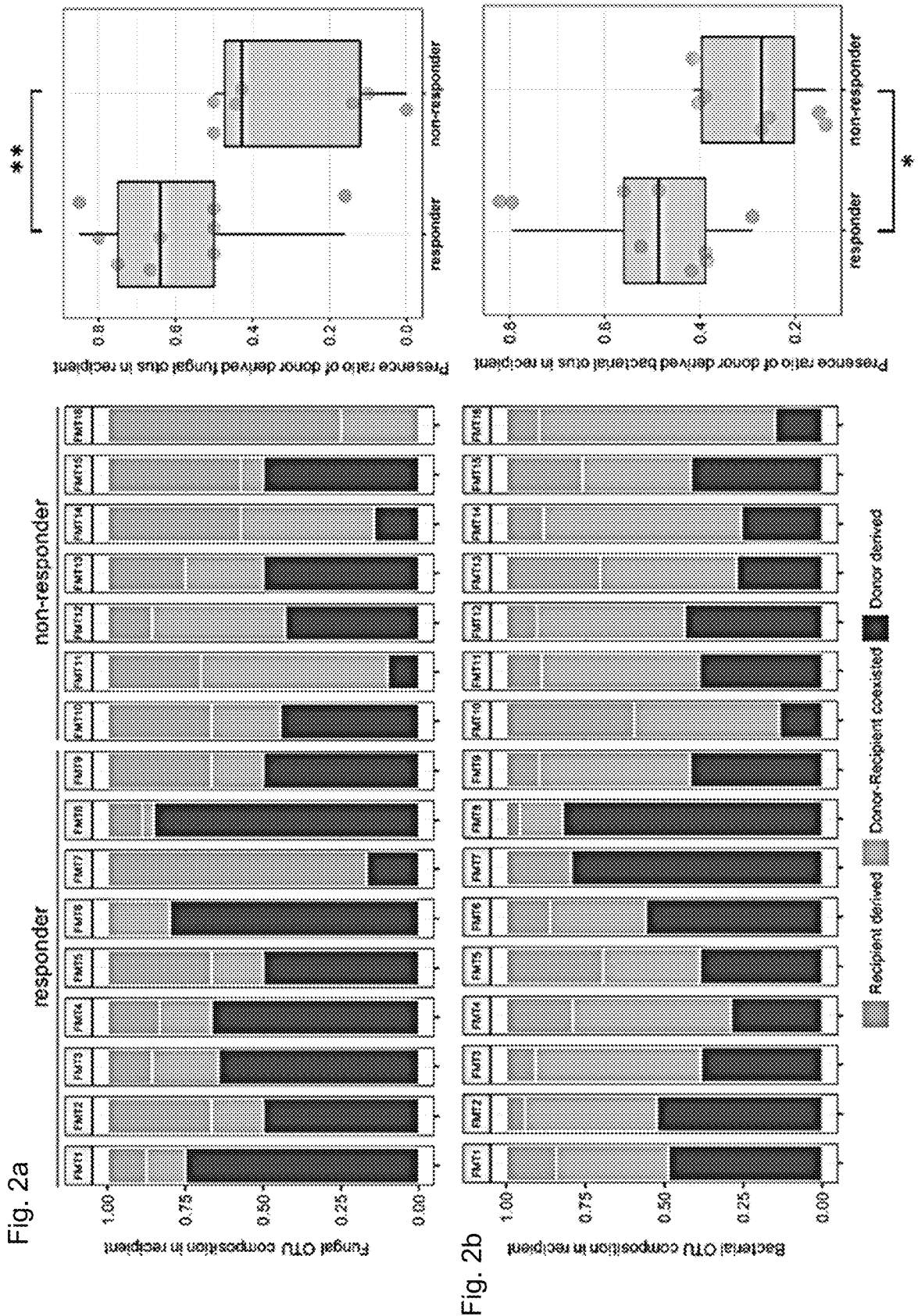
FIG. 2a-FIG. 2c Colonization of donor-derived fungal and bacterial taxa in FMT recipients in association with treatment response.
Figure 2C:
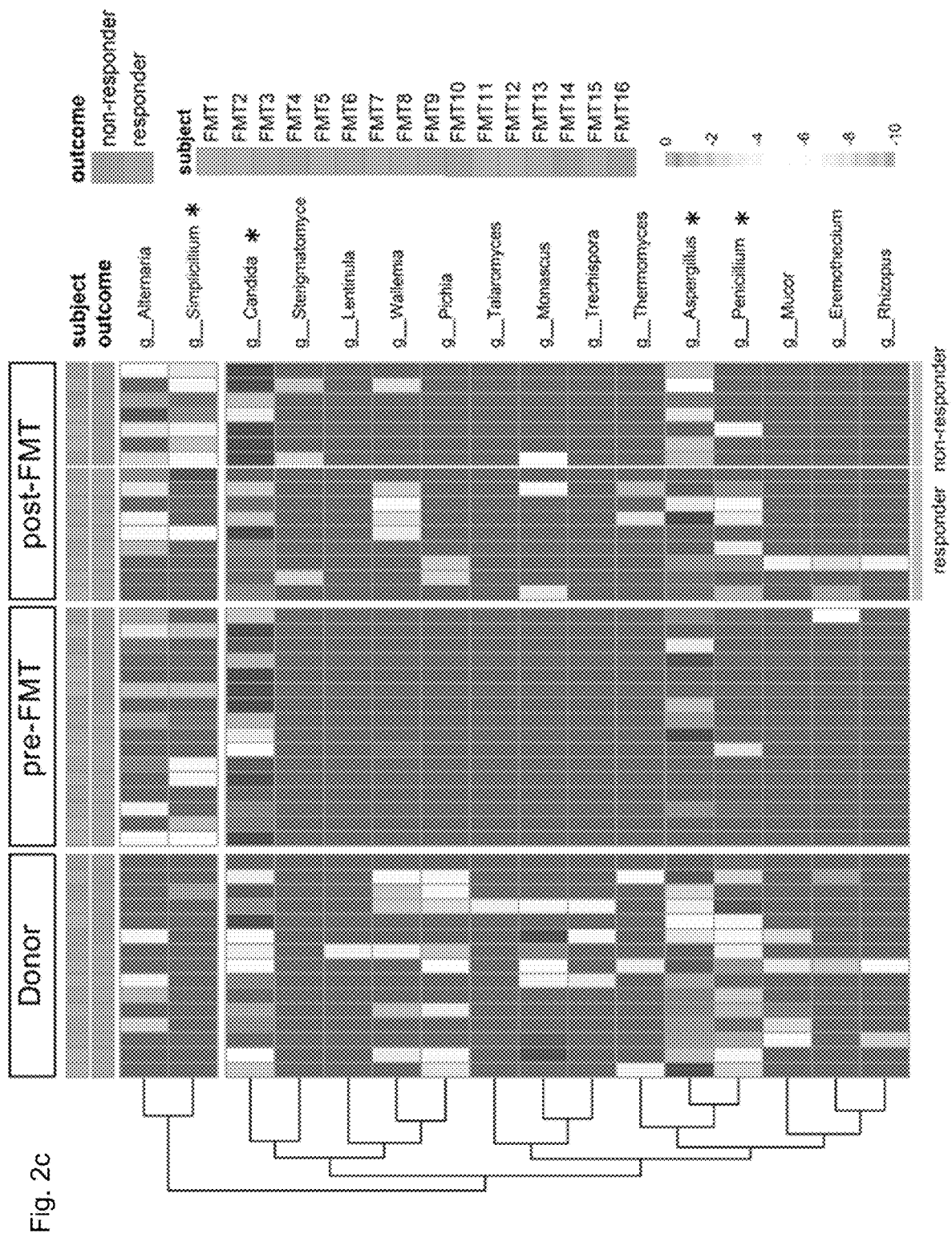
Figure 6:
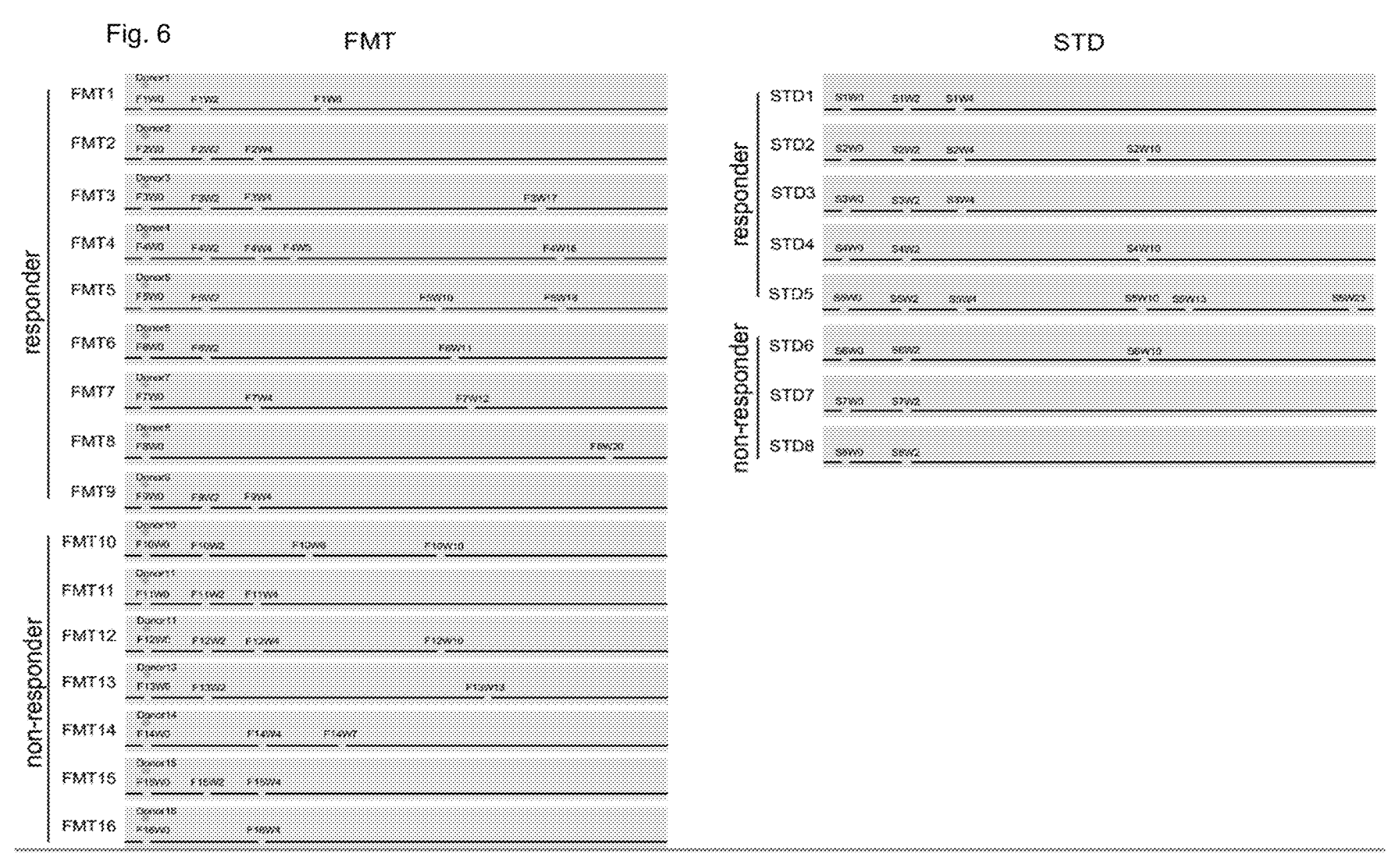
Figure 7:
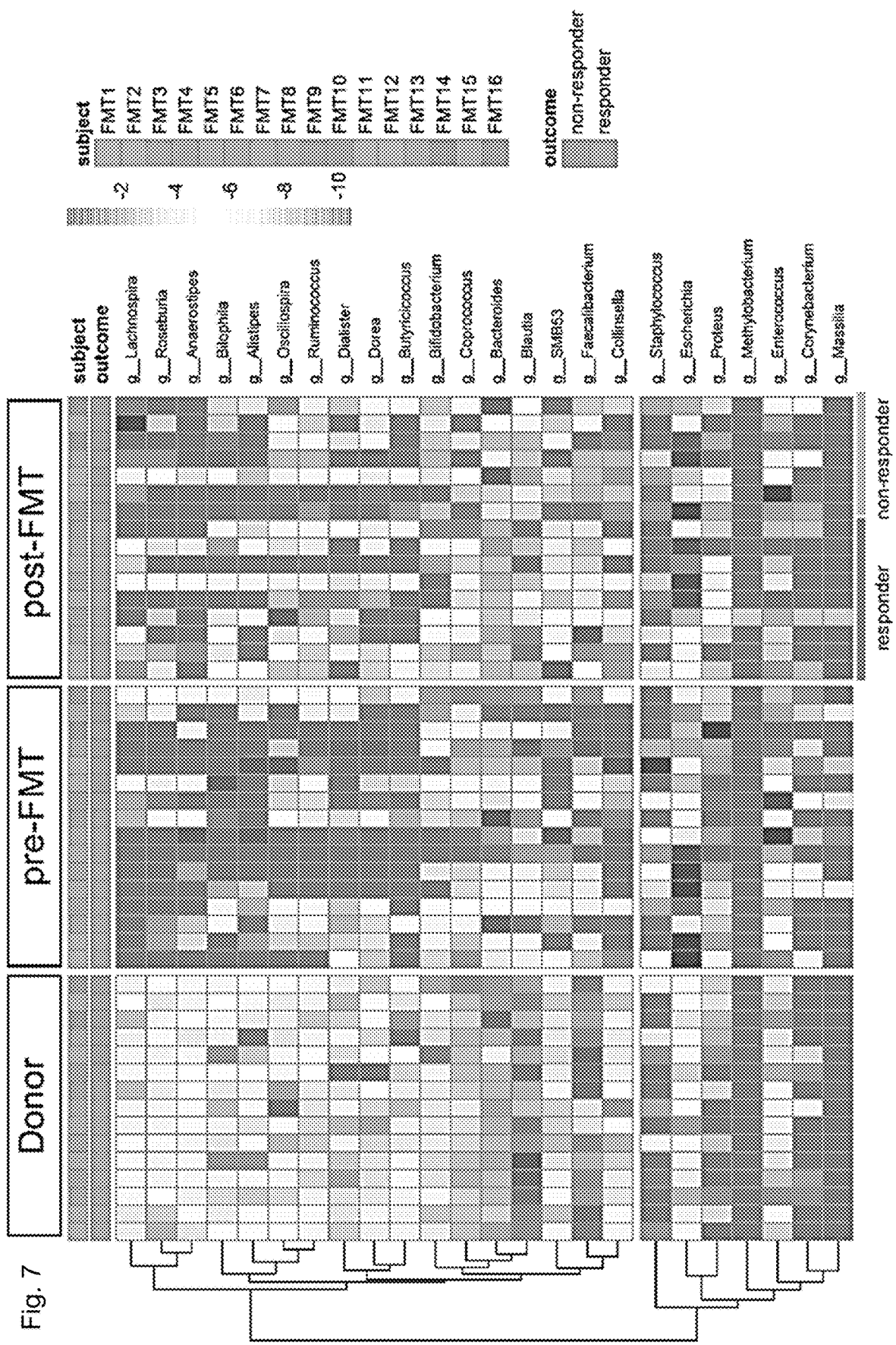
FIG. 7 Heatmap of the abundance of differentially presented bacterial genera in donor, pre-FMT and post-FMT last follow-up samples.

It was then explored whether FMT leads to colonization of donor-derived fungi and its association with treatment efficacy. Changes in the gut mycobiomes of recipients after FMT were monitored at multiple time points in 16 CDI subjects, using pre-FMT samples of each donor-recipient pair as a baseline for FMT (FIG. 6). Amongst 16 CDI subjects treated with FMT, nine remained symptom-free with a negative stool *C. difficile* toxin at the last follow-up (termed responders, FMT1-FMT9), whilst seven developed recurrence of CDI (termed non-responders, FMT10-FMT16) (Table 1). It was next investigated whether donor-derived fungi and bacteria in recipients may influence FMT outcomes. Subjects who responded to FMT demonstrated a larger proportion of fungal and bacterial OTUs that were transferred and predominated in the feces of recipients after FMT, compared to those who did not respond (Mann-Whitney test, p=0.0068 and 0.0164 respectively for comparison of donor-derived fungal and bacterial OTU ratios in recipients, FIG. 2a, b). The community structure at the genus level showed a higher abundance of the genera *Aspergillus* and *Penicillium* in FMT responders than in non-responders (FIG. 2c). In contrast, the genera *Candida* and *Simplicillium* were significantly enriched in FMT non-responders. Analogously, a similar pattern was observed at the bacterial community structure. FMT responders displayed bacterial abundance resembling that of the donor, whereas FMT non-responders showed inadequate abundance of donor-enriched bacteria at the last follow-up post FMT (FIG. 7). Of note, in recipients FMT12 and FMT16, bacterial configurations at the last follow-up after FMT were similar to that of healthy controls, but their gut mycobiota configurations differed significantly from that of healthy controls. These data indicate that restoration of the gut mycobiota is at least as important as, if not more than, restoration of the bacterial microbiota in CDI recipients. Taken together, these data indicate that the final proportion of donor-derived fungal and bacterial taxa and alterations of the fecal fungal composition in the recipient post FMT were associated with treatment outcome of FMT.

FMT Alters the Gut Mycobiota Distinct from Antibiotic Treatment

Figure 3B:
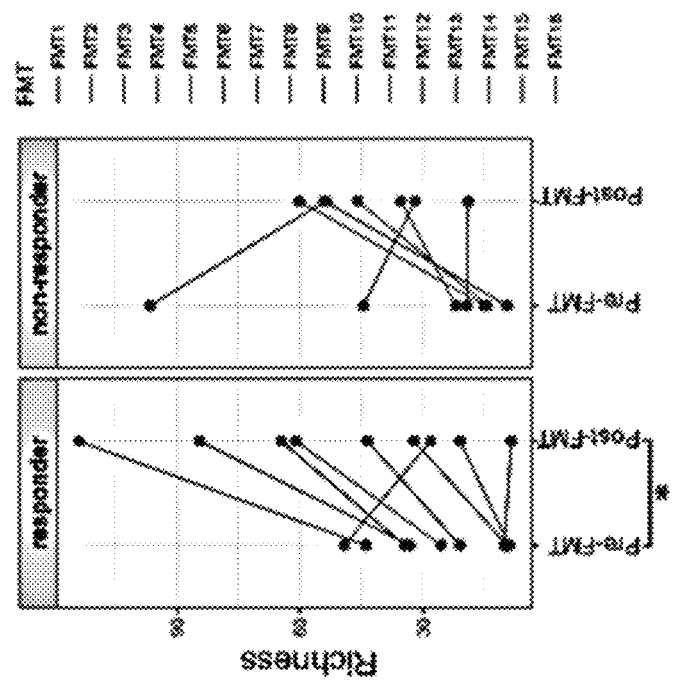
Figure 3B:
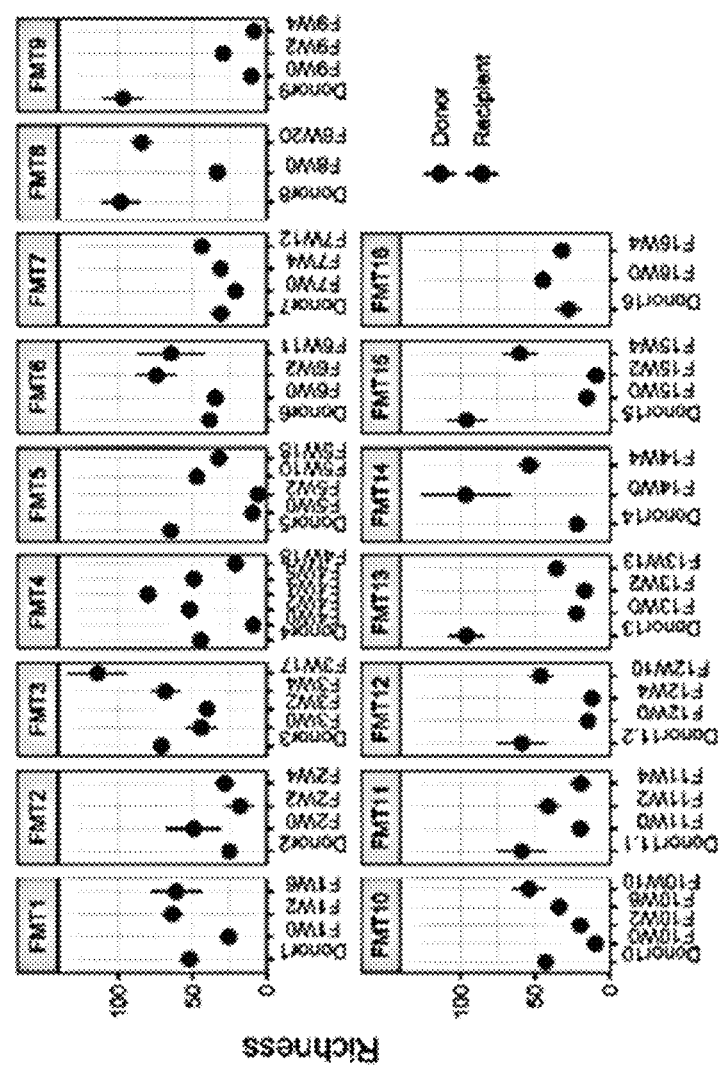
Figure 3C:
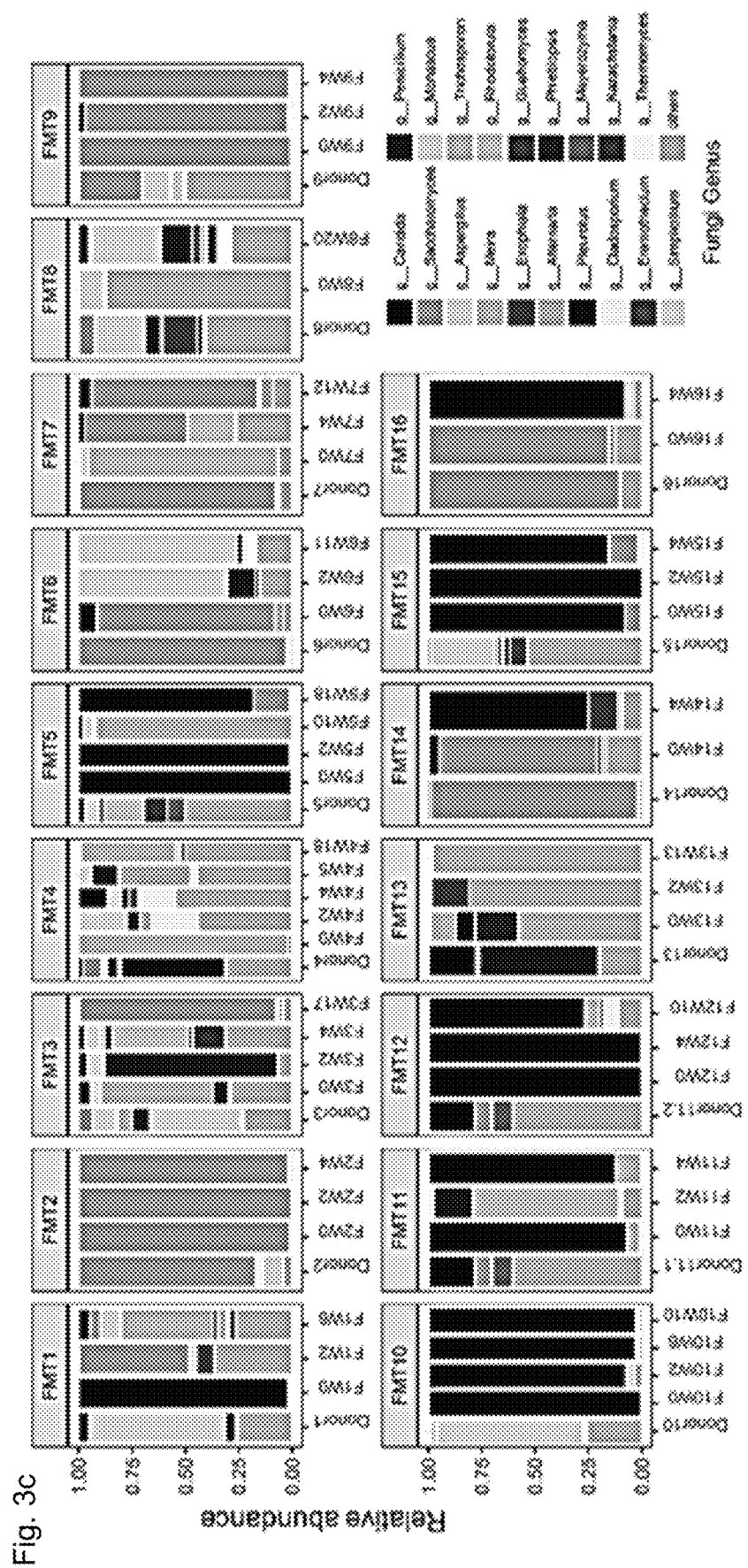

CDI subjects who responded to FMT showed a significant increase in fungal richness and diversity (Wilcoxon matched-pairs singed rank test, p=0.0273 and p=0.0474 respectively, FIG. 3a, b). Although baseline bacterial diversity, evenness and richness were significantly lower in CDI subjects compared to controls (Mann-Whitney test, all p<0.0001, FIG. 6a), after FMT there was a significant increase in bacterial richness (Wilcoxon matched-pairs singed rank test, p=0.019) and a marginally significant increase (Wilcoxon matched-pairs singed rank test, p=0.098) in bacterial diversity in FMT responders. During post-FMT follow-up, there were profound differences in the gut mycobiota configurations across different donor-recipient pairs, however a significantly higher prevalence of the genus *Candida* was observed across the serial post-FMT fecal samples of FMT non-responders relative to that of responders (FIG. 3c, d). In contrast, the genera *Saccharomyces* and *Aspergillus* were present in higher abundances in FMT responders than in non-responders (FIG. 3c, d). Discriminative analysis identified disparately presented taxa between post-FMT samples of FMT responders and non-responders, at the genus and species levels (FIG. 3d). *C. albicans* was the most prominent species enriched after FMT in non-responders.

Figure 16:
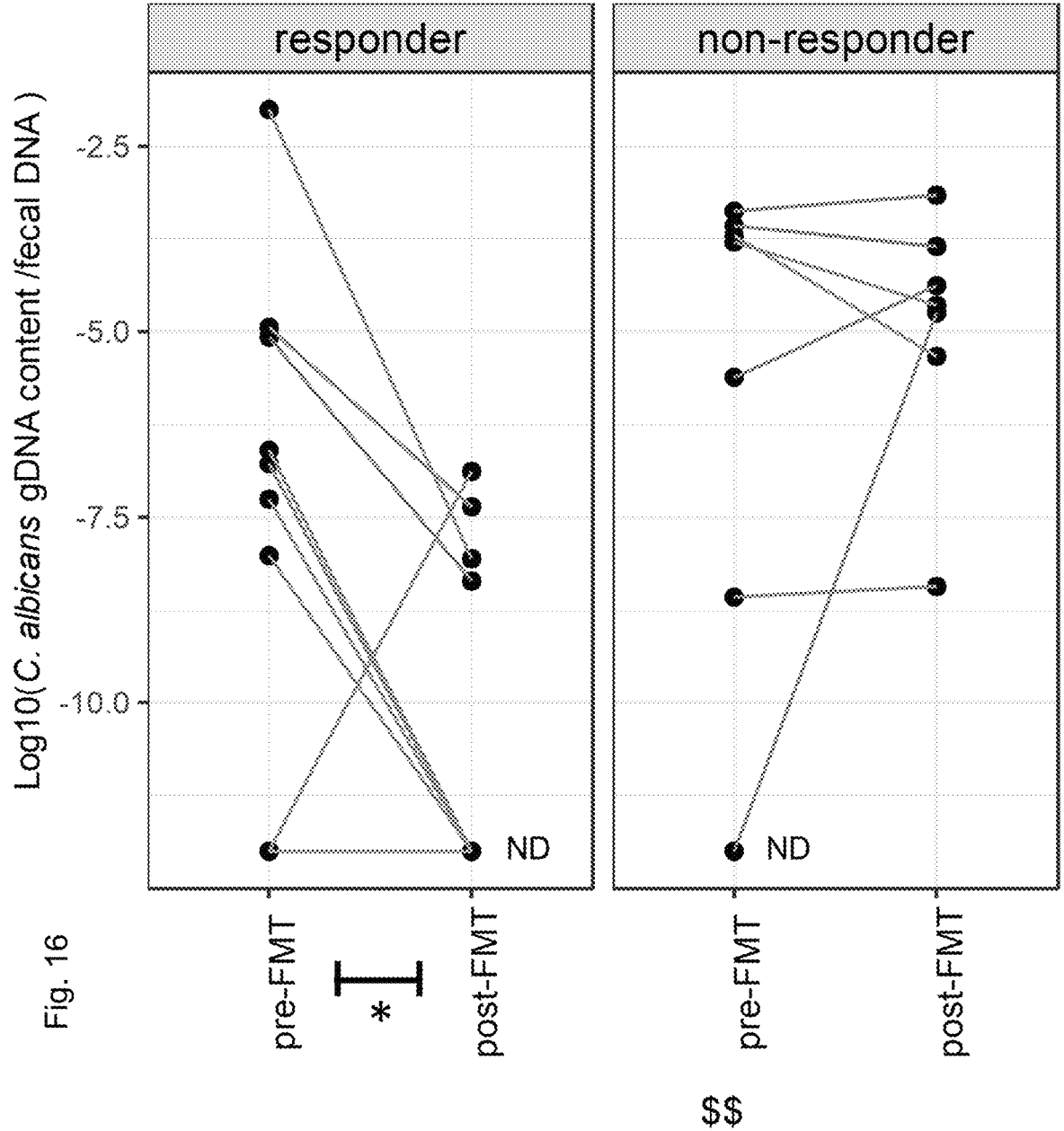
FIG. 16 The presence of C. albicans is linked to FMT outcomes in CDI. The absolute abundance of fecal C. albicans before and after FMT at the last follow-up in FMT recipients, assessed by quantitative PCR. Comparison of the fecal C. albicans levels between pre-FMT samples and post-FMT samples was performed by paired Wilcoxon signed rank test, *P<0.05. Comparison of the fecal C. albicans levels between the post-FMT samples of FMT responders and FMT non-responders was performed by Mann-Whitney test, $^{SS}$ P<0.01. ND denotes no detectable C. albicans in the feces.

*C. albicans* markedly decreased after FMT (Wilcoxon matched-pairs singed rank test, p=0.0458, FIG. 3d, e). Interestingly, both the abundance of *C. albicans* in donor feces and in post-FMT recipient fecal samples were associated with FMT treatment outcome. FMT recipients transplanted with a donor feces with *C. albicans* <0.1% in the fungal community achieved a response to FMT treatment, compared to those transplanted with a donor feces with *C. albicans* >0.1% (Chi-square test p=0.049, FIG. 3f). Recipients with an initial high abundance of *C. albicans* before FMT and continuing to have a relative abundance of *C. albicans* >10% after FMT all experienced a disease recurrence after FMT (Chi-square test p=0.029, FIG. 3g). These data indicate that the presence of *C. albicans* compromises FMT efficacy. The absolute abundance of *C. albicans* (in fecal input DNA) was markedly decreased after FMT in FMT responder group (Wilcoxon matched-pairs singed rank test, p=0.0391, FIG. 16). Interestingly, FMT non-responders exhibited significantly higher post-FMT fecal *C. albicans* levels in absolute abundance than FMT responders [Mann-Whitney test, p=0.0018, $Log_{10}$ transformed effect size 3.05 (95% CI: 1.48-4.29), FIG. 16], indicating *C. albicans* can be a marker for disease recurrence and/or pathogenesis.

Figure 9A:
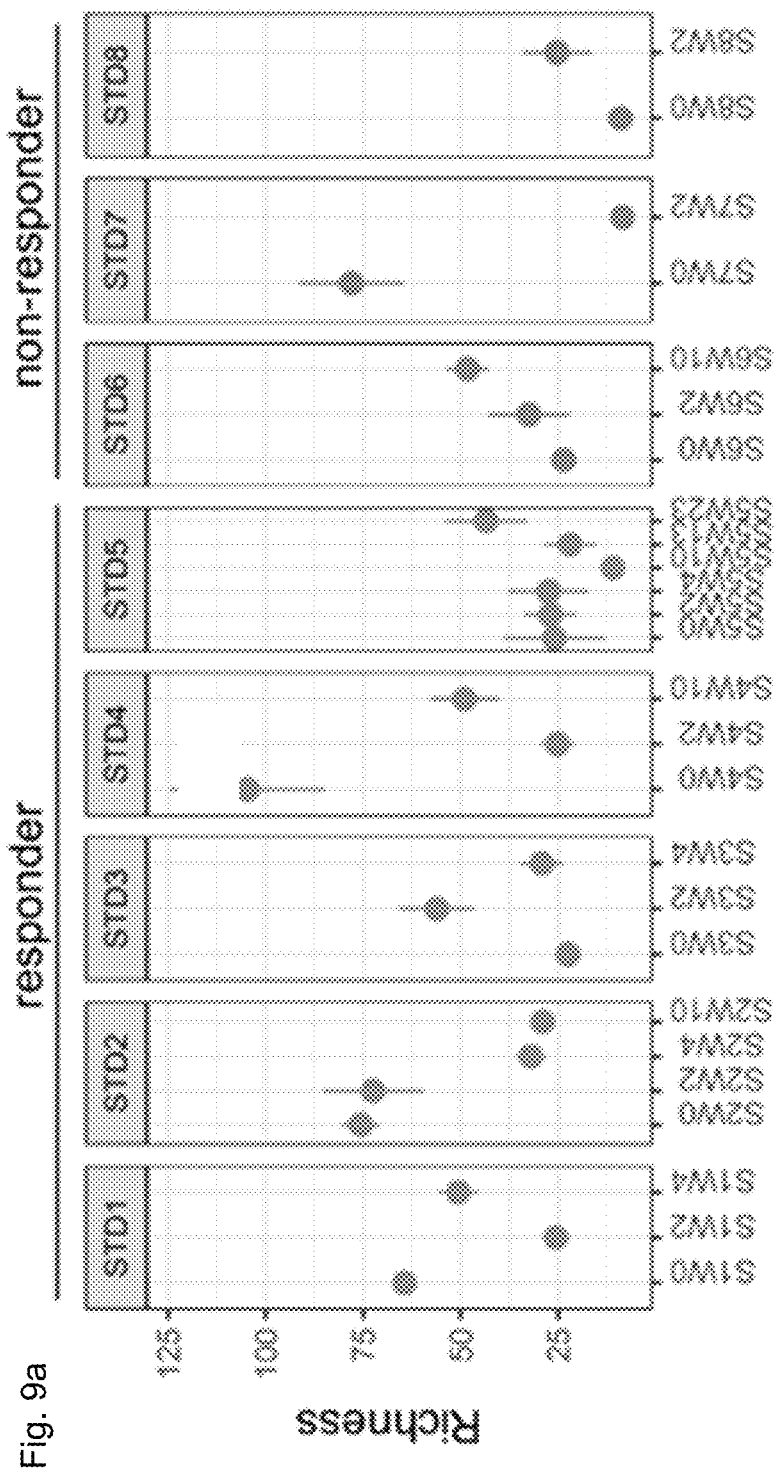
Figure 9B:
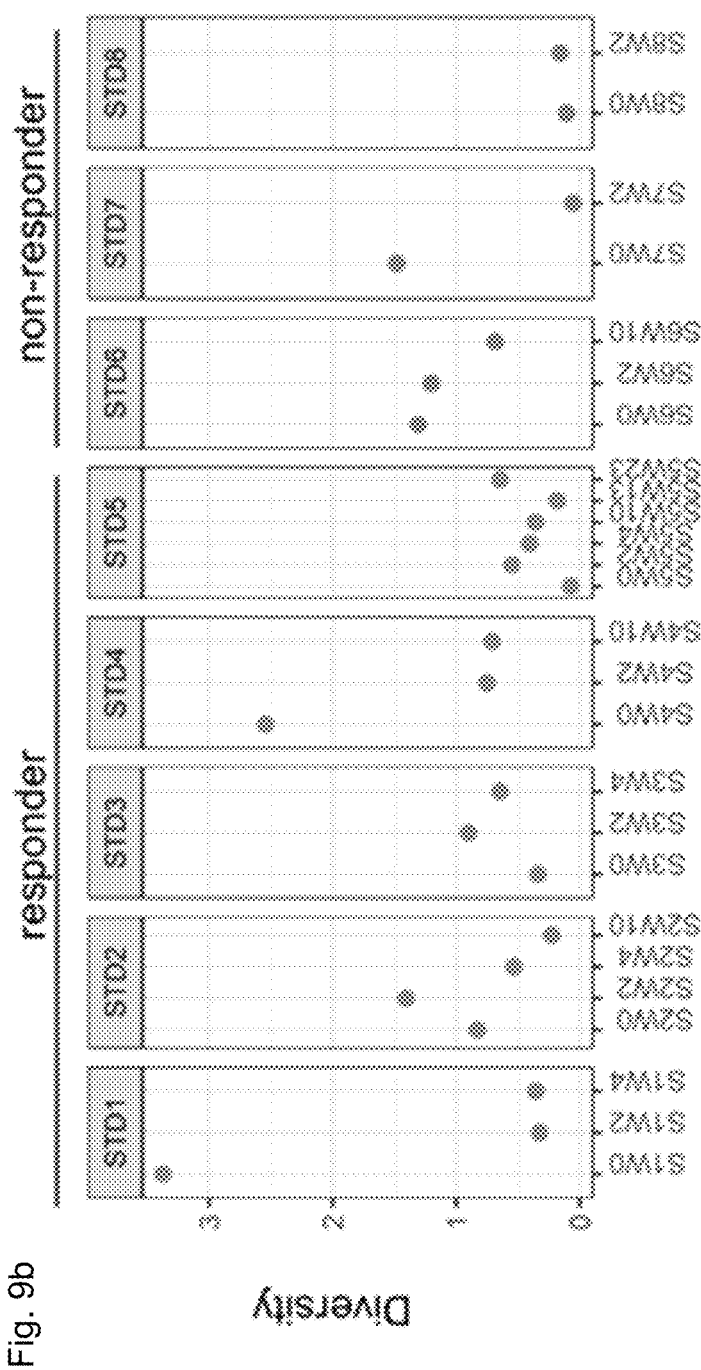
Figure 9E:
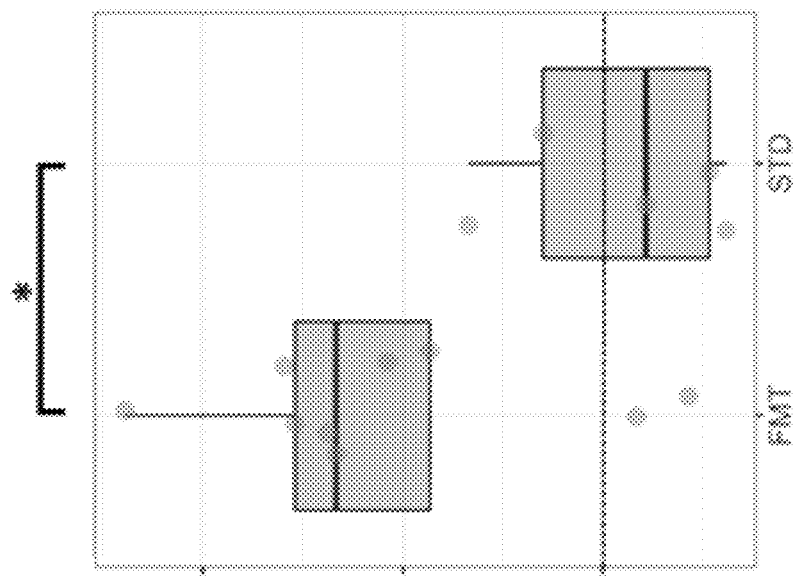
Figure 9D:
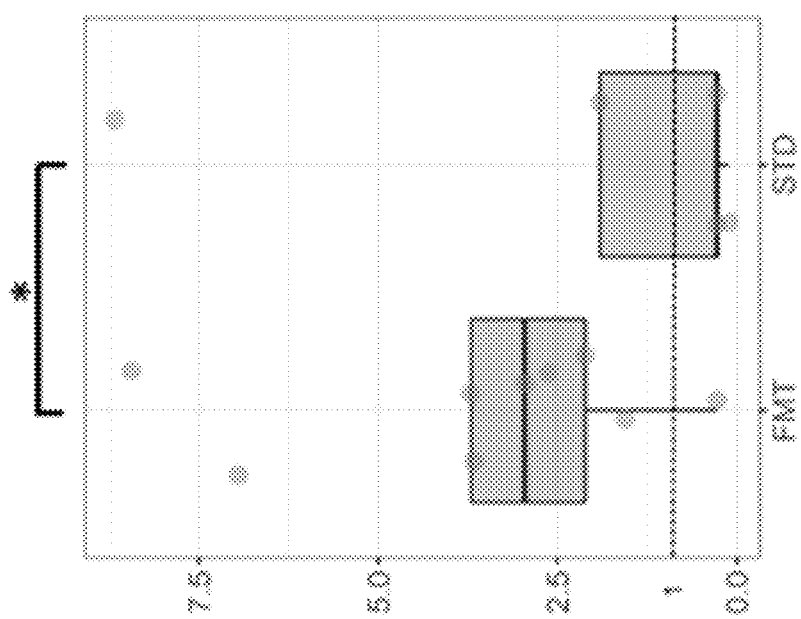
Figure 9F:
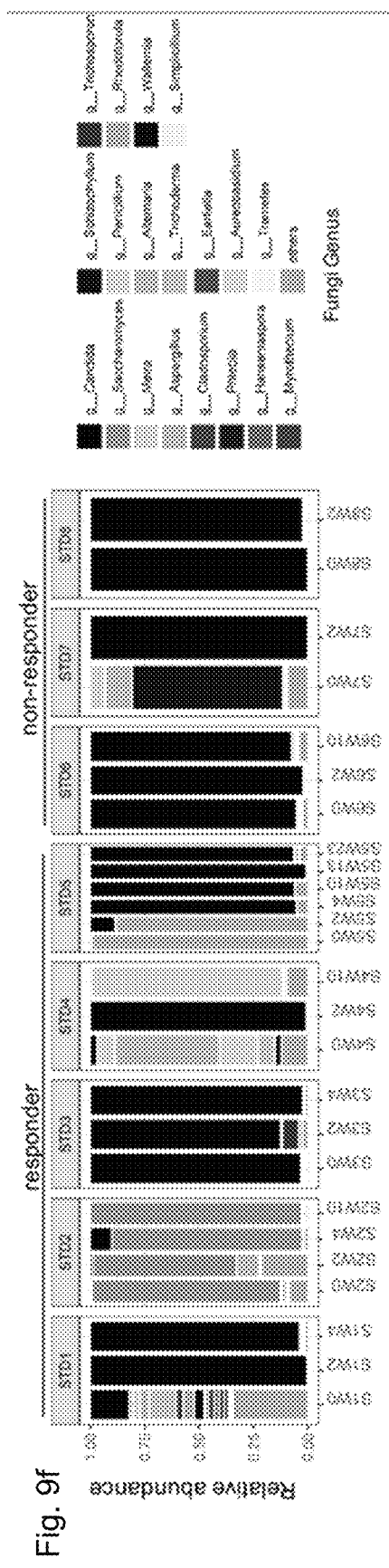
Figure 10A:
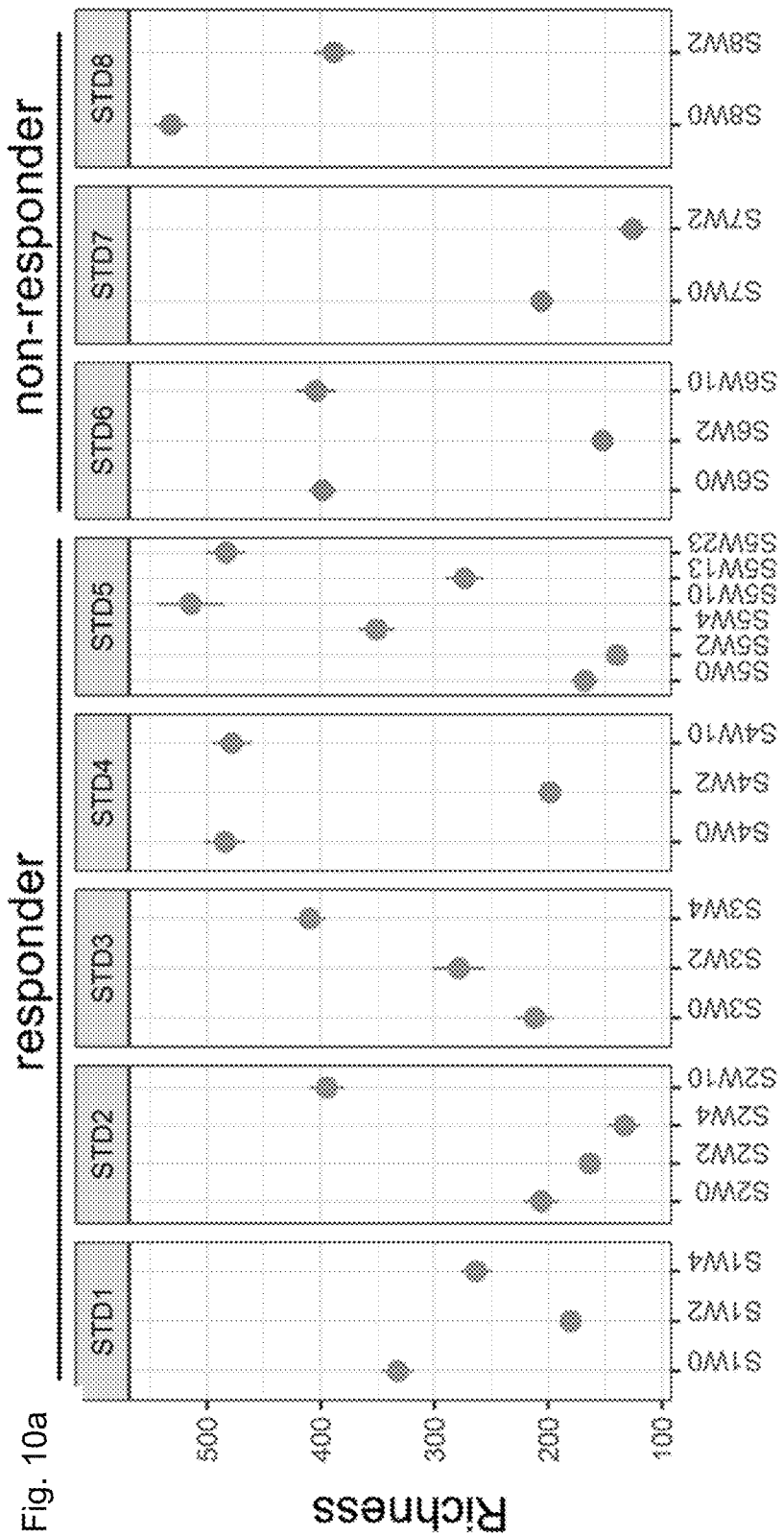
FIG. 10a-FIG. 10b Fecal bacterial microbiota richness and diversity alterations in STD subjects over the course of longitudinal follow-up. "S" indicates vancomycin treated subject (STD treatment). "W" indicates weeks post treatment.
Figure 10B:
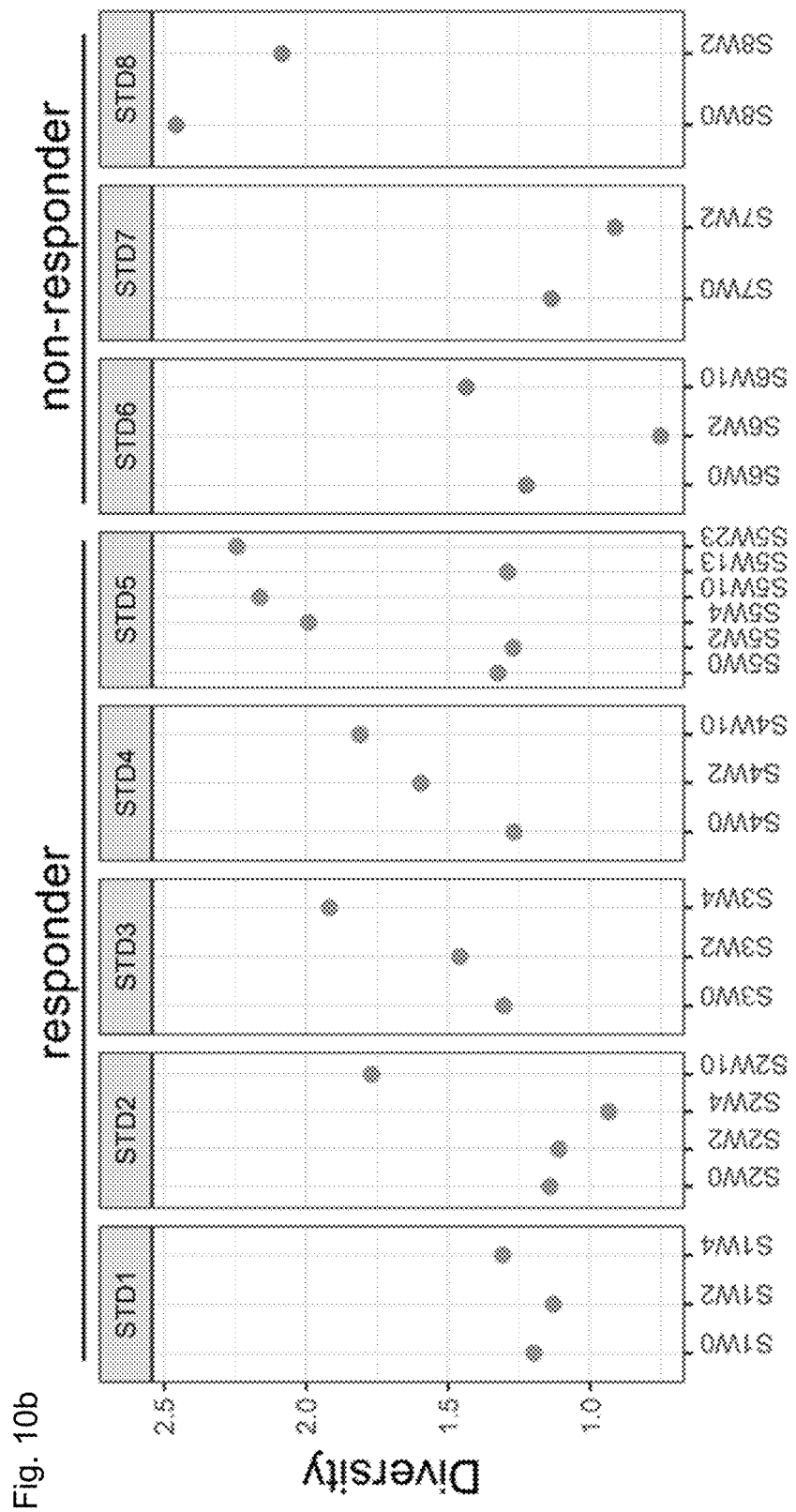

The effect of antibiotics on the gut mycobiota was also assessed across longitudinal time-points in 8 CDI subjects treated with vancomycin (STD treatment, FIG. 6, Table 1). Five of the eight subjects remained symptom-free with a negative stool *C. difficile* toxin at the last follow-up (termed responders, STD1-STD5), while three developed recurrence of CDI (termed non-responders, STD6-STD8). Unlike FMT, vancomycin induced inconsistent alterations in the fungal richness and diversity during longitudinal follow-up (FIG. 9a, b). There was no significant difference in the fungal richness or diversity between STD responders and non-responders after FMT, although vancomycin resulted in a significant increase in bacterial diversity in responders after FMT (FIG. 10, Wilcoxon matched-pairs singed rank test, p=0.0198).

Figure 8A:
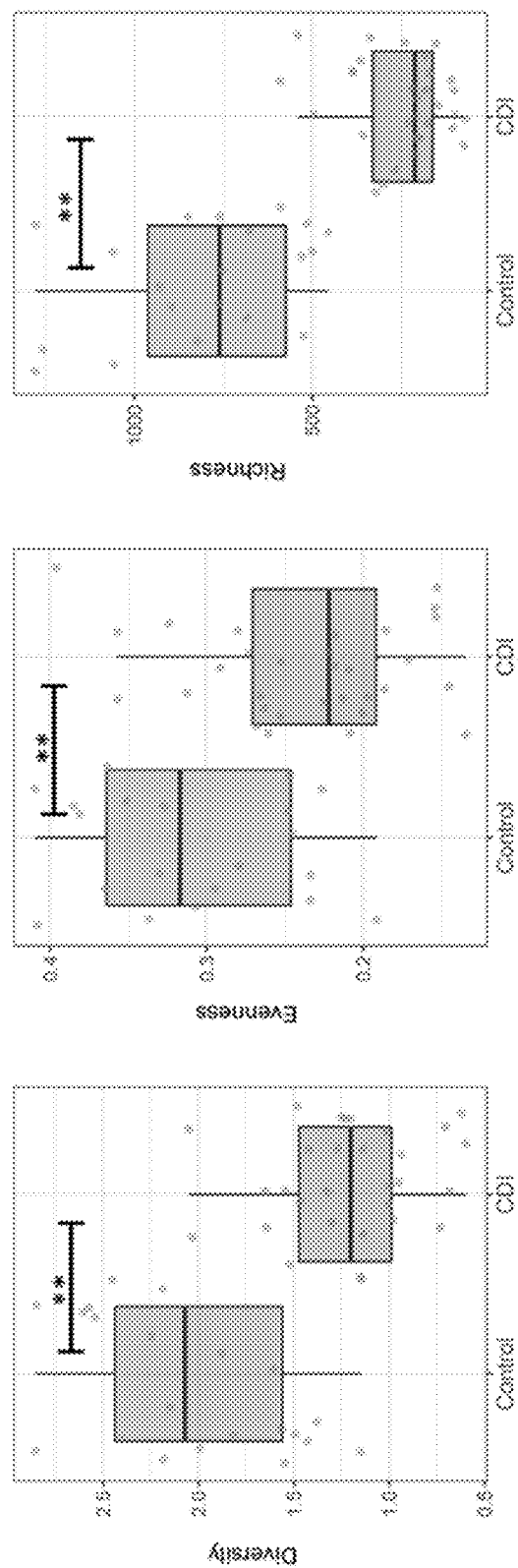
FIG. 8a-FIG. 8c Post-FMT alterations in the enteric bacterial microbiota of CDI recipients in association with FMT response.
Figure 8B:
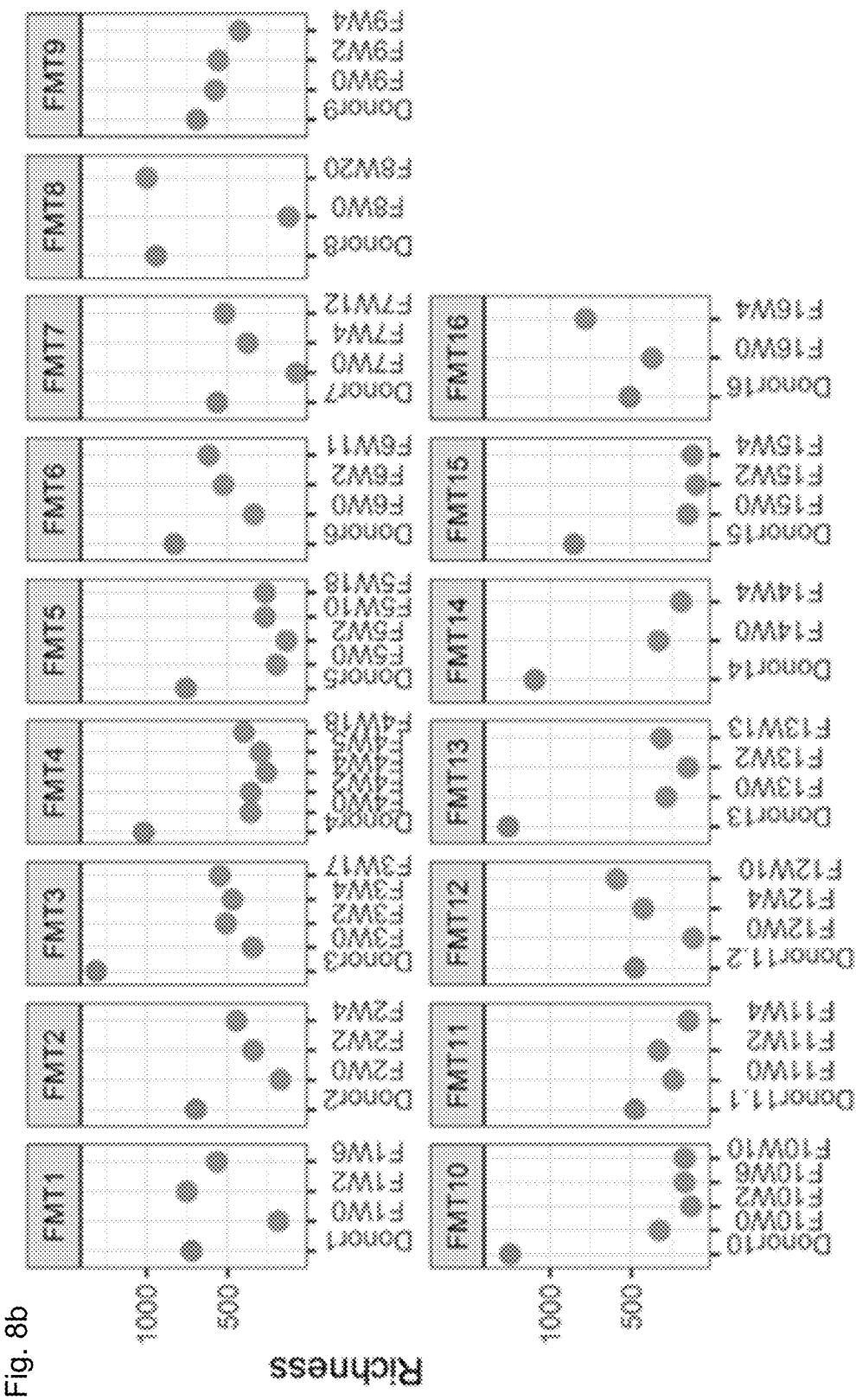
Figure 8B:
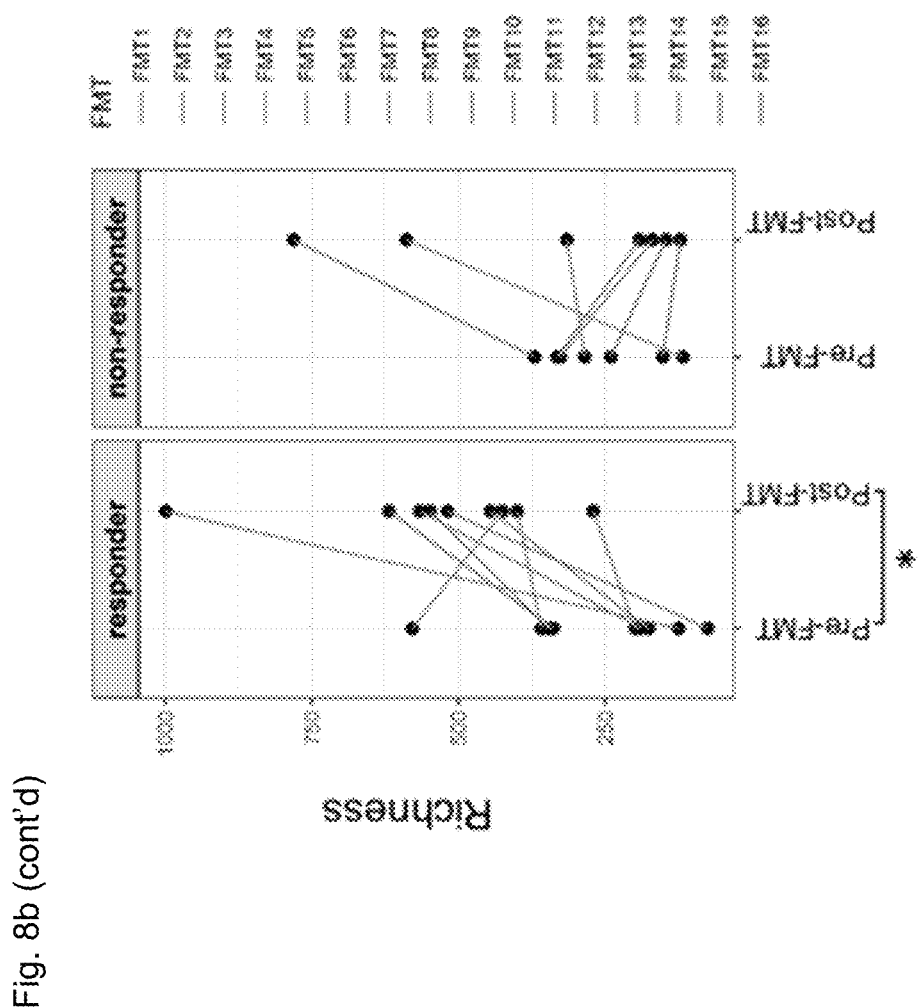
Figure 8C:
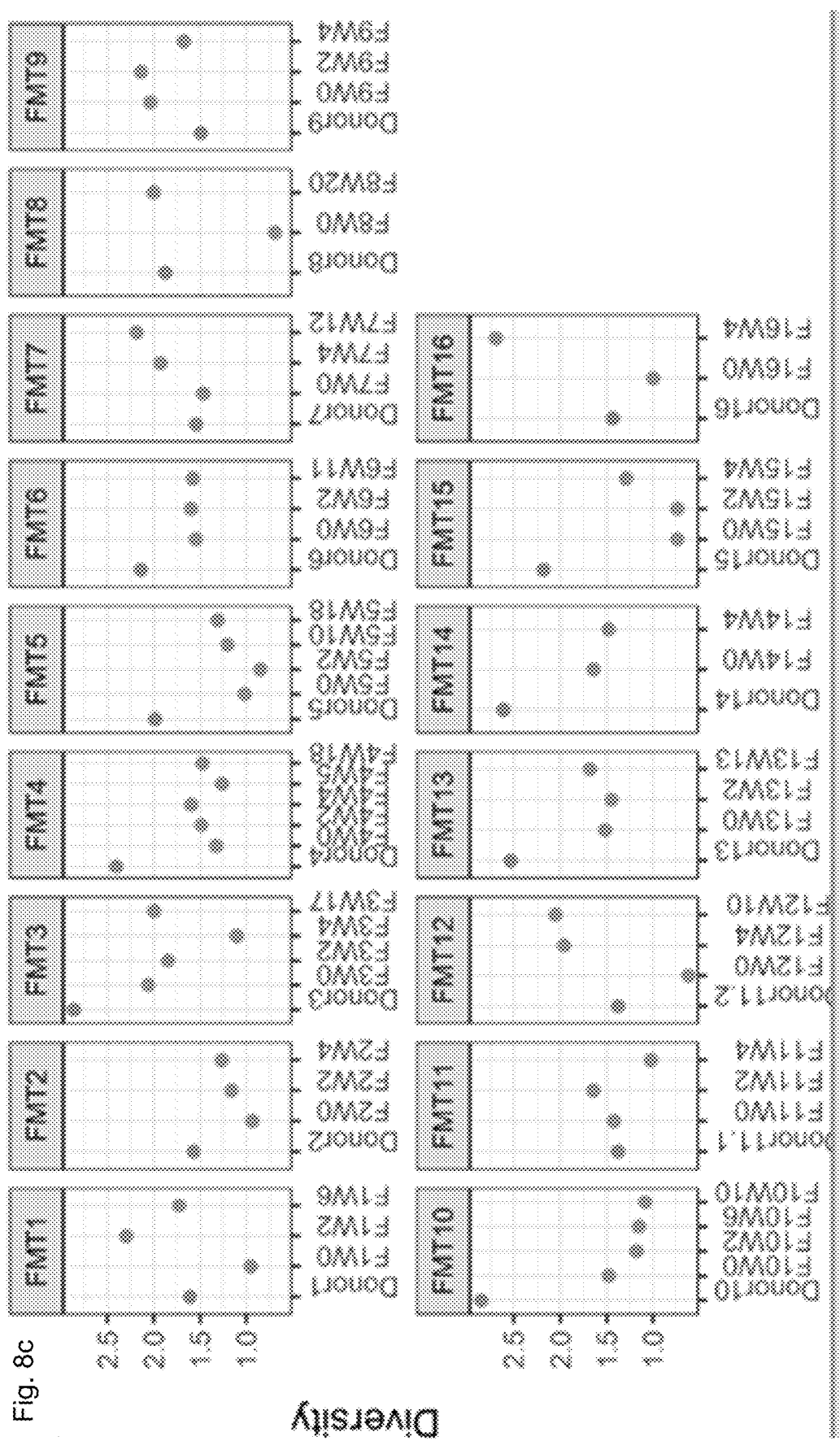
Figure 8C:
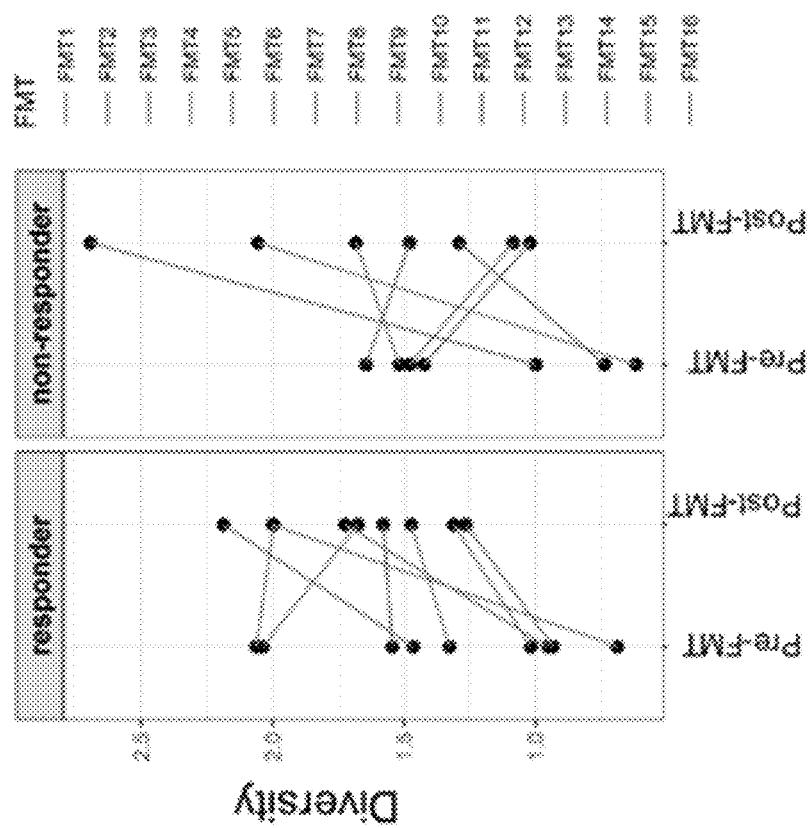

FMT and vancomycin led to an increase in the gut fungal diversity in 81.3% (13 out of 16) and 37.5% (3 out of 8) of CDI subjects, respectively (Chi-square test p=0.032, FIG. 8c), and an increase in the gut fungal richness in 68.8% (11 out of 16) and 37.5% (3 out of 8) of CDI subjects, respectively (FIG. 8c). FMT responders showed a significantly higher fold-change post FMT in both fungal richness and fungal diversity compared to STD responders (Mann-Whitney test p=0.019 and Chi-square test p=0.05 respectively, FIG. 8d, e). Collectively, these data indicate that FMT may be more influential in orchestrating the gut mycobiota than antibiotics.

Figure 11:
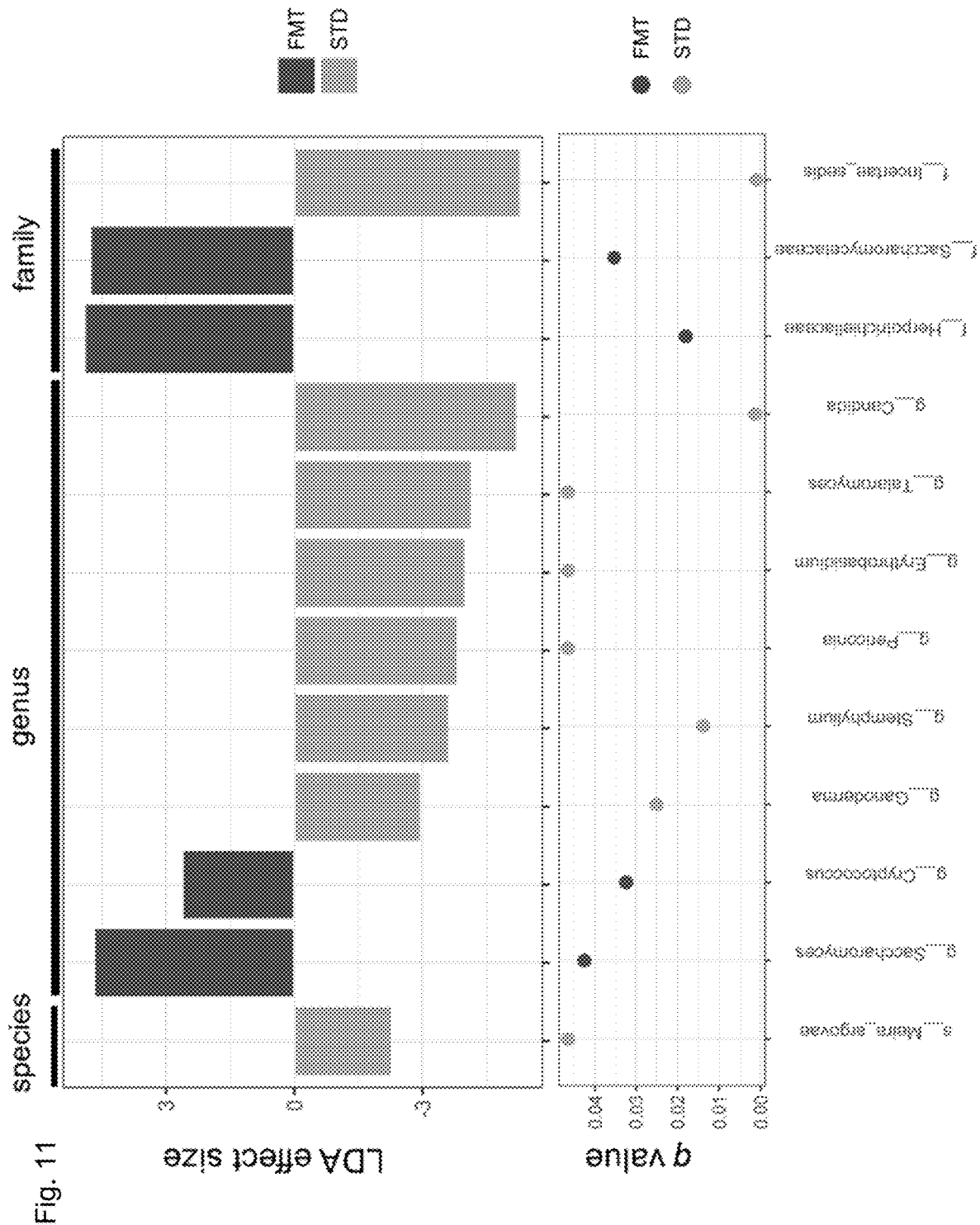
FIG. 11 Differentially enriched fungal taxa across post-treatment samples of FMT responders versus STD responders at the family, genus and species levels. Statistical significance level was determined by lefSe analysis with FDR correction (only those taxa with q values <0.05 and LDA effect size >2 are shown).
Figure 12:
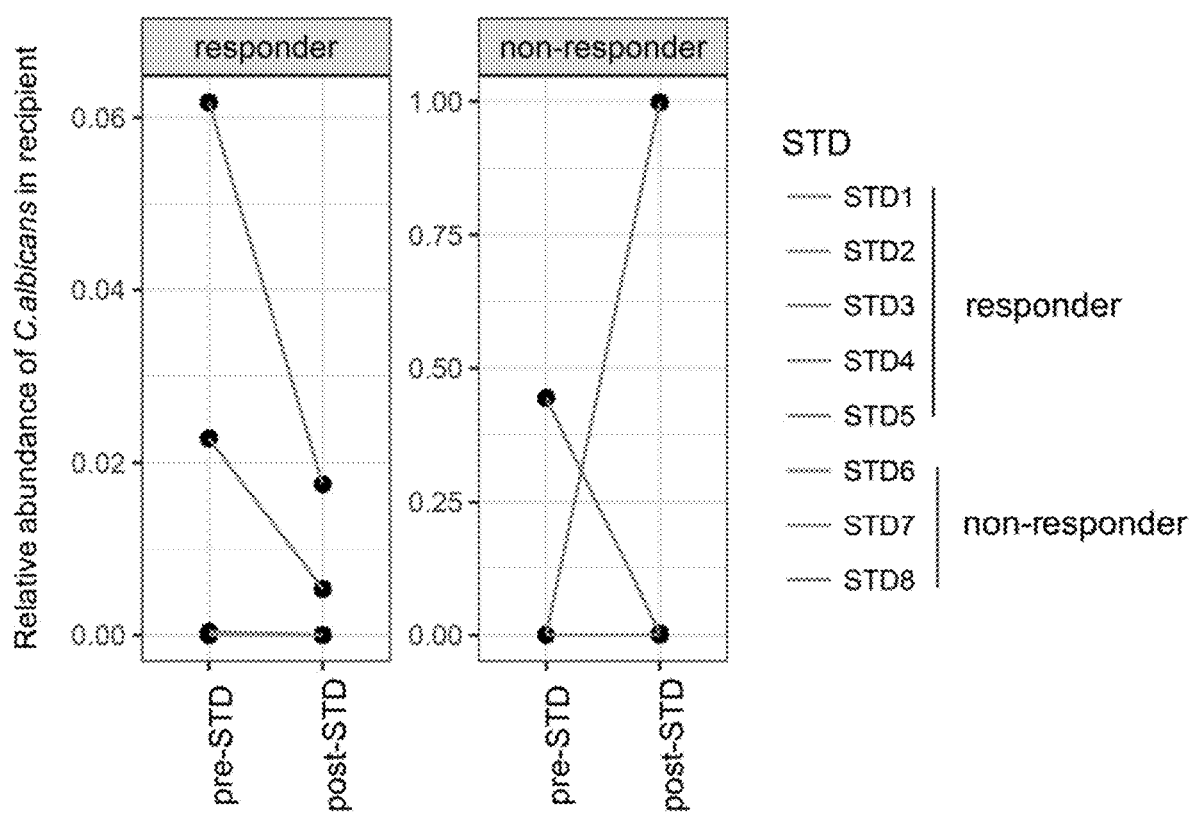
FIG. 12 Post-STD alterations of the relative abundance of fecal C. albicans at the last follow-up and at baseline in CDI subjects on vancomycin treatment. Statistical significance was determined by paired Wilcox signed rank test.

Taxonomical analysis was performed to further elaborate the effect of antibiotics on the fungal community and to discern differences between FMT and antibiotics in modulating the gut mycobiota. After vancomycin treatment, fungal compositions exhibited similar configurations during follow-up across STD subjects, with a marked expansion of the genus *Candida* (FIG. 8f). To define differentially enriched fungal taxa between subjects who responded to FMT and vancomycin, we implemented LefSe analysis across all follow-up samples of treatment responders. FMT treatment enriched the genera *Saccharomyces* and *Cryptococcus* in those who responded, whereas vancomycin disparately enriched a panel of fungal genera in STD responders after treatment, which included *Candida*, *Talaromyces*,

*Erythrobasidium, Periconia, Stemphylium, Ganoderma* (FIG. 11). At the family level, FMT caused an enrichment of Saccharomycetacean and Herpotrichiellaceae, while vancomycin caused an enrichment of Intertae sedis (FIG. 11). There was no statistically significant difference in the relative abundance of *C. albicans* between STD responders and non-responders, however a decrease in *C. albicans* was seen in STD responders after vancomycin treatment (FIG. 12). Subject STD7 who had a post-STD relative abundance of *C. albicans* >10% developed CDI recurrence after vancomycin treatment, further substantiating the importance of alleviation of *C. albicans* for eradicating CDI.

Figure 13:
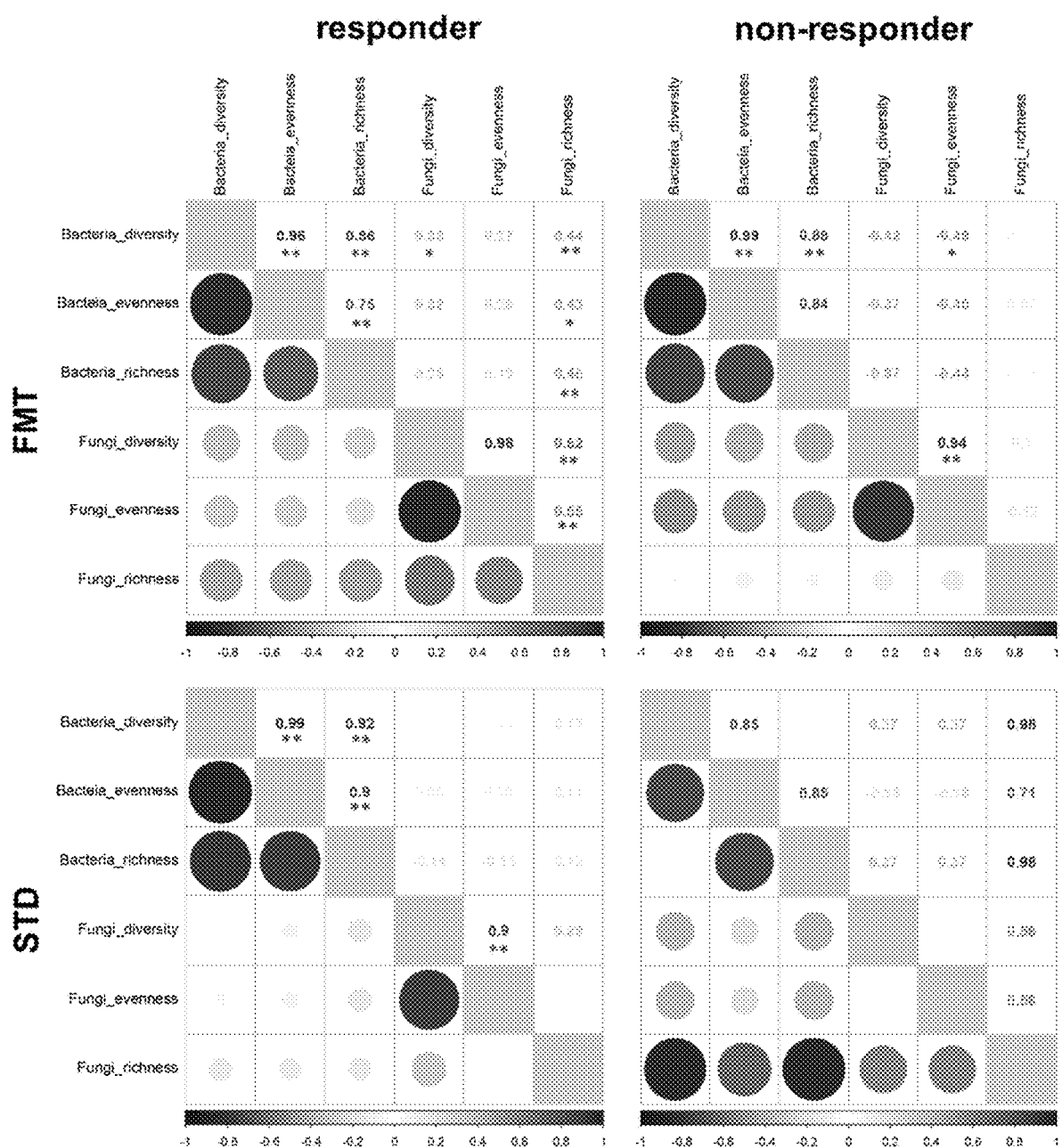
FIG. 13 Spearman correlation between fungal diversity, evenness, richness and bacterial diversity, evenness, richness, with respect to FMT and STD treatment and treatment response. Statistical significance was determined for all pairwise comparisons; significant correlations (P value <0.05) are displayed with asterisk. Blue circles and positive values indicate positive correlations, red circles and negative values indicate inverse correlations. The size and shading indicate the magnitude of the correlation where darker shades are more intensively correlated than lighter ones.
Figure 14:
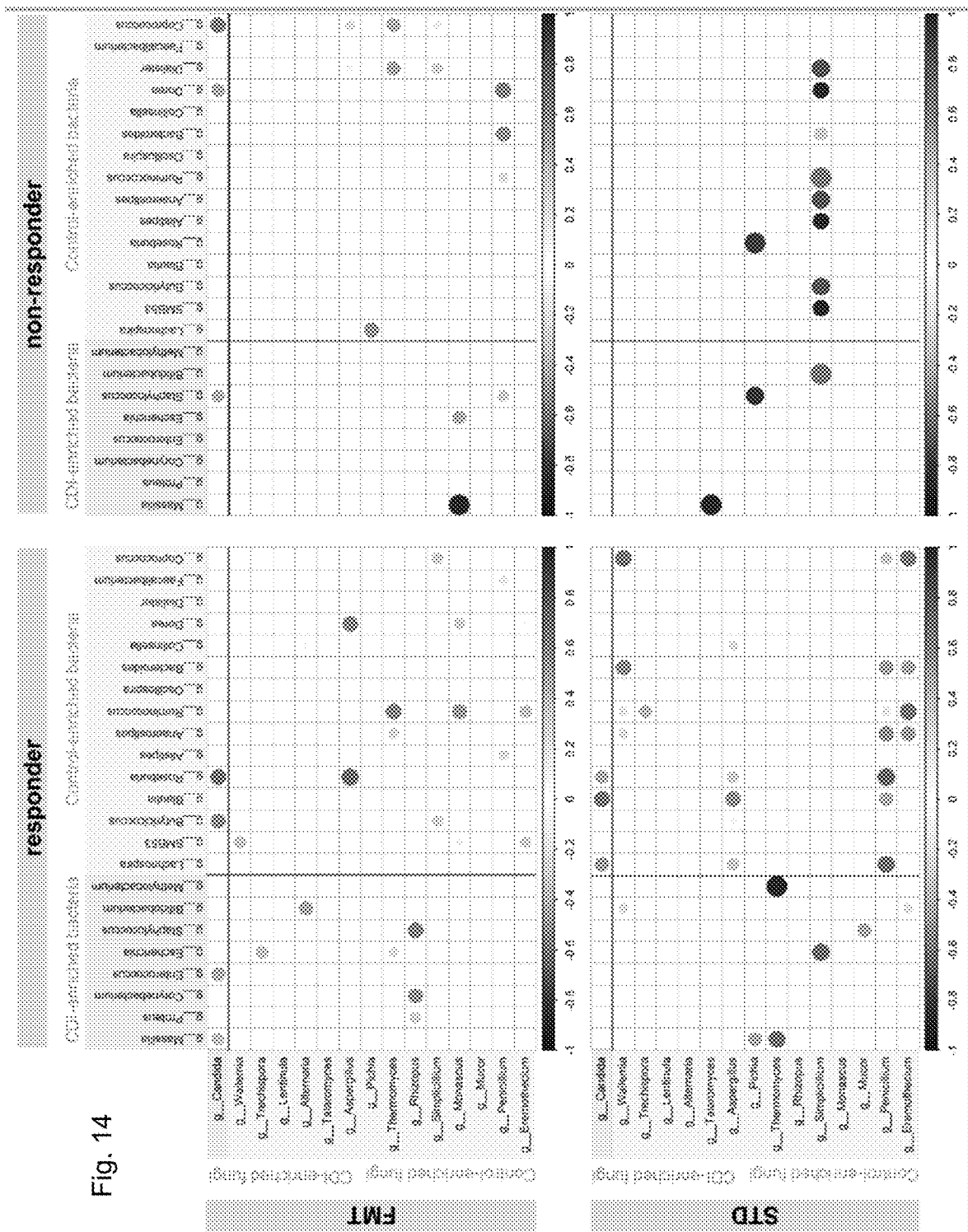
FIG. 14 Trans-kingdom interactions between bacteria and fungi. Spearman correlation plots of the relative abundance of fungal genera and bacterial genera identified to be significantly associated with CDI and controls at baseline, with respect to FMT and STD treatment and treatment response. Spearman correlation coefficients were calculated for all pairwise comparisons; Blue circles and positive values indicate positive correlations, red circles and negative values indicate inverse correlations. The size and shading indicate the magnitude of the correlation where darker shades are more intensively correlated than lighter ones. Statistical significance was determined for all pairwise comparisons; only correlations tested significant (P value <0.05) are displayed.

Trans-Kingdom Interactions Between Gut Mycobiota and Bacterial Microbiota are Associated with Treatment Outcome To characterize the ecological network of the gut mycobiota and bacterial microbiota, the correlation of the α-diversity (diversity, evenness and richness) of the fungal community with that of the bacterial community was evaluated. Among the post-treatment samples of FMT responders, significant positive correlations were found between fungal diversity and bacterial diversity, and between fungal richness and bacterial diversity, evenness, and richness (Spearman's correlation, permutation test, $P<0.05$, FIG. 13). In the post-treatment samples of FMT non-responders and STD responders, the correlation between bacterial and fungal communities showed a depletion of correlations between fungal richness and other bacterial and fungal a diversity indexes. The correlations were completely abolished across the post-treatment samples of STD non-responders. The correlations of fungal genera with bacterial genera were further assessed in controls and CDI subjects in association with treatment response. Significant inverse correlations between control-enriched bacteria, including butyrate-producing *Roseburia*, and CDI-enriched *Candida* were observed in FMT responders and STD responders after treatment, paralleling a prevalence of positive correlations between control-enriched bacteria and control-enriched fungi among which correlation of *Roseburia* and *Aspergillus* was present in both FMT responders and STD responders (FIG. 14). However, those who did not respond to either FMT or STD displayed an apparent contraction in the number of fungal-bacterial correlations after treatment, compared to FMT responders and STD responders. These data suggest the importance of restoration of an intricate and homeostatic fungal-bacterial ecosystem in maintaining treatment response.

C. albicans Compromises FMT Efficacy in a Murine Model of CDI

Figure 4B:
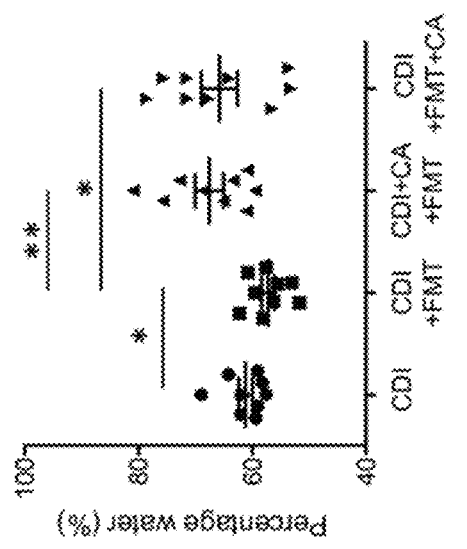
FIG. 4a-FIG. 4e *C. albicans* compromises FMT efficacy in eradicating *C. difficile* infection in mice.
Figure 4A:
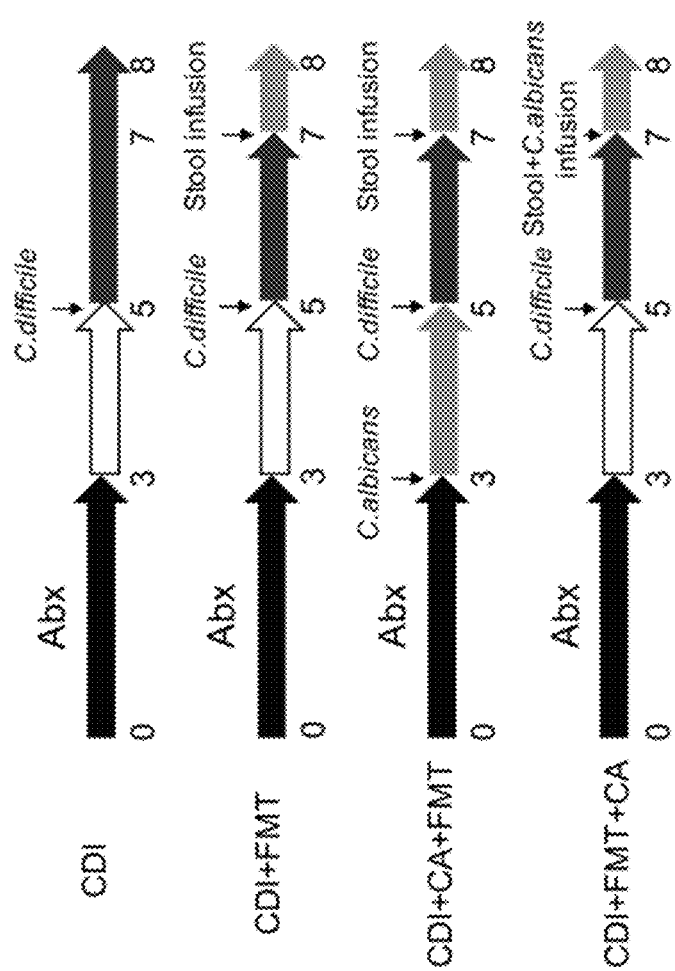
Figure 4C:
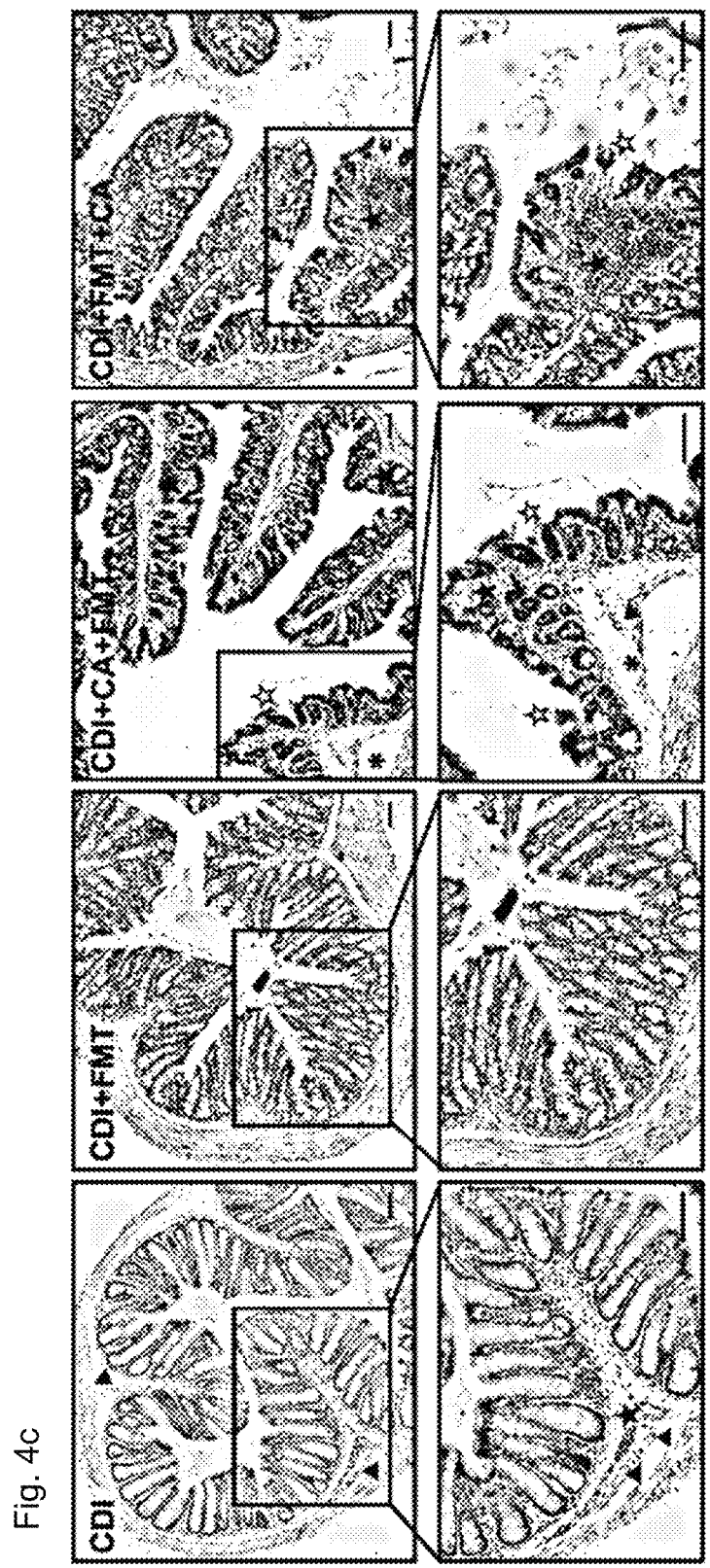
Figures 4D, 4E:
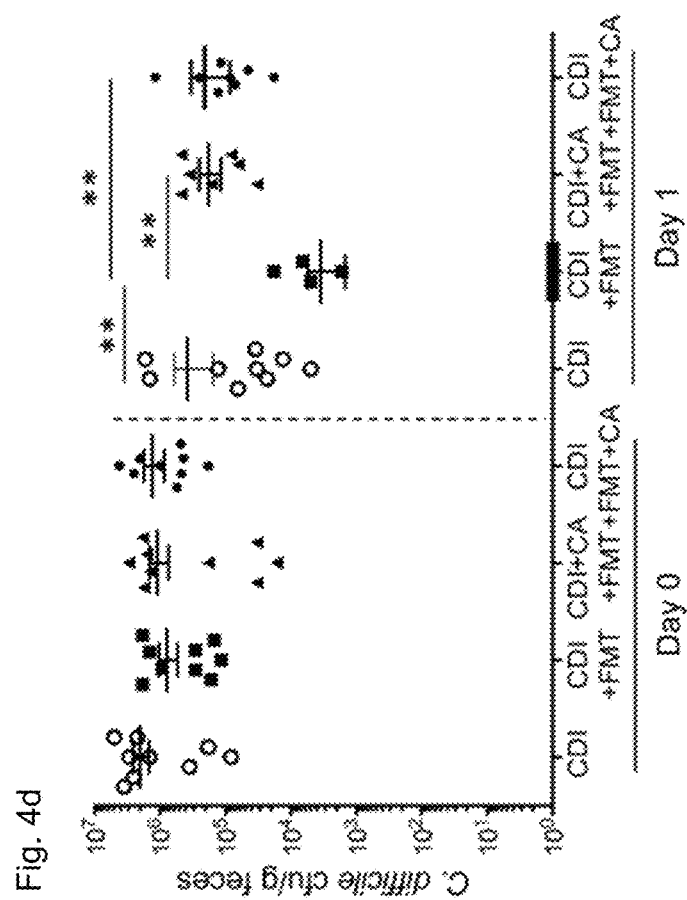

*C. albicans* was the most prominent species associated with treatment failure of FMT in CDI, suggesting a possible causal relationship. This assumption is further supported by reports whereby CDI recurrence was observed after antibiotics treatment [3,19], as antibiotics contribute to the expansion of *Candida*. To determine the causal relationship between *C. albicans* and response to FMT, the efficacy of FMT in eliminating *C. difficile* was assessed using a *C. difficile* induced-diarrhea murine model in three groups of mice: (i) mice infused with human stool preparation, (ii) mice colonized with *C. albicans* then infused with human stool preparation, and (iii) mice infused with human stool preparation supplemented with *C. albicans* during fecal transplantation (FIG. 4a). FMT was effective in ameliorating diarrhea, intestinal inflammation, and decreasing *C. difficile* burden, compared to CDI group, while no difference in *C. difficile* load was observed among all groups before FMT (FIG. 4b-d). However, mice that was colonized with *C. albicans* prior to FMT or those infused with donor stool supplemented with *C. albicans* suffered significant diarrhea, intestinal inflammation, and augmented *C. difficile* burden post FMT, when compared with mice administered with a single infusion of human stool (FIG. 4b-d). There were high levels of *C. albicans* in these recipient mice on day 1 post FMT, though a decrease in *C. albicans* load was observed after FMT in mice colonized with *C. albicans* prior to FMT (FIG. 4e). An anti-fungal agent, fluconazole, to eradicate *C. albicans* in a group of recipient mice prior to human stool infusion (FMT) (FIG. 15a). *C. difficile* load was then compared after human stool infusion between mice with and without anti-fungal treatment. Anti-fungal treatment in recipient mice colonized with *C. albicans* before human stool infusion restored the efficacy of FMT in clearing *C. difficile* infection (FIG. 15b). These data demonstrate that the existence of *C. albicans*, either in the recipient or in the donor, negates the efficacy of FMT in clearing *C. difficile*, while antifungal treatment reestablishes its efficacy. These results highlight that persistent fungal dysbiosis with aberrant presence of *C. albicans* can confer an unfavourable FMT outcome in CDI.

Total Fungal Load is Increased in CDI

Figure 17:
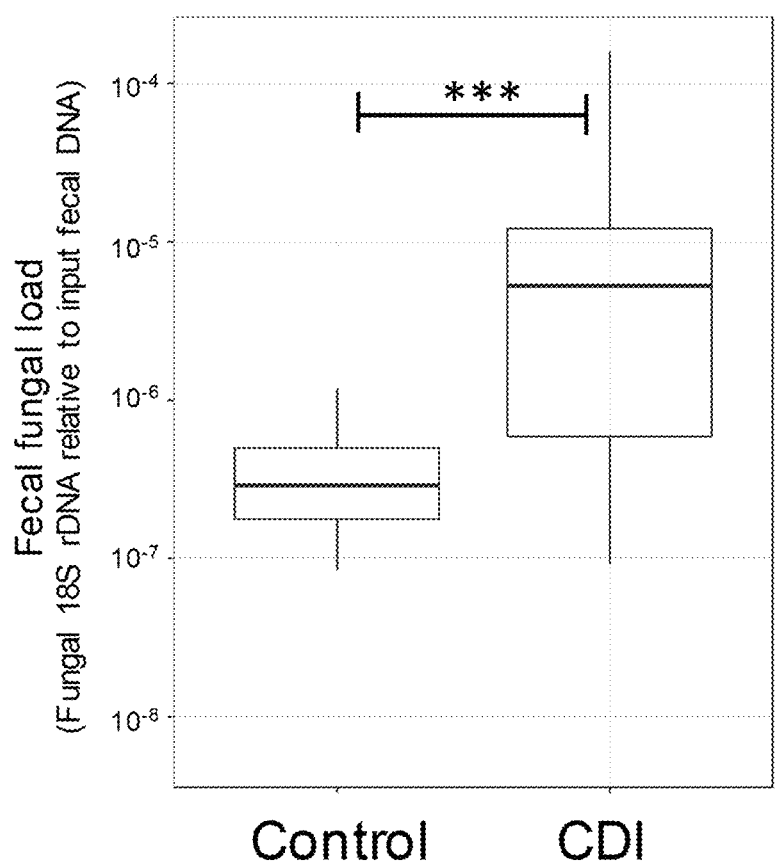
FIG. 17 Comparison of the total fungal load in the feces of controls and CDI subjects. Statistical significance was determined by Mann-Whitney test, ***P<0.001.

The total fecal fungal load was significantly higher in CDI than in controls [Mann-Whitney test, $p=0.0004$, $Log_{10}$ transformed effect size 1.32 (95% CI: 0.62-1.97), FIG. 17].

Total Fungal Load and *C. albicans* in Inflammatory Bowel Disease (IBD)

Figure 18B:
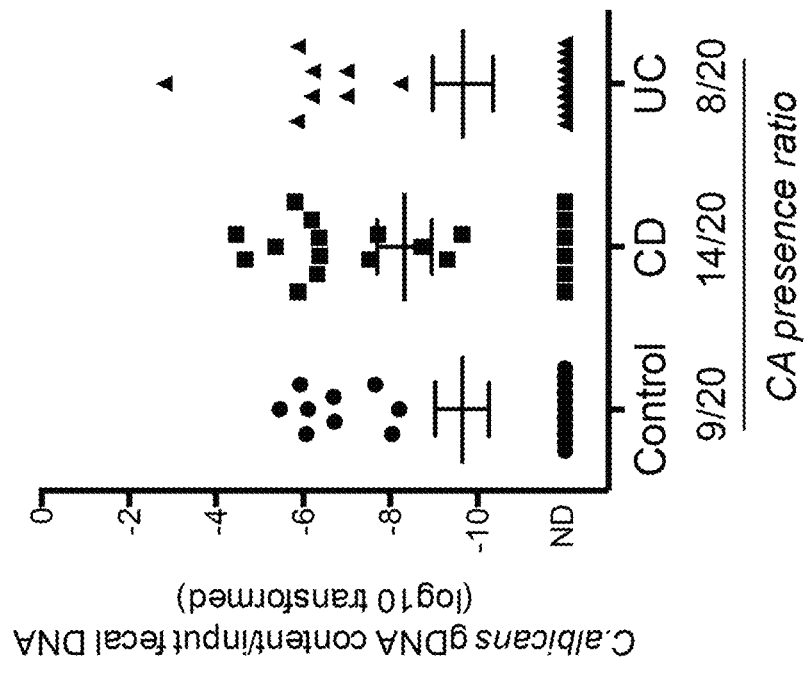
FIG. 18a-FIG. 18b The total fecal fungal load and C. albicans in inflammatory bowel disease (IBD).
Figure 18A:
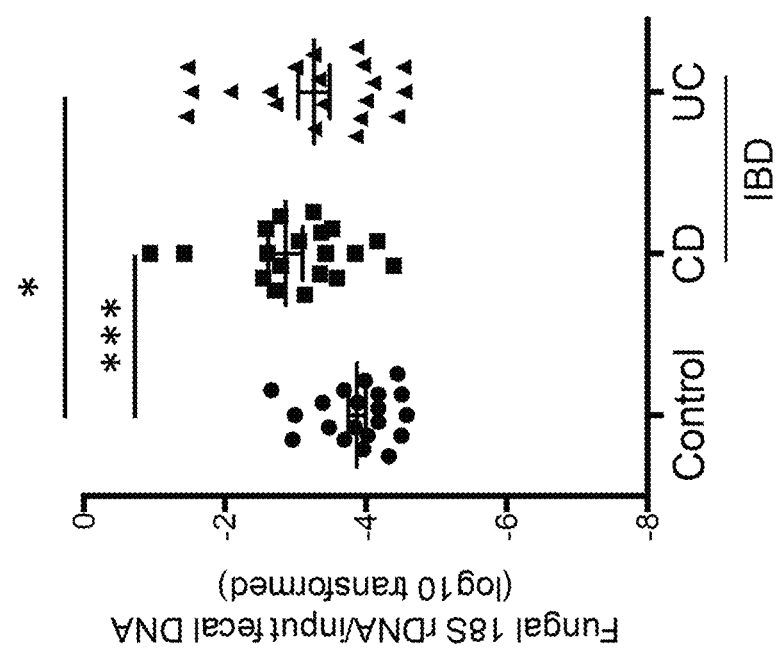

The total fecal fungal load was significantly higher in patients with IBD, including patients with Crohn's disease (CD) and Ulcerative colitis (UC)—two subtypes of IBD, than in controls (Mann-Whitney test, $p=0.0003$, $p=0.0225$, respectively, FIG. 18 a). The fecal presence ratio of *C. albicans* is higher in CD than in controls, and 3 CD patients exhibiting the highest *C. albicans* levels had a history of recent exposure to antibiotics (FIG. 18 b).

Total Fungal Load is Increased in Irritable Bowel Syndrome (IBS)

Figure 19:
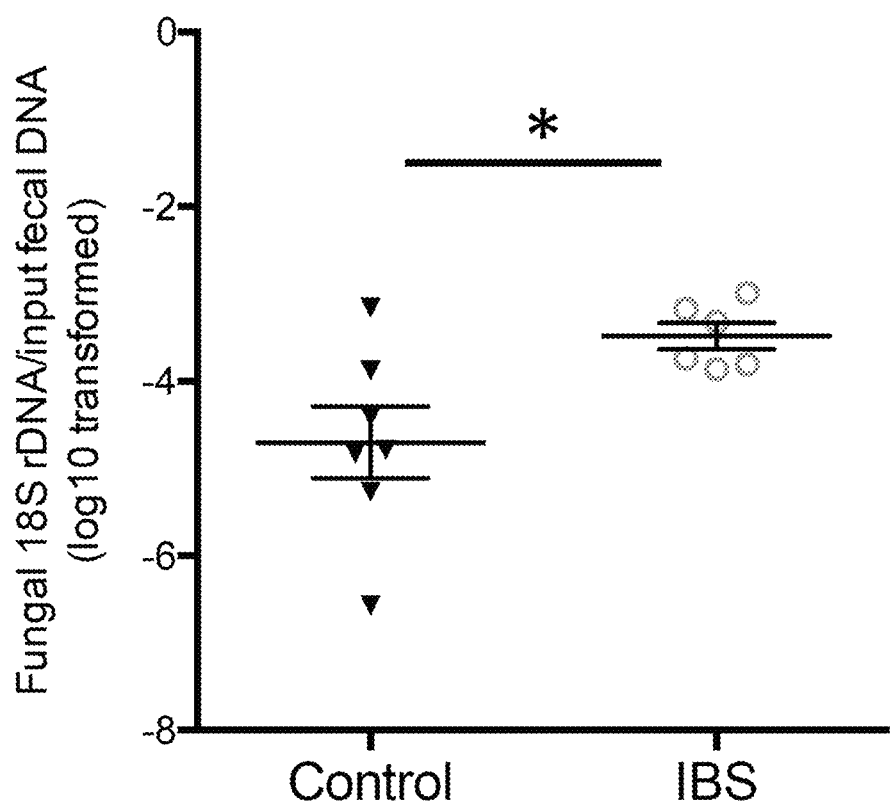
FIG. 19 The total fecal fungal load in irritable bowel syndrome (IBS). Comparison of the total fungal load in the feces of controls and IBS subjects. Statistical significance was determined by Mann-Whitney test, *P<0.001, P<0.05.
Figure 20A:
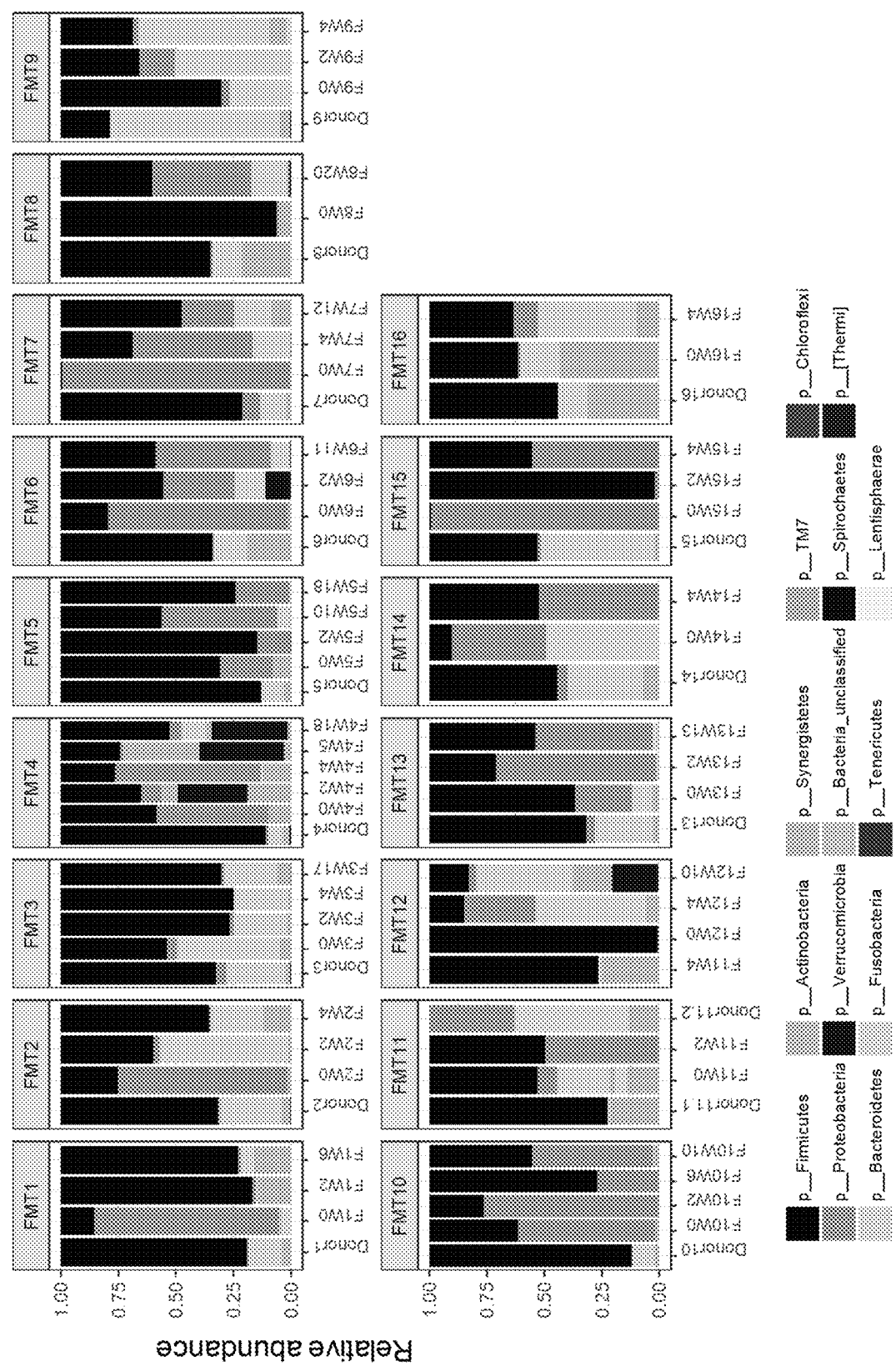
FIG. 20a-FIG. 20d Post-FMT alterations in the taxonomic composition of the bacterial microbiota of CDI recipients in association with FMT response. Bacterial configurations in FMT recipients over the course of longitudinal follow-up and in their corresponding donors at baseline, at the phylum (FIG. 20a) and family (FIG. 20b) levels.
Figure 20B:
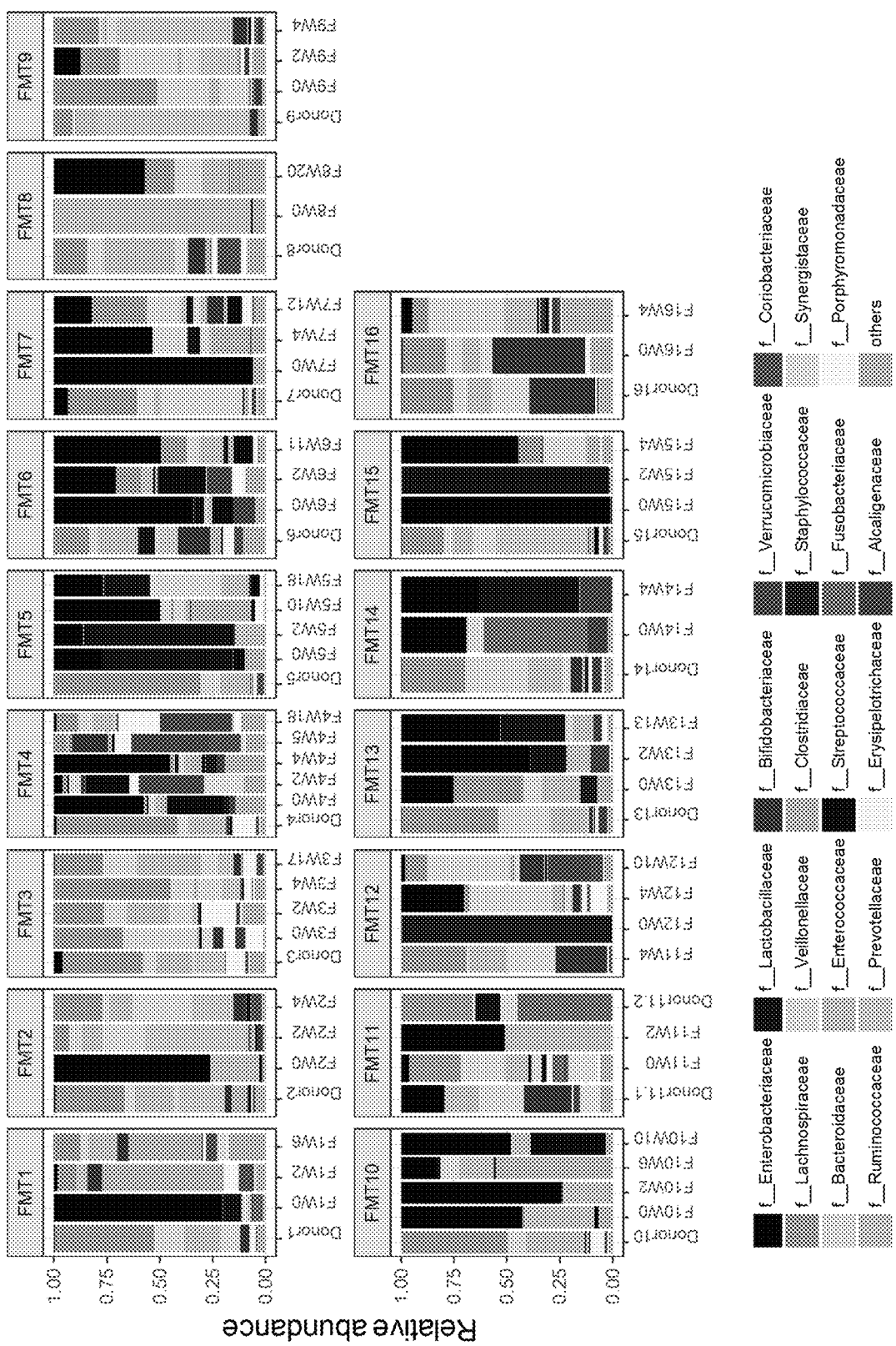
Figure 20C:
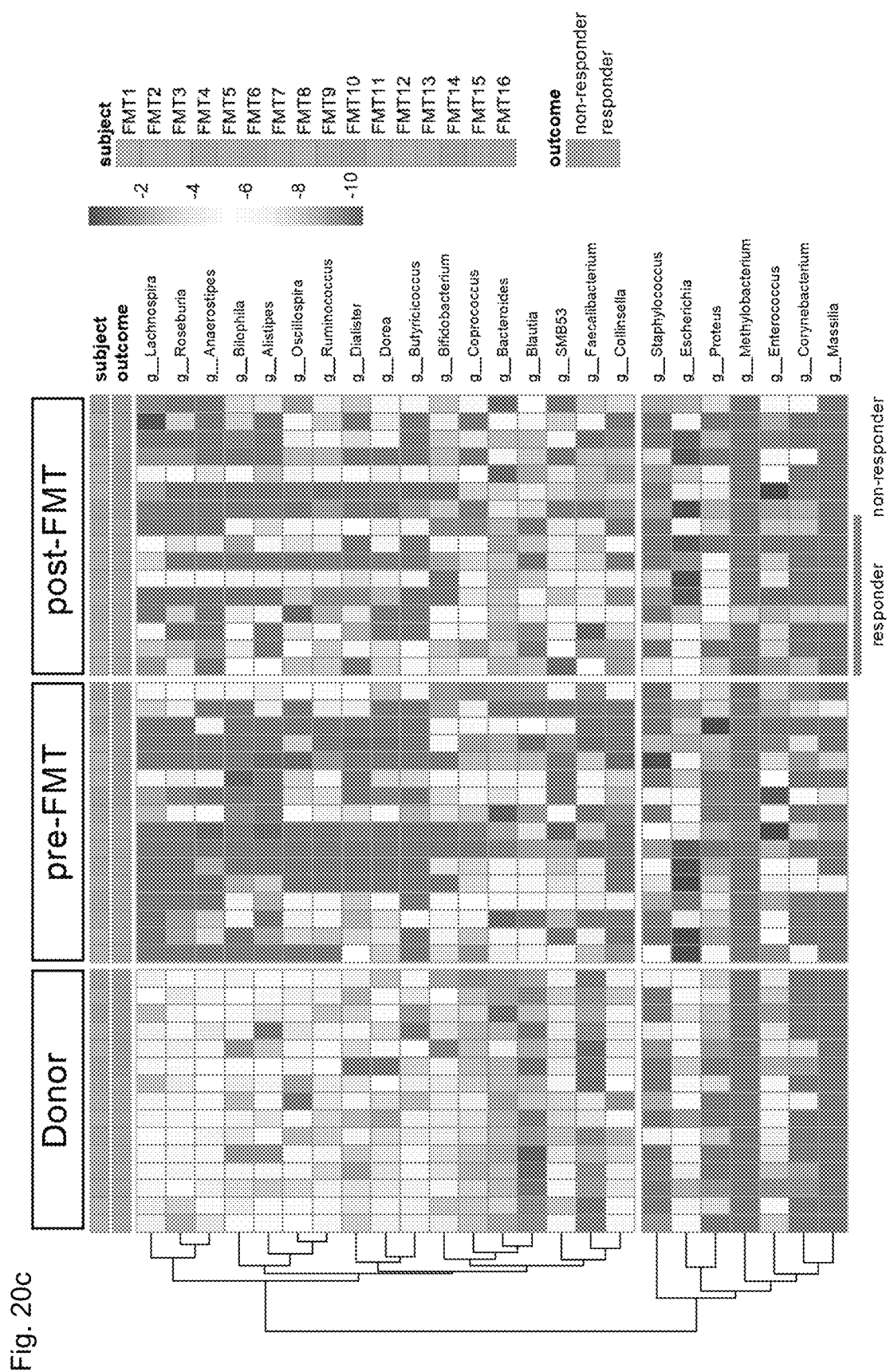
Figure 20D:
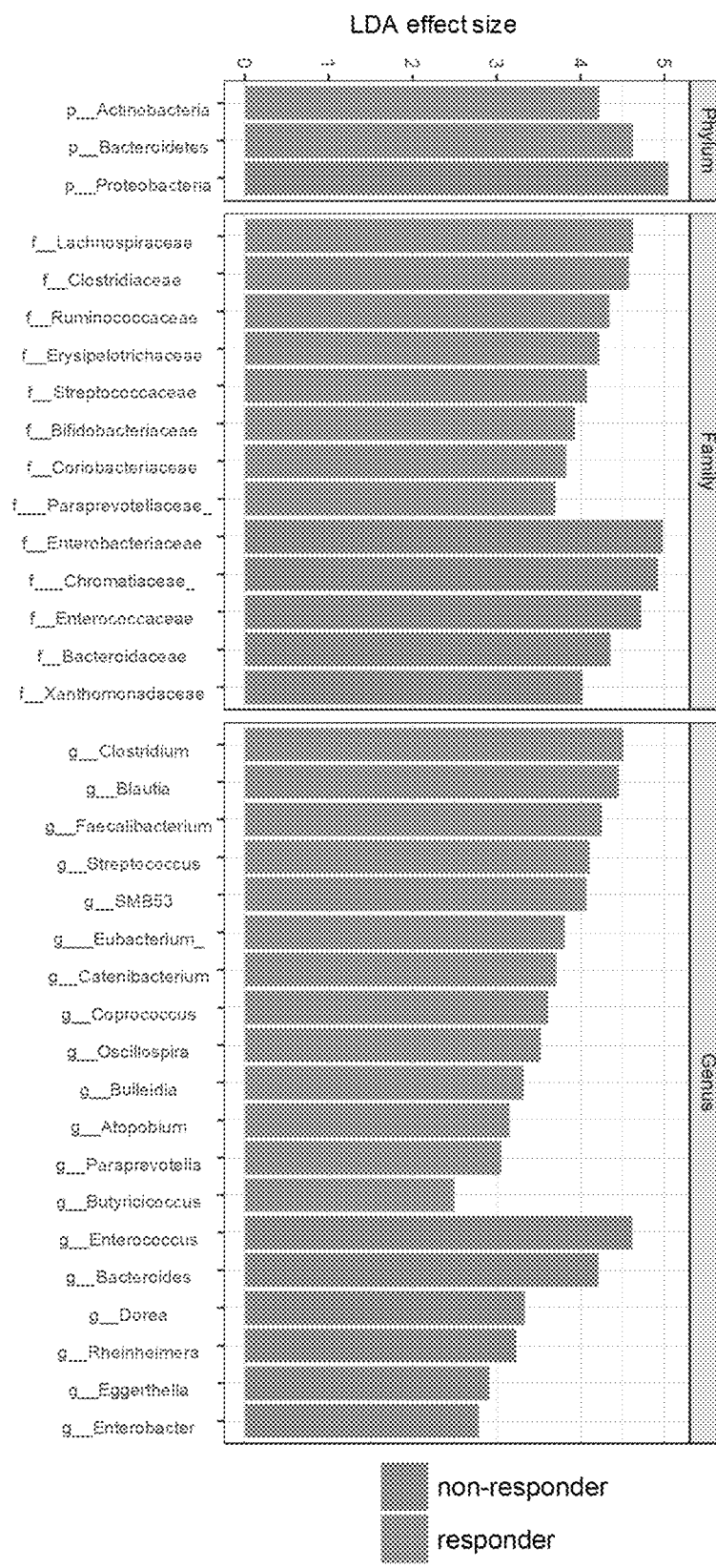

The total fecal fungal load was significantly higher in IBS than in controls [Mann-Whitney test, $p=0.0237$, FIG. 19].

Bacterial Alterations in CDI after FMT in Association with FMT Outcome

The present inventors explored the composition of the bacterial microbiota after FMT in relation to FMT outcomes, at various taxonomic levels (FIG. 20). Actinobacteria, Bacteroidetes (phylum-level taxa), Lachnospiraceae, Clostridiaceae, and Ruminococcaceae (family-level taxa), *Clostridium*, *Blautia*, and *Faecalibacterium* (genus-level taxa) were significantly more enriched in FMT responders than in non-responders after FMT. However, bacteria from the phylum Proteobacteria were more abundant in FMT non-responders relative to FMT responders. FMT responders displayed bacterial abundances resembling that of the donor, whereas FMT non-responders showed inadequate relative abundances of donor-enriched bacteria at the last follow-up after FMT (FIG. 20c). LefSe analysis on the fecal bacteriomes of donors at the genus level identified *Escherichia* and *Proteus* as the differentially enriched genera in FMT responders' donor stool and in FMT non-responders' donor stool respectively (LDA effect size 2.58 and 2.35, FDR adjusted $q=0.017$ and 0.006, respectively).

Discussion

This is the first study to characterize the gut mycobiota in CDI and to elucidate mycobiota alterations after FMT in relation to treatment outcome. Patients with CDI showed enteric fungal dysbiosis. Importantly, disease recurrence after FMT was associated with several important findings including persistent fungal dysbiosis, low levels of donor-derived fungal colonization, high abundance of *C. albicans* in the recipient stool before FMT and the presence of *C. albicans* in the donor stool. The observations that disease cure requires both fungal and bacterial colonization from the donor provides new and important insights into the potential therapeutic importance of the gut mycobiota in treatment outcome in FMT, beyond the bacterial microbiota. These data also highlight a new concept in FMT that the abundance of fecal *C. albicans* both in recipient before treatment and in donor are critical components when considering implementation of FMT. Integration of more in-depth mycobiota analysis in donor-recipient pair may lead to personalized and targeted gut microbial therapy in the future.

Although studies of the gut mycobiota have lagged behind that of the gut bacterial microbiota, fungi are increasingly being considered as important players of the gut and interactions between pathogenic and commensal fungal and bacterial communities are crucial in the maintenance of human health and disease pathogenesis[16]. Furthermore, disruption of the gut mycobiota has deleterious effect on host immunity [17]. Despite high interpersonal variability of the gut mycobiota in patients with CDI, there was a significant expansion of the genus *Candida* and the species *C. albicans*. Interestingly, FMT induced an increase in the genus *Saccharomyces* along with a marked contraction of *Candida* and *C. albicans* after FMT in treatment responders, while recipients who demonstrated high abundance of *C. albicans* in the stool after FMT (10%) or those whose donor had a high abundance of (0.1%) of *C. albicans* were more likely to have disease recurrence after FMT. Over-presentation of *C. albicans* in the recipient stool after FMT may largely contribute to treatment failure.

The role of fungal commensals in educating the human immune system has gained new appreciation in intestinal disease. In the steady state, bacterial communities keep fungi in check in the gut. Fungi are major causes of infections among immunocompromised or hospitalized patients with serious underlying diseases and comorbidities. *Candida* species remain the most important cause of opportunistic infections worldwide, affecting predominantly elderly patients [20]. Candidalysin was recently unveiled as a fungal toxin from *C. albicans* critical for mucosal infection [21]. Commensal bacteria inhibit *C. albicans* colonization through activation of HIF-1α and LL-37 [22]. Antibiotic treatment selectively and effectively eradicates the bacterial community but consequently leads to fungal outgrowth, particularly the *Candida* species [23,24]. Antibiotics or immunosuppressants are effective in the short term but they likely compromise the immune system in the longer term. A compromised immune system creates a more favourable environment to expansion of *Candida* and overgrowth of *Candida* can alter the recovery of the gut bacterial microbiota after cessation of antibiotic treatment [25,26]. In this study, the over-presence of *Candida* species in recipients might account for the high failure rate of FMT in CDI. In DSS-induced colitis mouse model as well as patients with inflammatory bowel disease (IBD), *C. albicans* and *Candida* were significantly enriched [27-29]. Antifungal treatment decreased *Candida* prevalence and ameliorated inflammatory responses in DSS colitis mice [29]. However, disruption of fungal communities by long-term use of antifungals aggravated severity of DSS colitis and allergic airway [30]. Collectively, these data implicate the importance of the gut fungal-bacterial homeostasis in host health. These data suggest that the establishment of a balanced gut fungal and bacterial community via FMT is important to eradicate CDI, as FMT non-responders showed abrogated fungi-bacteria correlations in α-diversity and taxa when compared with responders.

In conclusion, gut mycobiota alterations may determine treatment outcome in FMT. The persistence of fungal dysbiosis, particularly the presence of *C. albicans*, can incur CDI recurrence. The findings disclosed herein highlight the importance of both "optimal" donor selection and pre-FMT eradication of *C. albicans* in recipient during FMT practice, where future FMT therapy should incorporate detailed characterization and stratification of both donor and recipient fecal mycobiomes. These results provide a framework for future investigations into the contribution of donor/recipient mycobiota profiles and gut fungi-bacteria interactions in FMT treatment for various human diseases.

Methods

Study Subjects and Treatment Outcome

The current study was a sub-study from a randomised controlled trial (RCT) of FMT versus vancomycin (standard therapy, STD) for patients with CDI. Consecutive CDI subjects enrolled into this randomised controlled trial were invited to participate in a substudy of assessment of fecal microbiota. Patients were included if they had three or more loose or watery stools per day for at least two consecutive days or eight or more soft or loose stools in 48 hours and a positive stool test for *C. difficile* based on a two-step testing algorithm in our hospital, a positive GDH (Glutamate dehydrogenase) screening test followed by a positive polymerase chain reaction (PCR) test of *C. difficile*. A total of 31 subjects with CDI and 24 healthy household controls were recruited and stool samples at baseline were obtained for analyses of fungal and bacterial microbiomes. Among them, 24 CDI subjects consented to have stool samples collected serially after treatment for microbiome analysis. 16 CDI subjects were treated with FMT and 8 were treated with vancomycin, and they were followed up at baseline and at weeks 2, 4, 10 and 16 after treatment (FIG. 6). Subjects in the FMT group received 5 days of vancomycin followed by donor infused stool via nasojejunal route and those who had STD received oral vancomycin 500 mg orally four times per day for 10 days. A computer-generated randomization schedule was used to assign patients to the treatment sequences. All patients kept a stool diary and were questioned about stool frequency and consistency and medication use.

Treatment response was defined as an absence of diarrhea or persistent diarrhea that could be explained by other causes with a negative stool test for *C. difficile* toxin, while relapse was defined as diarrhea with a positive stool test for *C. difficile* toxin. Treatment cure is defined as symptom resolution and a negative *Clostridium difficile* toxin in stool until the last follow-up (last follow-up is referred to as the last stool collection time point, as shown in FIG. 6). 9 of the 16 subjects who had FMT (FMT1-FMT9), and 5 of the 8 patients (STD1-STD5), who had vancomycin were cured of CDI (termed responders, Table 1) at a median follow-up of 16 weeks. CDI recipients FMT11 and FMT12 shared the same donor, and this donor was termed "Donor11". Clinical data of the subjects and collected stool samples are shown in Table 3. None of the patients had received antibiotics or proton pump inhibitors after FMT.

Study Design

Patient Inclusion Criteria:
1. *C. difficile* infection was defined as diarrhea (≥3 soft, loose or watery stools per day for at least 2 consecutive days or ≥8 soft or loose stools in 48 hours) and a positive stool test for *C. difficile* toxin; and
2. Age ≥18; and
3. Written informed consent obtained Patient Exclusion Criteria:
1. The presence of human immunodeficiency virus (HIV) infection with a CD4 count of less than 240
2. Pregnancy
3. GI Bleeding
4. Acute coronary syndrome Donor Screening:

Donors included individuals who are spouses or partners, first-degree relatives, other relatives, friends, and individuals unknown to the patient. They were screened with a questionnaire and excluded if they had taken antibiotics within the preceding 3 months; were on major immunosuppressive agents, including chemotherapeutic agents; had known or recent exposure to HIV, hepatitis B or C; had a current communicable disease; participated in high-risk sexual behaviors; used illicit drugs; traveled within 6 months to areas with endemic diarrheal illnesses; or had history of inflammatory bowel disease, irritable bowel syndrome or chronic diarrhea, gastrointestinal malignancy or polyposis. In addition, donor was screened for HBsurface Ag, Anti-HBc, Anti-HCV, Anti-HIV, Syphilis EIA, stool microscopy, culture and sensitivity, stool cyst, ova, parasite, norovirus and *C. difficile* (cytotoxin and PCR assay). All subjects and collected stool samples are listed in Table 1.

The donors for the FMT group were healthy household controls and the donor stool samples analyzed were the same samples used for FMT. All subjects provided written informed consent.

Family members provided donor stool for subjects randomised to FMT arm. Cure after FMT or vancomycin therapy was defined as symptom resolution and negative *Clostridium difficile* toxin in stool at last follow-up by PCR assay. Relapse was defined as diarrhea with a positive stool test for *C. difficile* toxin.

This was a randomised but not blinded study. However for mycobiome and bacterial microbiome analyses on stool samples, assessments were initially performed by analysts who were blinded to the clinical outcome of the studied subjects. When the profiled mycobiome and bacterial microbiome data were available for each individual subject, correlation was then made to associate microbiome profiles with treatment outcomes of subjects.

Infusion of Donor Stool

In subjects who received FMT, a nasoduodenal tube was inserted with radiology guidance. Donor feces was diluted with 500 ml of sterile saline (0.9%), blended and the supernatant was strained with filter paper and poured in a sterile bottle. Within 6 hours after collection of feces by the donor, the solution was infused through a nasoduodenal tube (2 to 3 minutes per 50 ml). The tube was removed 30 minutes after the infusion, and patients were monitored for 2 hours. In subjects with received FMT, a minimum of 50 g of donor stool was collected on the same day of infusion and used within 6 hours of collection.

Fecal DNA Extraction

Fecal DNA was isolated as described below. 100 mg fecal sample was pre-washed with 1 ml ddH$_2$O and pelleted by centrifugation at 10,000×g for 1 minute. The fecal pellet was re-suspended in 800 µl TE buffer (pH 7.5), supplemented with 1.6 µl 2-Mercaptoethanol and 500 U lyticase (Sigma), and incubated at 37° C. for 60 min. The sample was then centrifuged at 10,000×g for 2 minutes and fecal DNA was subsequently extracted from the pellet using ZR Fecal DNA miniPrep kit (Zymo Research, Orange, CA) according to the protocol. Briefly, fecal pellet was added to the BashingBeadLysis Tube with 750 µl Lysis solution, and then processed at maximum speed for 10 minutes. The lysates were centrifuged at ≥10,000×g for 1 minute. The supernatant was transferred to a Zymo-Spin™ IV Spin Filter in a collection tube and centrifuged at 7,000×g for 1 minute. About 1,200 µl of fecal DNA binding buffer was added to the filtrate in the collection tube, followed by concentration and purification in a new filter tube. Finally, a total of 50 µl eluted DNA with a concentration at 20-100 ng/µl was prepared for each sample.

Fungal ITS2 Sequencing and Quality Control

The final fecal DNA for fungal sequencing was amplified based upon ITS2 (Internal transcribed spacer 2) region using primers as below and PrimeSTAR HS DNA Polymerase kit (TaKaRa, Japan). The primer pairs are ITS2-F: 5'-GCATCGATGAAGAACGCAGC-3', ITS2-R: 5'-TCCTCCGCTTATTGATATGC-3' (SEQ ID NOs 1 and 2, respectively). ITS2 amplicons were generated with 38 cycles of 3-step PCR: 98° C. 10 s, 59° C. 10 s, and 72° C. 30 s. PCR samples were then sequenced on the Illumina MiSeq PE300 platform (2×300 bp, BGI, China), 151,524±97,694 (number±SD) clean sequences obtained on average (sequence statistics in Table 4).

Raw reads were filtered by SOAPnuke (v 1.5.3) (web site: soap.genomics.org.cn/) developed by BGI as follows: (i) adaptors removed, (ii) read removed if N base is more than 3% of the read, (iii) read removed if bases with quality low than 20 were more than 40% of read, (iv) all duplicates removed. Quality control and data analysis were further implemented in PIPITS (v 1.4.5) 31. Briefly, PIPITS_PREP prepares raw reads from Illumina MiSeq sequencers for ITS extraction; PIPITS_FUNITS extracts ITS2 from the reads; and PIPITS_PROCESS analyses the reads to produce operational taxonomic unit (OTU) abundance tables and the RDP taxonomic assignment table for downstream analysis. The quality trimmed and ITS2 extracted reads were aligned to fungi UNITE database exploiting RDP classifier 2.10 for taxonomic assignment to produce operational taxonomic unit (OTU) abundance table (based on sequence identity >97% identity) and phylotype abundance tables at different taxonomic levels, for downstream analysis.

The fungal OTU and phylptype abundance data were imported into R 3.2.3. Richness, diversity, and evenness calculation were performed using the estimated richness function of the phyloseq package. Spearman correlation and their significance were calculated using the cor and cor.test functions in R, respectively. For the fungal-bacterial taxa comparisons, Spearman correlations were calculated for the relative abundance of the differentially presented fungal taxa and the bacterial taxa determined to be significantly associated with disease by Lefse analysis. Correlation plots were generated using the corrplot package in R. Heat maps were generated using the pheatmap package in R.

Quantitative PCR for Detection of *C. albicans* in Human Fecal DNA Samples

*C. albicans* loads in human stools were quantified by qPCR analysis (SsoAdvanced SYBR Green Supermix, Bio-Rad) of extracted human fecal DNA using *C. albicans* specific primers: *C. albicans*-F 5'-CCTGTTTGAGCGTCGTTTCTC-3'; *C. albicans*-R 5'-TTTGGTTAGACCTAAGCCATTGTCA-3' (SEQ ID NOs. 3 and 4, respectively). *C. albicans* abundance was determined using standard curves constructed with reference genomic DNA (gDNA) of *C. albicans*.

Quantitative PCR for detection of total fungal load in human fecal DNA samples

Total fungal loads in human stools were quantified by TaqMan qPCR analysis (Premix Ex Taq™, TaKaRa) of extracted human fecal DNA using primers 36: Fungi-quant-F 5'-GGRAAACTCACCAGGTCCAG-3'; Fungi-quant-R 5'-GSWCTATCCCCAKCACGA-3', and probe: 5'-TGGTGCATGGCCGTT-3'(SEQ ID NOs. 5-7, respectively).

LEfSe Linear Discriminant Analysis

To compare differences in the configurations of fungal and bacterial microbiomes between CDI patients and healthy controls, between FMT responders and non-responders, between FMT treatment and vancomycin (STD) treatment, Lefse analyses were performed on the Huttenhower lab Galaxy server (web site: huttenhower.sph.harvard.edu/galaxy/) by importing the viral and bacterial relative abundance values and associated sample metadata, with FDR adjusted p value <0.05 considered significant and effect size calculated.

Calculation of Donor Transferred OTUs in Recipients

In samples after FMT, if a fungal or bacterial OTU was not present in the recipient baseline sample but present both in the corresponding donor baseline sample and in the recipient post-FMT sample, the OTU was defined as "donor derived"; if an OTU was not present in the corresponding donor baseline sample but detected both in the recipient baseline sample and in the recipient post-FMT sample, the OTU was defined as "recipient exclusive"; if an OTU was present across the recipient baseline sample, the recipient post-FMT sample and the corresponding donor baseline sample, the OTU was defined as "donor-recipient co-existed."

Bacterial 16S rRNA Sequencing and Data Analysis

The final fecal DNA samples were subject to bacterial 16S rRNA V4 region amplification and sequenced on the Illumina MiSeq PE250 platform (2×250 bp, BGI, China), 132,081±65,429 (number±SD) sequences obtained on average (sequence statistics in Table 5). Quality control and data analysis were implemented in mothur (v 1.38.0) as previously described 32. Any sequences with ambiguous bases and anything longer than 275 bp were removed, and aligned against the non-redundant Greengenes database (v 13.8) [33] using the NAST algorithm. Any sequences that failed to align with the V3-4 region were discarded. The remaining sequences were trimmed to the same alignment coordinates over which they fully overlapped, followed by removal of homopolymers and detection for the presence of chimeras by UChime.

The resulting sequences were classified against the Greengenes database and annotated with deepest level taxa represented by pseudo-bootstrap confidence scores of at least 80% averaged over 1,000 iterations of the naive Bayesian classifier. Any sequences that were classified as either being originated from archaea, eukarya, chloroplasts, mitochondria, or unknown kingdoms, were removed. The annotated sequences were assigned to phylotypes according to their consensus taxonomy with which at least 80% of the sequences agreed. Closed reference operational taxonomic units (OTUs) sharing 97% identity were clustered as well and assigned taxonomy according to the Greengenes database. Lefse analysis was performed to define bacterial taxa associated with CDI and healthy controls. The relative abundance of these abundance-differential taxa identified by LefSe in pre-FMT baseline samples and post-FMT last follow-up samples were plotted using pheatmap R package.

Mouse Husbandry and Model of C. difficile Infection

Studies were conducted on 4- to 6-week old demale C57BL/6 that were reared in groups of 9. Individual mice were randomized after arrival. Mice were subjected to a previously described model of CDI [34]. Briefly, mice were given an antibiotic cocktail of kanamycin (0.4 mg/mL), gentamicin (0.035 mg/mL), colistin (850 U/mL), metronidazole (0.215 mg/mL), and vancomycin (0.045 mg/mL) (all antibiotics were purchased from Sigma-Aldrich, St. Louis, MO) in their drinking water for 3 days. Mice were then given 2 days of recovery before administration of $10^7$ spores of C. difficile in PBS via oral gavage. Animal grouping and research scheme were designed as shown in FIG. 4a. On day 1 post stool infusion, diarrhea was evaluated by stool water content, calculated as stool weight loss after air drying at 70° C. for 4 hours. Colons were harvested, fixed in 4% formalin solution and embedded in paraffin. Sections were stained with hemotoxylin and eosin for histological assessment.

Figure 15A:
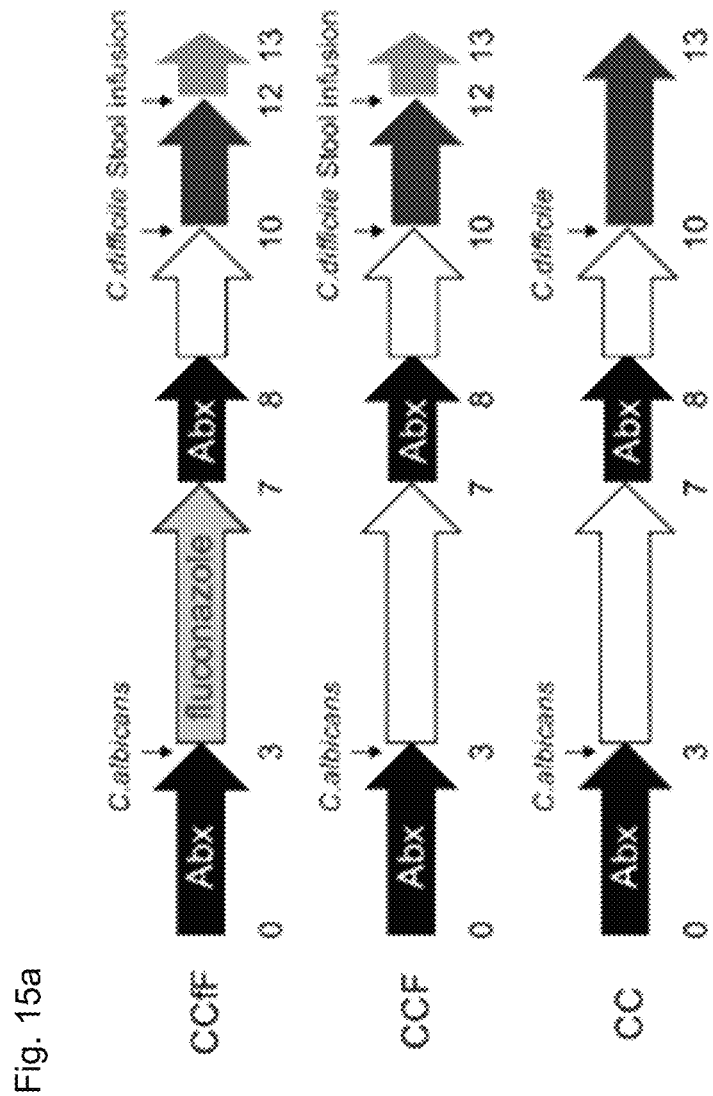
FIG. 15a-FIG. 15c Pre-FMT eradication of C. albicans in recipient mice restored FMT efficacy in clearing C. difficile infection.
Figure 15C:
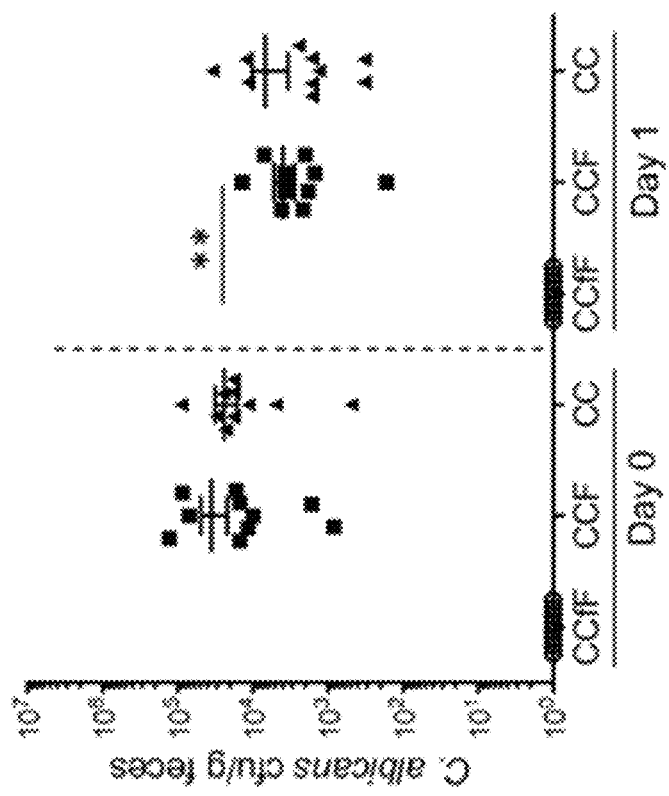
Figure 15B:
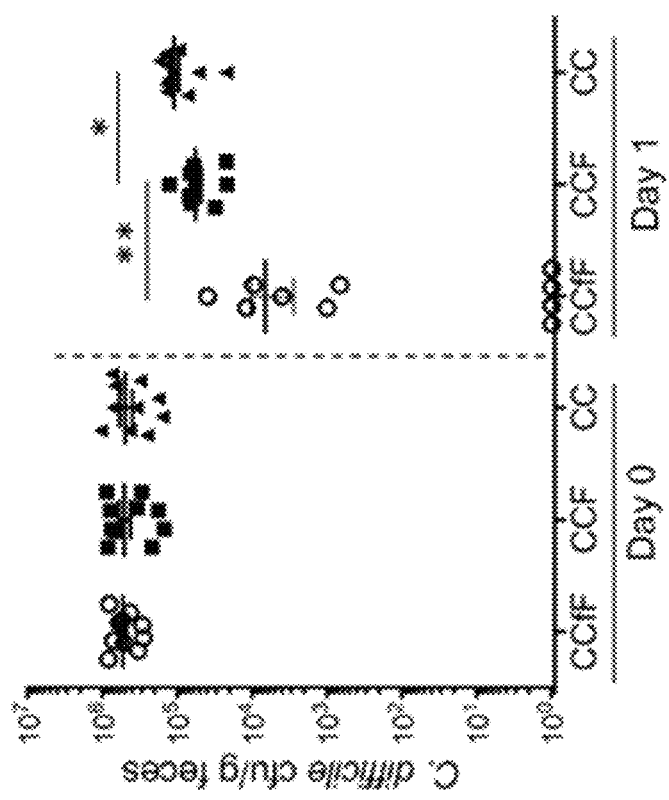

For antifungal experiment, animal grouping and research scheme were designed as shown in FIG. 15a. Mice was initially colonized with C. albicans ($2\times10^8$ cfu per mouse) after 3 days of antibiotic cocktail treatment in the drinking water, followed by 4 days of fluconazole treatment supplemented in the drinking water (0.5 mg/mL, Sigma). Then the mice were subjected to C. difficile administration ($10^7$ spores per mice) through gavage after a consecutive 1.5-day antibiotic cocktail- and 1.5-day free water-drinking. Human stool infusion was performed 2 days later after C. difficile gavage. Both C. difficile load and C. albicans load were enumerated by cultivation on Day 0 before FMT and Day 1 after FMT.

C. albicans Administration and Donor Stool Infusion in Mice

C. albicans (10231, purchased from ATCC, USA) was administered to mice ($2\times10^8$ cfu per mouse) via gavage after 3-day antibiotic treatment or supplemented in donor stool slurry at the time of donor stool infusion. Human stool from a healthy volunteer (Chinese, male, age 28 years), without presence of C. albicans as measured by qPCR, was obtained with informed consent. For stool microbiota infusions, approximately 500 mg of stool samples were cut in an anaerobic chamber and suspended in 5 ml of phosphate-buffered saline. Mice were colonized by oral gavage of 150 µl of fecal slurry with or without supplementation of C. albicans on day 2 after C. difficile challenge.

Quantification of C. difficile and C. albicans Burdens in Mouse Feces

Mouse stool were collected both before and after stool infusion. Fecal C. difficile and C. albicans burdens on day 0 before and day 1 after stool infusion were measured by cultivation. Samples were diluted in PBS and respectively plated on taurocholate cycloserine cefoxitin fructose agar (TCCFA) for quantification of C. difficile burden, on Sabouraud dextrose agar (SDA) for quantification of C. albicans load. Stool samples prior to C. albicans colonization from antibiotic-treated mice were plated on SDA to ensure that mice were C. albicans culture negative.

Data Availability

Sequence data and accompanying metadata have been deposited to the NCBI Sequence Read Archive under BioProject accession numbers PRJNA419097 and PRJNA419104.

Example 2: C. albicans Level Associated with Unfavorable FMT Outcome in IBD

Figure 21:
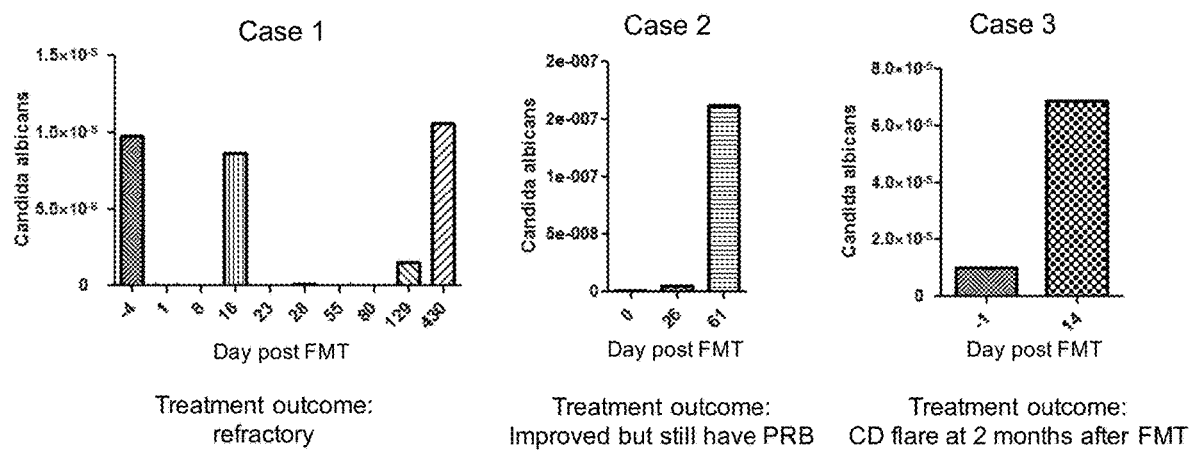
FIG. 21 Quantification of fecal C. albicans levels in IBD concurrent with CDI subjects before and after FMT. The fecal C. albicans level (gDNA content/fecal DNA) was determined by qPCR. PRB, pen rectal bleeding.

The fecal C. albicans level was investigated in three IBD patients with concurrent CDI, and subsequently followed them up after FMT (FIG. 21). Disease symptoms were ameliorated soon after FMT. However, all three patients manifested unfavorable FMT outcomes at different time-points post FMT. In accordance with the finding for CDI patients, these IBD patients all showed increased fecal *C. albicans* levels after FMT. Taken into consideration the previous observation that *C. albicans* levels were also higher in IBD than in Controls (FIG. 18), it indicates that *C. albicans* may play an unfavorable role in IBD and IBD-FMT.

All patents, patent applications, and other publications, including GenBank Accession Numbers, cited in this application are incorporated by reference in the entirety for all purposes.

TABLE 1

| Subject | Sex | Age | Smoking | Severe/ Moderate | Duration of follow up (wks) | Outcome (till last follow up) |
|---|---|---|---|---|---|---|
| FMT1 | M | 80 | Ex-smoker | Moderate | 16 | Cured |
| FMT2 | M | 52 | No | Severe | 27 | Cured |
| FMT3 | M | 38 | No | Moderate | 17 | Cured |
| FMT4 | F | 76 | No | Moderate | 18 | Cured |
| FMT5 | M | 63 | No | Severe | 18 | Cured |
| FMT6 | M | 88 | No | Severe | 23 | Cured |
| FMT7 | M | 45 | | | | Cured |
| FMT8 | M | 90 | | | | Cured |
| FMT9 | F | 52 | | | | Cured |
| FMT10 | M | 45 | Ex-smoker | Severe | 20 | Recurrence at week 19 |
| FMT11 | F | 83 | No | Moderate | 11 | Recurrence at week 5 |
| FMT12 | F | 38 | No | Severe | 28 | Recurrence at week 28 |
| FMT13 | M | 81 | | | | Recurrence at week 2 |
| FMT14 | M | 65 | | | | Recurrence at week 2 |
| FMT15 | F | 90 | | | | Recurrence at week 4 |
| FMT16 | M | 83 | | | | Recurrence at week 4 |
| STD1 | F | 78 | smoker | Severe | 14 | Cured |
| STD2 | F | 83 | No | Severe | 17 | Cured |
| STD3 | F | 99 | No | Moderate | 26 | Cured |
| STD4 | F | 85 | | | | Cured |
| STD5 | F | 92 | | | | Cured |
| STD6 | M | 88 | Ex-smoker | Severe | 20 | Recurrence at week 12 |
| STD7 | M | 93 | No | Moderate | 7 | Recurrence at week 7 |
| STD8 | M | 63 | | | | Recurrence at week 5 |

TABLE 2

Order level lefSe analysis

| order | enriched in group | LDA effect size | q value |
|---|---|---|---|
| o__Saccharomycesales | CDI | 5.26234241 | 0.00141993 |
| o__Incertae_sedis | Control | 4.22542515 | 0.01743251 |
| o__Ustilaginales | Control | 4.64245919 | 0.01113039 |
| o__Wallemiales | Control | 3.86277202 | 0.02933565 |
| o__Eurotiales | Control | 5.02946522 | 3.45E−05 |
| o__Trechisporales | Control | 4.62024264 | 0.00835961 |
| o__Agaricostilbales | Control | 4.77590173 | 0.04495598 |
| o__Mucorales | Control | 3.94917134 | 0.00275496 |
| o__Chaetothyriales | Control | 3.96218634 | 0.03957291 |
| o__unidentified | Control | 4.43843789 | 0.0011891 |

TABLE 2-continued

Family level lefSe analysis

| family | enriched in group | LDA effect size | q value |
|---|---|---|---|
| f__Incertae_sedis | CDI | 5.361603211 | 0.00032083 |
| f__Diatrypaceae | CDI | 3.647432029 | 0.02396599 |
| f__Lichtheimiaceae | Control | 3.776192836 | 0.03565053 |
| f__Marasmiaceae | Control | 4.460718116 | 0.04495598 |
| f__Cordycipitaceae | Control | 3.018060628 | 0.01080346 |
| f__Trichocomaceae | Control | 4.998286724 | 3.71E−05 |
| f__Monascaceae | Control | 4.442880786 | 0.00806352 |
| f__Ustilaginaceae | Control | 3.308596392 | 0.01113039 |
| f__Agaricostilbaceae | Control | 3.637118408 | 0.04495598 |
| f__unidentified | Control | 4.382578512 | 0.00989125 |
| f__Pichiaceae | Control | 4.234924293 | 0.00153938 |
| f__Rhizopodaceae | Control | 3.759990223 | 0.03298649 |
| f__Pleosporaceae | Control | 4.266635541 | 0.04792052 |
| f__Mucoraceae | Control | 3.546579211 | 0.00818474 |
| f__Eremotheciaceae | Control | 3.514966042 | 0.01499872 |
| f__Wallemiaceae | Control | 3.255471141 | 0.02933565 |
| f__Hydnodontaceae | Control | 3.172134768 | 0.01944714 |

Genus level lefSe analysis

| genus | enriched in group | LDA effect size | q value |
|---|---|---|---|
| g__Candida | CDI | 5.382628239 | 0.00018873 |
| g__Wallemia | Control | 3.198526789 | 0.02933565 |
| g__Trechispora | Control | 3.55075498 | 0.01944714 |
| g__Lentinula | Control | 3.687563833 | 0.04495598 |
| g__Alternaria | Control | 4.061524753 | 0.00543258 |
| g__Talaromyces | Control | 3.815612518 | 0.04495598 |
| g__Aspergillus | Control | 4.856125262 | 8.75E−05 |
| g__Pichia | Control | 3.729764446 | 0.00177011 |
| g__Thermomyces | Control | 3.268072407 | 0.0138274 |
| g__Rhizopus | Control | 3.612096939 | 0.03298649 |
| g__unidentified | Control | 4.780192159 | 0.00077864 |
| g__Simplicillium | Control | 2.905283827 | 0.01080346 |
| g__Monascus | Control | 4.416347845 | 0.00806352 |
| g__Mucor | Control | 3.444062001 | 0.00818474 |
| g__Penicillium | Control | 4.397256252 | 7.64E−05 |
| g__Sterigmatomyces | Control | 3.736578962 | 0.04495598 |
| g__Eremothecium | Control | 3.41388614 | 0.01499872 |

Species level lefSe analysis

| species | enriched in group | LDA effect size | q value |
|---|---|---|---|
| s__Candida_albicans | CDI | 4.883094137 | 0.0128582 |
| s__Hanseniaspora_sp | CDI | 2.476489287 | 0.02396599 |
| s__Penicillium_sp | CDI | 3.159815075 | 0.02226132 |
| s__Aspergillus_austroafricanus | Control | 2.820485891 | 0.02586708 |
| s__Penicillium_dierckxii | Control | 3.112142685 | 0.04495598 |
| s__Eurotiomycetes_sp | Control | 4.236581004 | 0.00632072 |
| s__Pseudozyma_churashimaensis | Control | 2.766834362 | 0.04495598 |
| s__Thermomyces_lanuginosus | Control | 3.158801272 | 0.0138274 |
| s__Ustilaginaceae_sp | Control | 2.551290082 | 0.04335394 |
| s__Monascus_purpureus | Control | 4.436483036 | 0.00806352 |
| s__Penicillium_brocae | Control | 3.202903826 | 0.00668459 |
| s__Wallemia_mellicola | Control | 3.029805635 | 0.02933565 |
| s__Sterigmatomyces_halophilus | Control | 3.158900806 | 0.04495598 |
| s__Eremothecium_sinecaudum | Control | 3.158887769 | 0.04495598 |
| s__Pseudozyma | Control | 2.865506029 | 0.04495598 |
| s__Rhodotorula_dairenensis | Control | 3.652021075 | 0.04495598 |
| s__Aspergillus_penicillioides | Control | 3.45521592 | 0.03459752 |
| s__Ophiostomataceae_sp | Control | 3.730559216 | 0.04495598 |
| s__Mucor_racemosus | Control | 2.732298798 | 0.00354366 |
| s__Lichtheimiaceae_sp | Control | 3.462009204 | 0.04495598 |
| s__Penicillium_steckii | Control | 2.538239261 | 0.03894247 |

TABLE 3

| sample_name | FMT/STD number | baseline_comparasion | Sample_collection | sample_number# | Randomization arm | Collect Date | time_point_post_treatment (FMT/STD, week) | Age | Sex | donor relationship to patient | Household ID (family ID) |
|---|---|---|---|---|---|---|---|---|---|---|---|
| F1W0 | FMT1 | CDI | longitudinal | 3 | FMT | 27 Oct. 2015 | 0 | 80 | M | | A |
| F1W2 | FMT1 | NA | longitudinal | 4 | FMT | 16 Nov. 2015 | 2 | | | | A |
| F1W6 | FMT1 | NA | longitudinal | 5 | FMT | 14 Dec. 2015 | 6 | | | | A |
| Control1 | Donor1 | Control | cross-sectional | 6 | Donor | 27 Oct. 2015 | | 35 | F | Daughter | A |
| F2W0 | FMT2 | CDI | longitudinal | 9 | FMT | 13 Feb. 2015 | 0 | 52 | M | | B |
| F2W2 | FMT2 | NA | longitudinal | 10 | FMT | 06 Mar. 2015 | 2 | | | | B |
| F2W4 | FMT2 | NA | longitudinal | 11 | FMT | 20 Mar. 2015 | 4 | | | | B |
| Control2 | Donor2 | Control | cross-sectional | 13 | Donor | 12 Feb. 2015 | | 51 | F | Wife | B |
| F3W0 | FMT3 | CDI | longitudinal | 18 | FMT | 20 Mar. 2015 | 0 | 38 | M | | C |
| F3W2 | FMT3 | NA | longitudinal | 19 | FMT | 14 Apr. 2015 | 2 | | | | C |
| F3W4 | FMT3 | NA | longitudinal | 20 | FMT | 28 Apr. 2015 | 4 | | | | C |
| F3W10 | FMT3 | NA | longitudinal | 21 | FMT | 02 Jun. 2015 | 10 | | | | C |
| F3W17 | FMT3 | NA | longitudinal | 22 | FMT | 28 Jul. 2015 | 17 | | | | C |
| Control3 | Donor3 | Control | cross-sectional | 23 | Donor | 20 Mar. 2015 | | 73 | M | Father | C |
| F4W0 | FMT4 | CDI | longitudinal | 26 | FMT | 03 Jun. 2015 | 0 | 76 | F | | D |
| F4W2 | FMT4 | NA | longitudinal | 27 | FMT | 20 Jun. 2015 | 2 | | | | D |
| F4W4 | FMT4 | NA | longitudinal | 28 | FMT | 07 Jul. 2015 | 4 | | | | D |
| F4W5 | FMT4 | NA | longitudinal | 29 | FMT | 13 Jul. 2015 | 5 | | | | D |
| F4W18 | FMT4 | NA | longitudinal | 31 | FMT | 16 Oct. 2015 | 18 | | | | D |
| Control4 | Donor4 | Control | cross-sectional | 32 | Donor | 01 Jun. 2015 | | 53 | F | Daughter | D |
| F5W0 | FMT5 | CDI | longitudinal | 38 | FMT | 30 Jul. 2015 | 0 | 63 | M | | E |
| F5W2 | FMT5 | NA | longitudinal | 39 | FMT | 18 Aug. 2015 | 2 | | | | E |
| F5W10 | FMT5 | NA | longitudinal | 40 | FMT | 19 Oct. 2015 | 10 | | | | E |
| F5W18 | FMT5 | NA | longitudinal | 41 | FMT | 14 Dec. 2015 | 18 | | | | E |
| Control5 | Donor5 | Control | cross-sectional | 42 | Donor | 31 Jul. 2015 | | 36 | F | | E |
| F6W0 | FMT6 | CDI | longitudinal | 43 | FMT | 21 Aug. 2015 | 0 | 88 | M | | F |
| F6W2 | FMT6 | NA | longitudinal | 44 | FMT | 17 Sep. 2015 | 2 | | | | F |
| F6W11 | FMT6 | NA | longitudinal | 46 | FMT | 20 Nov. 2015 | 11 | | | | F |
| Control6 | Donor6 | Control | cross-sectional | 47 | Donor | 24 Aug. 2015 | | 41 | M | Son | F |
| F7W0 | FMT7 | CDI | longitudinal | 89 | FMT | 01 Feb. 2016 | 0 | 45 | M | | G |
| F7W4 | FMT7 | NA | longitudinal | 90 | FMT | 07 Mar. 2016 | 4 | | | | G |
| F7W12 | FMT7 | NA | longitudinal | 91 | FMT | 09 May 2016 | 12 | | | | G |
| Control7 | Donor7 | Control | cross-sectional | 78 | Donor | 08 Jan. 2016 | | 35 | M | No relationship | G |
| F8W0 | FMT8 | CDI | longitudinal | 83 | FMT | 21 Jan. 2016 | 0 | 90 | M | | H |
| F8W20 | FMT8 | NA | longitudinal | 106 | FMT | 20 Jun. 2016 | 20 | | | | H |
| Control8 | Donor8 | Control | cross-sectional | 79 | Donor | 22 Jan. 2016 | | 36 | F | granddaughter | H |
| F9W0 | FMT9 | CDI | longitudinal | 127 | FMT | 15 Sep. 2016 | 0 | 52 | F | | I |
| F9W2 | FMT9 | NA | longitudinal | 128 | FMT | 30 Sep. 2016 | 2 | | | | I |
| F9W4 | FMT9 | NA | longitudinal | 129 | FMT | 14 Oct. 2016 | 4 | | | | I |
| Control9 | Donor9 | Control | cross-sectional | 130 | Donor | 09 Sep. 2016 | | 28 | F | No relationship | I |
| F10W0 | FMT10 | CDI | longitudinal | 50 | FMT | 26 Aug. 2015 | 0 | 45 | M | | J |
| F10W2 | FMT10 | NA | longitudinal | 51 | FMT | 22 Sep. 2015 | 2 | | | | J |
| F10W6 | FMT10 | NA | longitudinal | 52 | FMT | 22 Oct. 2015 | 6 | | | | J |
| F10W10 | FMT10 | NA | longitudinal | 53 | FMT | 18 Nov. 2015 | 10 | | | | J |
| Control10 | Donor10 | Control | cross-sectional | 54 | Donor | 02 Sep. 2015 | | 21 | M | Son | J |
| F11W0 | FMT11 | CDI | longitudinal | 62 | FMT | 30 Sep. 2015 | 0 | 83 | F | | K |
| F11W2 | FMT11 | NA | longitudinal | 63 | FMT | 18 Oct. 2015 | 2 | | | | K |
| F11W4 | FMT11 | NA | longitudinal | 64 | FMT | 04 Nov. 2015 | 4 | | | | K |
| Control11 | Donor11 | Control | cross-sectional | 65 | Donor | 25 Sep. 2015 | | 57 | M | Son | K |
| F12W0 | FMT12 | CDI | longitudinal | 66 | FMT | 24 Sep. 2015 | 0 | 38 | F | | L |
| F12W4 | FMT12 | NA | longitudinal | 68 | FMT | 05 Nov. 2015 | 4 | | | | L |
| F12W10 | FMT12 | NA | longitudinal | 69 | FMT | 28 Dec. 2015 | 10 | | | | L |
| F13W0 | FMT13 | CDI | longitudinal | 82 | FMT | 15 Jan. 2016 | 0 | 81 | M | | M |
| F13W2 | FMT13 | NA | longitudinal | 102 | FMT | 16 Feb. 2016 | 2 | | | | M |
| F13W13 | FMT13 | NA | longitudinal | 103 | FMT | 28 Apr. 2016 | 13 | | | | M |
| Control13 | Donor13 | NA | longitudinal | 80 | Donor | 27 Jan. 2016 | | 43 | F | Daughter | M |
| F14W0 | FMT14 | CDI | longitudinal | 113 | FMT | 21 Mar. 2016 | 0 | 65 | M | | N |
| F14W4 | FMT14 | NA | longitudinal | 115 | FMT | 29 Apr. 2016 | 4 | | | | N |
| Control14 | Donor14 | Control | cross-sectional | 119 | Donor | 22 Mar. 2016 | | 33 | M | Son | N |
| F15W0 | FMT15 | CDI | longitudinal | 131 | FMT | 14 Sep. 2016 | 0 | 90 | F | | O |
| F15W2 | FMT15 | NA | longitudinal | 132 | FMT | 05 Oct. 2016 | 2 | | | | O |
| F15W4 | FMT15 | NA | longitudinal | 133 | FMT | 18 Oct. 2016 | 4 | | | | O |
| Control15 | Donor15 | Control | cross-sectional | 134 | Donor | 13 Sep. 2016 | | 52 | M | Son | O |
| F16W0 | FMT16 | CDI | longitudinal | 7 | FMT | 26 Nov. 2015 | 0 | 83 | M | | P |
| F16W4 | FMT16 | NA | longitudinal | 86 | FMT | 08 Jan. 2016 | 4 | | | | P |
| Control16 | Donor16 | Control | cross-sectional | 8 | Donor | 11 Dec. 2015 | | 27 | F | Maid | P |

TABLE 3-continued

| sample_name | FMT/STD number | baseline_comparasion | Sample_collection | sample_number# | Randomization arm | Collect Date | time_point_post_treatment (FMT/STD, week) | Age | Sex | donor relationship to patient | Household ID (family ID) |
|---|---|---|---|---|---|---|---|---|---|---|---|
| S1W0 | STD1 | CDI | longitudinal | 33 | Std therapy | 14 Jul. 2015 | 0 | 78 | F | | |
| S1W2 | STD1 | NA | longitudinal | 34 | Std therapy | 24 Jul. 2015 | 2 | | | | |
| S1W4 | STD1 | NA | longitudinal | 35 | Std therapy | 10 Aug. 2015 | 4 | | | | |
| S2W0 | STD2 | CDI | longitudinal | 58 | Std therapy | 24 Sep. 2015 | 0 | 83 | F | | |
| S2W2 | STD2 | NA | longitudinal | 59 | Std therapy | 05 Oct. 2015 | 2 | | | | |
| S2W4 | STD2 | NA | longitudinal | 60 | Std therapy | 19 Oct. 2015 | 4 | | | | |
| S2W10 | STD2 | NA | longitudinal | 61 | Std therapy | 30 Nov. 2015 | 10 | | | | |
| S3W0 | STD3 | CDI | longitudinal | 71 | Std therapy | 20 Oct. 2015 | 0 | 99 | F | | |
| S3W2 | STD3 | NA | longitudinal | 72 | Std therapy | 02 Nov. 2015 | 2 | | | | |
| S3W4 | STD3 | NA | longitudinal | 73 | Std therapy | 16 Nov. 2015 | 4 | | | | |
| S4W0 | STD4 | CDI | longitudinal | 81 | Std therapy | 07 Jan. 2016 | 0 | 85 | F | | |
| S4W2 | STD4 | NA | longitudinal | 98 | Std therapy | 25 Jan. 2016 | 2 | | | | |
| S4W10 | STD4 | NA | longitudinal | 100 | Std therapy | 21 Mar. 2016 | 10 | | | | |
| S5W0 | STD5 | CDI | longitudinal | 107 | Std therapy | 16 Mar. 2016 | 0 | 92 | F | | |
| S5W2 | STD5 | NA | longitudinal | 108 | Std therapy | 31 Mar. 2016 | 2 | | | | |
| S5W4 | STD5 | NA | longitudinal | 109 | Std therapy | 19 Apr. 2016 | 4 | | | | |
| S5W10 | STD5 | NA | longitudinal | 110 | Std therapy | 03 Jun. 2016 | 10 | | | | |
| S5W13 | STD5 | NA | longitudinal | 111 | Std therapy | 17 Jun. 2016 | 13 | | | | |
| S5W23 | STD5 | NA | longitudinal | 112 | Std therapy | 26 Aug. 2016 | 23 | | | | |
| S6W0 | STD6 | CDI | longitudinal | 14 | Std therapy | 06 Mar. 2015 | 0 | 88 | M | | |
| S6W2 | STD6 | NA | longitudinal | 15 | Std therapy | 18 Mar. 2015 | 2 | | | | |
| S6W10 | STD6 | NA | longitudinal | 17 | Std therapy | 05 May 2015 | 10 | | | | |
| S7W0 | STD7 | CDI | longitudinal | 24 | Std therapy | 07 May 2015 | 0 | 93 | M | | |
| S7W2 | STD7 | NA | longitudinal | 25 | Std therapy | 22 May 2015 | 2 | | | | |
| S8W0 | STD8 | CDI | longitudinal | 120 | Std therapy | 19 Jul. 2016 | 0 | 63 | M | | |
| S8W4 | STD8 | NA | longitudinal | 121 | Std therapy | 19 Aug. 2016 | 4 | | | | |
| CDI25 | NA | CDI | cross-sectional | 1 | NA | | 0 | 86 | F | | Q |
| Control12 | NA | NA | cross-sectional | 2 | NA | 04 Mar. 2015 | | | | | Q |
| CDI26 | NA | CDI | cross-sectional | 88 | NA | 30 Dec. 2015 | 0 | 88 | M | | |
| Control17 | NA | Control | cross-sectional | 37 | NA | 21 Jul. 2015 | | 55 | F | | |
| CDI27 | NA | CDI | cross-sectional | 48 | NA | 31 Aug. 2015 | 0 | 66 | F | | R |
| Control18 | NA | Control | cross-sectional | 49 | NA | 26 Aug. 2015 | | 41 | M | | R |
| CDI28 | NA | CDI | cross-sectional | 5 | NA | 07 Sep. 2015 | 0 | 84 | M | | S |
| Control19 | NA | Control | cross-sectional | 57 | NA | 08 Sep. 2015 | | 42 | M | Son | S |
| CDI29 | NA | CDI | cross-sectional | 70 | NA | 08 Oct. 2015 | 0 | 76 | M | | |
| CDI30 | NA | CDI | cross-sectional | 74 | NA | 11 Dec. 2015 | 0 | 25 | F | | T |
| Control20 | NA | Control | cross-sectional | 75 | NA | 24 Dec. 2015 | | 33 | M | Brother | T |
| DI31 | NA | CDI | cross-sectional | 122 | NA | 28 Jul. 2016 | | 80 | F | | |
| CDI32 | NA | CDI | cross-sectional | 124 | NA | 29 Aug. 2016 | 0 | 52 | M | | |
| Control21 | NA | Control | cross-sectional | ANS2357 | NA | | | | | | |
| Control22 | NA | Control | cross-sectional | ANS2331 | NA | | | | | | |
| Control23 | NA | Control | cross-sectional | ANS2237 | NA | | | | | | |
| Control24 | NA | Control | cross-sectional | ANS2467 | NA | | | | | | |

TABLE 4

| sample_name | sample_num-Aer | Sequencing_platform | strategy | length | Nreads | raw_reads | clean_reads | clean_data.raw_data | Duplication | Clean data Mbp. |
|---|---|---|---|---|---|---|---|---|---|---|
| F1W0 | A3 | Illumina_Miseq | PE300 | 294 | 0.16 | 179802 | 81730 | 45.46 | 0 | 24.27 |
| F1W2 | A4 | Illumina_Miseq | PE300 | 300 | 0 | 616376 | 139656 | 22.66 | 0 | 41.9 |
| F1W6 | A5 | Illumina_Miseq | PE300 | 300 | 0.228 | 1031864 | 316410 | 30.66 | 0 | 94.92 |
| Control1 | A6 | Illumina_Miseq | PE300 | 300 | 0.139 | 433810 | 181802 | 41.91 | 0 | 54.54 |
| F2W0 | A9 | Illumina_Miseq | PE300 | 299 | 0.14 | 202246 | 158372 | 78.31 | 0 | 47.43 |
| F2W2 | A10 | Illumina_Miseq | PE300 | 300 | 0.13 | 238288 | 185840 | 77.99 | 0 | 55.75 |
| F2W4 | A11 | Illumina_Miseq | PE300 | 298 | 0.14 | 274630 | 230666 | 83.99 | 0 | 68.97 |
| Control2 | A13 | Illumina_Miseq | PE300 | 300 | 0.165 | 339154 | 46712 | 13.77 | 0 | 14.01 |
| F3W0 | A18 | Illumina_Miseq | PE300 | 300 | 0 | 231822 | 93316 | 40.25 | 0 | 27.99 |
| F3W2 | A19 | Illumina_Miseq | PE300 | 300 | 0.105 | 618984 | 262320 | 42.38 | 0 | 78.7 |
| F3W4 | A20 | Illumina_Miseq | PE300 | 300 | 0.13 | 801066 | 294282 | 36.74 | 0 | 88.28 |
| F3W10 | A21 | Illumina_Miseq | PE300 | 300 | 0.131 | 762700 | 277712 | 36.41 | 0 | 83.31 |
| F3W17 | A22 | Illumina_Miseq | PE300 | 300 | 0.139 | 696480 | 71662 | 10.29 | 0 | 21.5 |
| Control3 | A23 | Illumina_Miseq | PE300 | 300 | 0 | 207068 | 84600 | 40.86 | 0 | 25.38 |
| F4W0 | A26 | Illumina_Miseq | PE300 | 300 | 0 | 209102 | 67856 | 32.45 | 0 | 20.36 |
| F4W2 | A27 | Illumina_Miseq | PE300 | 300 | 0 | 216998 | 88906 | 40.97 | 0 | 26.67 |
| F4W4 | A28 | Illumina_Miseq | PE300 | 300 | 0.112 | 240322 | 93194 | 38.78 | 0 | 27.96 |
| F4W5 | A29 | Illumina_Miseq | PE300 | 300 | 0.001 | 132580 | 50098 | 37.79 | 0 | 15.03 |
| F4W18 | A31 | Illumina_Miseq | PE300 | 300 | 0 | 173430 | 49710 | 28.66 | 0 | 14.91 |
| Control4 | A32 | Illumina_Miseq | PE300 | 300 | 0.001 | 1708684 | 752020 | 44.01 | 0 | 225.61 |
| F5W0 | A38 | Illumina_Miseq | PE300 | 293 | 0.14 | 248084 | 109264 | 44.04 | 0 | 32.34 |
| F5W2 | A39 | Illumina_Miseq | PE300 | 297 | 0.14 | 181924 | 81388 | 44.74 | 0 | 24.25 |
| F5W10 | A40 | Illumina_Miseq | PE300 | 300 | 0.075 | 140624 | 54390 | 38.68 | 0 | 16.32 |
| F5W18 | A41 | Illumina_Miseq | PE300 | 296 | 0.13 | 192510 | 94050 | 48.85 | 0 | 27.89 |
| Control5 | A42 | Illumina_Miseq | PE300 | 300 | 0.208 | 215010 | 91448 | 42.53 | 0 | 27.43 |
| F6W0 | A43 | Illumina_Miseq | PE300 | 298 | 0.15 | 282544 | 219516 | 77.69 | 0 | 65.64 |
| F6W2 | A44 | Illumina_Miseq | PE300 | 300 | 0.035 | 298672 | 118338 | 39.62 | 0 | 35.5 |
| F6W11 | A46 | Illumina_Miseq | PE300 | 300 | 0.045 | 275570 | 122034 | 44.28 | 0 | 36.61 |
| Control6 | A47 | Illumina_Miseq | PE300 | 297 | 0.12 | 344408 | 244256 | 70.92 | 0 | 72.54 |
| F7W0 | A89 | Illumina_Miseq | PE300 | 300 | 0.083 | 257738 | 78176 | 30.33 | 0 | 23.45 |
| F7W4 | A90 | Illumina_Miseq | PE300 | 293 | 0.18 | 202056 | 105384 | 52.16 | 0 | 31.25 |
| F7W12 | A91 | Illumina_Miseq | PE300 | 300 | 0.068 | 211482 | 17624 | 8.33 | 0 | 5.29 |
| Control7 | A78 | Illumina_Miseq | PE300 | 300 | 0.074 | 321992 | 36754 | 11.41 | 0 | 11.03 |
| F8W0 | A83 | Illumina_Miseq | PE300 | 300 | 0 | 400454 | 105068 | 26.24 | 0 | 31.52 |
| F8W20 | A106 | Illumina_Miseq | PE300 | 300 | 0.018 | 329840 | 55682 | 16.88 | 0 | 16.7 |
| Control8 | A79 | Illumina_Miseq | PE300 | 300 | 0.037 | 271614 | 136442 | 50.23 | 0 | 40.93 |
| F9W0 | A127 | Illumina_Miseq | PE300 | 297 | 0.15 | 222020 | 181952 | 81.95 | 0 | 54.22 |
| F9W2 | A128 | Illumina_Miseq | PE300 | 296 | 0.15 | 303888 | 236462 | 77.81 | 0 | 69.64 |
| F9W4 | A129 | Illumina_Miseq | PE300 | 294 | 0.14 | 378688 | 327536 | 86.49 | 0 | 96.13 |
| Control9 | A130 | Illumina_Miseq | PE300 | 300 | 0.055 | 308178 | 107542 | 34.9 | 0 | 32.26 |
| F10W0 | A50 | Illumina_Miseq | PE300 | 299 | 0.15 | 365022 | 166948 | 45.74 | 0 | 49.5 |
| F10W2 | A51 | Illumina_Miseq | PE300 | 298 | 0.13 | 342394 | 166724 | 48.69 | 0 | 49.6 |
| F10W6 | A52 | Illumina_Miseq | PE300 | 294 | 0.14 | 444320 | 194454 | 43.76 | 0 | 57.07 |
| F10W10 | A53 | Illumina_Miseq | PE300 | 300 | 0.019 | 652970 | 251992 | 38.59 | 0 | 75.6 |
| Control10 | A54 | Illumina_Miseq | PE300 | 300 | 0.017 | 888528 | 237676 | 26.75 | 0 | 71.3 |
| F11W0 | A62 | Illumina_Miseq | PE300 | 293 | 0.15 | 220522 | 108276 | 49.1 | 0 | 31.89 |
| F11W2 | A63 | Illumina_Miseq | PE300 | 300 | 0.117 | 347680 | 112438 | 32.34 | 0 | 33.73 |
| F11W4 | A64 | Illumina_Miseq | PE300 | 300 | 0.14 | 265458 | 123800 | 46.64 | 0 | 36.89 |
| Control11 | A65 | Illumina_Miseq | PE300 | 300 | 0.076 | 364878 | 147312 | 40.37 | 0 | 44.19 |
| F12W0 | A66 | Illumina_Miseq | PE300 | 299 | 0.13 | 385064 | 168008 | 43.63 | 0 | 49.98 |
| F12W4 | A68 | Illumina_Miseq | PE300 | 293 | 0.13 | 239996 | 94998 | 39.58 | 0 | 28.12 |
| F12W10 | A69 | Illumina_Miseq | PE300 | 294 | 0.13 | 367404 | 180104 | 49.02 | 0 | 52.86 |
| F13W0 | A82 | Illumina_Miseq | PE300 | 300 | 0.015 | 505218 | 166652 | 32.99 | 0 | 50 |
| F13W2 | A102 | Illumina_Miseq | PE300 | 300 | 0.073 | 233864 | 84538 | 36.15 | 0 | 25.36 |
| F13W13 | A103 | Illumina_Miseq | PE300 | 297 | 0.14 | 196280 | 83390 | 42.49 | 0 | 24.64 |
| Control13 | A80 | Illumina_Miseq | PE300 | 300 | 0.058 | 306382 | 124604 | 40.67 | 0 | 37.38 |
| F14W0 | A113 | Illumina_Miseq | PE300 | 298 | 0.15 | 183402 | 137498 | 74.97 | 0 | 40.84 |
| F14W4 | A115 | Illumina_Miseq | PE300 | 297 | 0.12 | 298982 | 138884 | 46.45 | 0 | 41.11 |
| Control14 | A119 | Illumina_Miseq | PE300 | 300 | 0.13 | 205292 | 159234 | 77.56 | 0 | 47.37 |
| F15W0 | A131 | Illumina_Miseq | PE300 | 300 | 0.14 | 629728 | 298766 | 47.44 | 0 | 88.58 |
| F15W2 | A132 | Illumina_Miseq | PE300 | 299 | 0.15 | 357030 | 171648 | 48.08 | 0 | 50.81 |
| F15W4 | A133 | Illumina_Miseq | PE300 | 300 | 0.15 | 309054 | 151058 | 48.88 | 0 | 45.09 |
| Control15 | A134 | Illumina_Miseq | PE300 | 300 | 0 | 471798 | 185850 | 39.39 | 0 | 55.76 |
| F16W0 | A7 | Illumina_Miseq | PE300 | 300 | 0.185 | 346110 | 73132 | 21.13 | 0 | 21.94 |
| F16W4 | A86 | Illumina_Miseq | PE300 | 299 | 0.12 | 327154 | 132150 | 40.39 | 0 | 39.58 |
| Control16 | A8 | Illumina_Miseq | PE300 | 300 | 0.147 | 292252 | 39628 | 13.56 | 0 | 11.89 |
| S1W0 | A33 | Illumina_Miseq | PE300 | 300 | 0.001 | 770414 | 328156 | 42.59 | 0 | 98.45 |
| S1W2 | A34 | Illumina_Miseq | PE300 | 299 | 0.14 | 175118 | 75890 | 43.34 | 0 | 22.65 |
| S1W4 | A35 | Illumina_Miseq | PE300 | 298 | 0.15 | 234894 | 110164 | 46.9 | 0 | 32.83 |
| S2W0 | A58 | Illumina_Miseq | PE300 | 297 | 0.14 | 335058 | 249376 | 74.43 | 0 | 73.94 |
| S2W2 | A59 | Illumina_Miseq | PE300 | 294 | 0.14 | 405606 | 276022 | 68.05 | 0 | 81.98 |
| S2W4 | A60 | Illumina_Miseq | PE300 | 296 | 0.12 | 176070 | 132478 | 75.24 | 0 | 39.21 |
| S2W10 | A61 | Illumina_Miseq | PE300 | 300 | 0.068 | 346262 | 38884 | 11.23 | 0 | 11.67 |
| S3W0 | A71 | Illumina_Miseq | PE300 | 300 | 0.108 | 199368 | 44866 | 22.5 | 0 | 13.46 |
| S3W2 | A72 | Illumina_Miseq | PE300 | 296 | 0.15 | 269004 | 119998 | 44.61 | 0 | 35.52 |
| S3W4 | A73 | Illumina_Miseq | PE300 | 293 | 0.07 | 291644 | 58196 | 19.95 | 0 | 17.05 |

TABLE 4-continued

| sample_name | sample_number | Sequencing_platform | strategy | length | Nreads | raw_reads | clean_reads | clean_data.raw_data | Duplication | Clean data Mbp. |
|---|---|---|---|---|---|---|---|---|---|---|
| S4W0 | A81 | Illumina_Miseq | PE300 | 300 | 0.015 | 712372 | 170362 | 23.91 | 0 | 51.11 |
| S4W2 | A98 | Illumina_Miseq | PE300 | 299 | 0.15 | 410054 | 186270 | 45.43 | 0 | 55.32 |
| S4W10 | A100 | Illumina_Miseq | PE300 | 300 | 0.066 | 223792 | 94782 | 42.35 | 0 | 28.43 |
| S5W0 | A107 | Illumina_Miseq | PE300 | 300 | 0 | 431392 | 221564 | 51.36 | 0 | 66.47 |
| S5W2 | A108 | Illumina_Miseq | PE300 | 296 | 0.13 | 209076 | 72748 | 34.8 | 0 | 21.53 |
| S5W4 | A109 | Illumina_Miseq | PE300 | 294 | 0.14 | 245218 | 101786 | 41.51 | 0 | 30.03 |
| S5W10 | A110 | Illumina_Miseq | PE300 | 293 | 0.14 | 267352 | 112302 | 42.01 | 0 | 33.07 |
| S5W13 | A111 | Illumina_Miseq | PE300 | 293 | 0.14 | 309046 | 123178 | 39.86 | 0 | 36.21 |
| S5W23 | A112 | Illumina_Miseq | PE300 | 300 | 0.086 | 407234 | 89072 | 21.87 | 0 | 26.72 |
| S6W0 | A14 | Illumina_Miseq | PE300 | 296 | 0.13 | 300734 | 121426 | 40.38 | 0 | 36.12 |
| S6W2 | A15 | Illumina_Miseq | PE300 | 294 | 0.14 | 381812 | 175862 | 46.06 | 0 | 52.14 |
| S6W10 | A17 | Illumina_Miseq | PE300 | 293 | 0.09 | 373944 | 109182 | 29.2 | 0 | 32.26 |
| S7W0 | A24 | Illumina_Miseq | PE300 | 300 | 0 | 385622 | 128024 | 33.2 | 0 | 38.41 |
| S7W2 | A25 | Illumina_Miseq | PE300 | 297 | 0.12 | 280482 | 115920 | 41.33 | 0 | 34.54 |
| S8W0 | A120 | Illumina_Miseq | PE300 | 298 | 0.13 | 211678 | 100168 | 47.32 | 0 | 29.95 |
| S8W4 | A121 | Illumina_Miseq | PE300 | 299 | 0.14 | 219782 | 94604 | 43.04 | 0 | 28.33 |
| CDI25 | A1 | Illumina_Miseq | PE300 | 297 | 0.13 | 266926 | 117804 | 44.13 | 0 | 35.16 |
| Control12 | A2 | Illumina_Miseq | PE300 | 296 | 0.13 | 380378 | 163882 | 43.08 | 0 | 48.84 |
| CDI26 | A88 | Illumina_Miseq | PE300 | 300 | 0.029 | 539830 | 199604 | 36.98 | 0 | 59.88 |
| Control17 | A37 | Illumina_Miseq | PE300 | 300 | 0.256 | 343310 | 112180 | 32.68 | 0 | 33.65 |
| CDI27 | A48 | Illumina_Miseq | PE300 | 300 | 0.12 | 386578 | 128450 | 33.23 | 0 | 38.53 |
| Control18 | A49 | Illumina_Miseq | PE300 | 297 | 0.13 | 353998 | 247752 | 69.99 | 0 | 73.09 |
| CDI28 | A55 | Illumina_Miseq | PE300 | 296 | 0.14 | 288796 | 124028 | 42.95 | 0 | 36.96 |
| Control19 | A57 | Illumina_Miseq | PE300 | 300 | 0.071 | 866640 | 91022 | 10.5 | 0 | 27.31 |
| CDI29 | A70 | Illumina_Miseq | PE300 | 298 | 0.12 | 331604 | 159998 | 48.25 | 0 | 47.52 |
| CDI30 | A74 | Illumina_Miseq | PE300 | 294 | 0.15 | 222838 | 163664 | 73.45 | 0 | 48.2 |
| CDI31 | A122 | Illumina_Miseq | PE300 | 300 | 0.071 | 218720 | 46710 | 21.36 | 0 | 14.01 |
| CDI32 | A124 | Illumina_Miseq | PE300 | 298 | 0.15 | 541002 | 285192 | 52.72 | 0 | 84.42 |
| Control20 | A136 | Illumina_Miseq | PE300 | 300 | 0.056 | 425346 | 154348 | 36.29 | 0 | 46.3 |
| Control21 | A137 | Illumina_Miseq | PE300 | 300 | 0.125 | 817664 | 347726 | 42.53 | 0 | 104.32 |
| Control22 | A138 | Illumina_Miseq | PE300 | 300 | 0.147 | 1584946 | 635954 | 40.12 | 0 | 190.79 |
| Control23 | A139 | Illumina_Miseq | PE300 | 300 | 0.155 | 540728 | 250244 | 46.28 | 0 | 75.07 |

TABLE 5

| sample_name | sample_NUMBER | Sequencing platform | Sequencing_Strategy. PE. SE. | Raw-Reads | Read_length. bp. | Clean_Data. Raw_Data . . . | Clean_Reads | Read_GC . . . | Adapter_Rate . . . | Duplication Rate . . . | N rate . . . |
|---|---|---|---|---|---|---|---|---|---|---|---|
| F1W0 | B3 | Illumina_Miseq | PE250 | 139020 | 250 | 36.41 | 50614 | 54.77 | 0 | — | 0 |
| F1W2 | B4 | Illumina_Miseq | PE250 | 453216 | 250 | 49.63 | 224930 | 55.19 | 0 | — | 0 |
| F1W6 | B5 | Illumina_Miseq | PE250 | 210766 | 250 | 54.7 | 115298 | 54.43 | 0 | — | 0 |
| Control1 | B6 | Illumina_Miseq | PE250 | 197162 | 250 | 56.09 | 110582 | 53.81 | 0 | — | 0 |
| F2W0 | B9 | Illumina_Miseq | PE250 | 145174 | 250 | 36.12 | 52432 | 56.19 | 0 | — | 0 |
| F2W2 | B10 | Illumina_Miseq | PE250 | 165058 | 250 | 39.87 | 65806 | 53.31 | 0 | — | 0 |
| F2W4 | B11 | Illumina_Miseq | PE250 | 157286 | 250 | 51.06 | 80306 | 55.57 | 0 | — | 0 |
| Control2 | B13 | Illumina_Miseq | PE250 | 178348 | 250 | 53.95 | 96226 | 53.59 | 0 | — | 0 |
| F3W0 | B18 | Illumina_Miseq | PE250 | 392454 | 250 | 37.82 | 148440 | 51.66 | 0 | — | 0 |
| F3W2 | B19 | Illumina_Miseq | PE250 | 230982 | 250 | 44.39 | 102532 | 54.01 | 0 | — | 0 |
| F3W4 | B20 | Illumina_Miseq | PE250 | 112378 | 250 | 47.17 | 53006 | 53.36 | 0 | — | 0 |
| F3W10 | B21 | Illumina_Miseq | PE250 | 230772 | 250 | 44.67 | 103090 | 52.81 | 0 | — | 0 |
| F3W17 | B22 | Illumina_Miseq | PE250 | 311224 | 250 | 44.88 | 139674 | 54.17 | 0 | — | 0 |
| Control3 | B23 | Illumina_Miseq | PE250 | 523854 | 250 | 48.24 | 252724 | 53.82 | 0 | — | 0 |
| F4W0 | B26 | Illumina_Miseq | PE250 | 174036 | 250 | 41.06 | 71452 | 54.33 | 0 | — | 0 |
| F4W2 | B27 | Illumina_Miseq | PE250 | 220990 | 250 | 43.23 | 95524 | 55.18 | 0 | — | 0 |

TABLE 5-continued

| sample_name | sample_NUMBER | Sequencing_platform | Sequencing_Strategy. PE. SE. | Raw-Reads | Read_length. bp. | Clean_Data. Raw_Data | Clean_Reads | Read_GC | Adapter_Rate | Duplication Rate | N rate |
|---|---|---|---|---|---|---|---|---|---|---|---|
| F4W4 | B28 | Illumina_Miseq | PE250 | 241624 | 250 | 36.16 | 87376 | 55.01 | 0 | — | 0 |
| F4W5 | B29 | Illumina_Miseq | PE250 | 180292 | 250 | 47.99 | 86526 | 58.15 | 0 | — | 0 |
| F4W18 | B31 | Illumina_Miseq | PE250 | 201408 | 250 | 43.77 | 88154 | 54.42 | 0 | — | 0 |
| Control4 | B32 | Illumina_Miseq | PE250 | 421468 | 250 | 49.82 | 209980 | 53.83 | 0 | — | 0 |
| F5W0 | B38 | Illumina_Miseq | PE250 | 141266 | 250 | 37.14 | 52462 | 53.82 | 0 | — | 0 |
| F5W2 | B39 | Illumina_Miseq | PE250 | 144132 | 250 | 32.13 | 46310 | 53.24 | 0 | — | 0 |
| F5W10 | B40 | Illumina_Miseq | PE250 | 218376 | 250 | 38.59 | 84272 | 54.1 | 0 | — | 0 |
| F5W18 | B41 | Illumina_Miseq | PE250 | 238492 | 250 | 36.26 | 86488 | 53.76 | 0 | — | 0 |
| Control5 | B42 | Illumina_Miseq | PE250 | 350844 | 250 | 46.31 | 162472 | 54.36 | 0 | — | 0 |
| F6W0 | B43 | Illumina_Miseq | PE250 | 266526 | 250 | 37.13 | 98972 | 54.74 | 0 | — | 0 |
| F6W2 | B44 | Illumina_Miseq | PE250 | 236454 | 250 | 44.09 | 104262 | 53.8 | 0 | — | 0 |
| F6W11 | B46 | Illumina_Miseq | PE250 | 233562 | 250 | 45.15 | 105462 | 54.06 | 0 | — | 0 |
| Control6 | B47 | Illumina_Miseq | PE250 | 305446 | 250 | 55.31 | 168944 | 54.78 | 0 | — | 0 |
| F7W0 | B89 | Illumina_Miseq | PE250 | 237086 | 250 | 79.42 | 188300 | 54.91 | 0 | — | 0 |
| F7W4 | B90 | Illumina_Miseq | PE250 | 235976 | 250 | 83.49 | 197021 | 53.01 | 0 | — | 0 |
| F7W12 | B91 | Illumina_Miseq | PE250 | 250973 | 250 | 79.33 | 199092 | 53.2 | 0 | — | 0 |
| Control7 | B78 | Illumina_Miseq | PE250 | 203468 | 250 | 50.32 | 102382 | 54.61 | 0 | — | 0 |
| F8W0 | B83 | Illumina_Miseq | PE250 | 131878 | 250 | 26.67 | 35168 | 54.94 | 0 | — | 0 |
| F8W20 | B106 | Illumina_Miseq | PE250 | 167805 | 250 | 83.11 | 139457 | 53.09 | 0 | — | 0 |
| Control8 | B79 | Illumina_Miseq | PE250 | 242486 | 250 | 58.72 | 142396 | 55.31 | 0 | — | 0 |
| F9W0 | B127 | Illumina_Miseq | PE250 | 196849 | 250 | 80.26 | 157992 | 52.39 | 0 | — | 0 |
| F9W2 | B128 | Illumina_Miseq | PE250 | 204701 | 250 | 77.69 | 159032 | 51.85 | 0 | — | 0 |
| F9W4 | B129 | Illumina_Miseq | PE250 | 174369 | 250 | 79.82 | 139188 | 53.08 | 0 | — | 0 |
| Control9 | B130 | Illumina_Miseq | PE250 | 158498 | 250 | 81.99 | 129950 | 52.62 | 0 | — | 0 |
| F10W0 | B50 | Illumina_Miseq | PE250 | 283910 | 250 | 33.77 | 95884 | 55.08 | 0 | — | 0 |
| F10W2 | B51 | Illumina_Miseq | PE250 | 200238 | 250 | 30.26 | 60588 | 55.17 | 0 | — | 0 |
| F10W6 | B52 | Illumina_Miseq | PE250 | 170482 | 250 | 38.49 | 65614 | 54.36 | 0 | — | 0 |
| F10W10 | B53 | Illumina_Miseq | PE250 | 178994 | 250 | 36.65 | 65606 | 54.59 | 0 | — | 0 |
| Control10 | B54 | Illumina_Miseq | PE250 | 824186 | 250 | 40.69 | 335336 | 53.36 | 0 | — | 0 |
| F11W0 | B62 | Illumina_Miseq | PE250 | 215272 | 250 | 42.74 | 92012 | 53.28 | 0 | — | 0 |
| F11W2 | B63 | Illumina_Misec | PE250 | 195352 | 250 | 44.86 | 87634 | 53.31 | 0 | — | 0 |
| F11W4 | B64 | Illumina_Miseq | PE250 | 193674 | 250 | 29.48 | 57096 | 55.18 | 0 | — | 0 |
| Control11 | B65 | Illumina_Miseq | PE250 | 183434 | 250 | 47.41 | 86968 | 55.82 | 0 | — | 0 |
| F12W0 | B66 | Illumina_Miseq | PE250 | 130132 | 250 | 28.16 | 36646 | 51.56 | 0 | — | 0 |
| F12W4 | B68 | Illumina_Miseq | PE250 | 442748 | 250 | 38.11 | 168732 | 52.41 | 0 | — | 0 |
| F12W10 | B69 | Illumina_Miseq | PE250 | 376794 | 250 | 44.61 | 168084 | 54.27 | 0 | — | 0 |
| F13W0 | B82 | Illumina_Miseq | PE250 | 295522 | 250 | 35.97 | 106314 | 54.32 | 0 | — | 0 |

TABLE 5-continued

| sample_name | sample_NUMBER | Sequencing_platform | Sequencing_Strategy. PE. SE. | Raw-Reads | Read_length. bp. | Clean_Data. Raw_Data... | Clean_Reads | Read_GC... | Adapter_Rate... | Duplication Rate... | N rate... |
|---|---|---|---|---|---|---|---|---|---|---|---|
| F13W2 | B102 | Illumina_Miseq | PE250 | 163065 | 250 | 82.16 | 133971 | 54.28 | 0 | — | 0 |
| F13W13 | B103 | Illumina_Misec | PE250 | 207191 | 250 | 80.73 | 167256 | 53.56 | 0 | — | 0 |
| Control13 | B80 | Illumina_Miseq | PE250 | 462154 | 250 | 48.56 | 224408 | 53.21 | 0 | — | 0 |
| F14W0 | B113 | Illumina_Miseq | PE250 | 223935 | 250 | 81.37 | 182212 | 52.37 | 0 | — | 0 |
| F14W4 | B115 | Illumina_Miseq | PE250 | 259086 | 250 | 76.58 | 198409 | 53.36 | 0 | — | 0 |
| Control14 | B119 | Illumina_Miseq | PE250 | 247736 | 250 | 78.41 | 194254 | 51.97 | 0 | — | 0 |
| F15W0 | B131 | Illumina_Miseo | PE250 | 154491 | 250 | 79.7 | 123134 | 56.75 | 0 | — | 0 |
| F15W2 | B132 | Illumina_Miseq | PE250 | 148992 | 250 | 77.43 | 115366 | 51.66 | 0 | — | 0 |
| F15W4 | B133 | Illumina_Misec | PE250 | 112623 | 250 | 81.68 | 91988 | 55.07 | 0 | — | 0 |
| Control15 | B134 | Illumina_Miseq | PE250 | 253469 | 250 | 74.17 | 187995 | 52.93 | 0 | — | 0 |
| F16W0 | B7 | Illumina_Miseq | PE250 | 115544 | 250 | 47.42 | 54786 | 55.67 | 0 | — | 0 |
| F16W4 | B86 | Illumina_Miseq | PE250 | 281377 | 250 | 73.93 | 208021 | 51.76 | 0 | — | 0 |
| Control16 | B8 | Illumina_Miseq | PE250 | 192726 | 250 | 49.58 | 95562 | 55.47 | 0 | — | 0 |
| SIWo | B33 | Illumina_Miseq | PE250 | 127724 | 250 | 48.49 | 61934 | 53.3 | 0 | — | 0 |
| S1W2 | B34 | Illumina_Miseq | PE250 | 156738 | 250 | 40.52 | 63506 | 53.78 | 0 | — | 0 |
| S1W4 | B35 | Illumina_Miseq | PE250 | 173534 | 250 | 38.11 | 66142 | 54.08 | 0 | — | 0 |
| S2W0 | B58 | Illumina_Miseq | PE250 | 223636 | 250 | 31.94 | 71434 | 55.8 | 0 | — | 0 |
| S2W2 | B59 | Illumina_Miseq | PE250 | 185150 | 250 | 32.01 | 59258 | 55.44 | 0 | — | 0 |
| S2W4 | B60 | Illumina_Miseq | PE250 | 159388 | 250 | 28.23 | 44998 | 55.05 | 0 | — | 0 |
| S2W10 | B61 | Illumina_Miseq | PE250 | 344816 | 250 | 39.19 | 135144 | 52.08 | 0 | — | 0 |
| S3W0 | B71 | Illumina_Miseq | PE250 | 241924 | 250 | 32.86 | 79506 | 55.38 | 0 | — | 0 |
| S3W2 | B72 | Illumina_Miseq | PE250 | 273290 | 250 | 38.59 | 105472 | 55.84 | 0 | — | 0 |
| S3W4 | B73 | Illumina_Miseq | PE250 | 332982 | 250 | 37.47 | 124756 | 53.04 | 0 | — | 0 |
| S4W0 | B81 | Illumina_Miseq | PE250 | 192778 | 250 | 45.56 | 87836 | 53.87 | 0 | — | 0 |
| S4W2 | B98 | Illumina_Miseq | PE250 | 198910 | 250 | 81.35 | 161811 | 53.93 | 0 | — | 0 |
| S4W10 | B100 | Illumina_Miseq | PE250 | 157771 | 250 | 76.87 | 121286 | 51.88 | 0 | — | 0 |
| S5W0 | B107 | Illumina_Miseq | PE250 | 239494 | 250 | 84.11 | 201431 | 55.84 | 0 | — | 0 |
| S5W2 | B108 | Illumina_Miseq | PE250 | 230334 | 250 | 82.31 | 189592 | 55.29 | 0 | — | 0 |
| S5W4 | B109 | Illumina_Miseq | PE250 | 264477 | 250 | 78.33 | 207172 | 52.18 | 0 | — | 0 |
| S5W10 | B110 | Illumina_Miseq | PE250 | 283660 | 250 | 81.24 | 230451 | 52.84 | 0 | — | 0 |
| S5W13 | B111 | Illumina_Miseq | PE250 | 281066 | 250 | 78.64 | 221027 | 55.94 | 0 | — | 0 |
| S5W23 | B112 | Illumina_Miseq | PE250 | 269234 | 250 | 76.53 | 206040 | 52.41 | 0 | — | 0 |
| S6W0 | B14 | Illumina_Miseq | PE250 | 144110 | 250 | 50.6 | 72918 | 54.66 | 0 | — | 0 |
| S6W2 | B15 | Illumina_Miseq | PE250 | 122768 | 250 | 35.01 | 42986 | 55.06 | 0 | — | 0 |
| S6W10 | B17 | Illumina_Miseq | PE250 | 177230 | 250 | 52.6 | 93230 | 53.52 | 0 | — | 0 |
| S7W0' | B24 | Illumina_Miseq | PE250 | 141758 | 250 | 41.43 | 58734 | 54.25 | 0 | — | 0 |
| S7W2 | B25 | Illumina_Miseq | PE250 | 135760 | 250 | 33.35 | 45270 | 55.72 | 0 | — | 0 |

TABLE 5-continued

| sample_name | sample_NUMBER | Sequencing platform | Sequencing_Strategy. PE. SE. | Raw-Reads | Read_length. bp. | Clean_Data. Raw_Data... | Clean_Reads | Read_GC... | Adapter_Rate... | Duplication Rate... | N rate... |
|---|---|---|---|---|---|---|---|---|---|---|---|
| S8W0 | B120 | Illumina_Miseq | PE250 | 225001 | 250 | 77.52 | 174431 | 52.82 | 0 | — | 0 |
| S8W4 | B121 | Illumina_Miseq | PE250 | 231234 | 250 | 78.69 | 181960 | 52.87 | 0 | — | 0 |
| CDI25 | B1 | Illumina_Miseq | PE250 | 93298 | 250 | 29.23 | 27272 | 54.54 | 0 | — | 0 |
| Control12 | B2 | Illumina_Miseq | PE250 | 127534 | 250 | 52.3 | 66694 | 55.41 | 0 | — | 0 |
| CDI26 | B88 | Illumina_Miseq | PE250 | 205071 | 250 | 61.56 | 126248 | 53.34 | 0 | — | 0 |
| Control17 | B37 | Illumina_Miseq | PE250 | 253674 | 250 | 46.68 | 118412 | 51.69 | 0 | — | 0 |
| CDI27 | B48 | Illumina_Miseq | PE250 | 168938 | 250 | 32.75 | 55330 | 54.64 | 0 | — | 0 |
| Control18 | B49 | Illumina_Miseq | PE250 | 356614 | 250 | 48.47 | 172844 | 54.23 | 0 | — | 0 |
| CDI28 | B55 | Illumina_Miseq | PE250 | 144894 | 250 | 27.61 | 39998 | 54.42 | 0 | — | 0 |
| Control19 | B57 | Illumina_Miseq | PE250 | 474850 | 250 | 50.34 | 239062 | 55.47 | 0 | — | 0 |
| CDI29 | B70 | Illumina_Miseq | PE250 | 225218 | 250 | 28.02 | 63114 | 55.92 | 0 | — | 0 |
| CDI30 | B74 | Illumina_Miseq | PE250 | 232140 | 250 | 36.89 | 85644 | 56.9 | 0 | — | 0 |
| Control20 | B75 | Illumina_Miseq | PE250 | 279832 | 250 | 57.13 | 159864 | 54.04 | 0 | — | 0 |
| DI31 | B122 | Illumina_Miseq | PE250 | 241976 | 250 | 82.29 | 199112 | 52.56 | 0 | — | 0 |
| CDI32 | B124 | Illumina_Miseq | PE250 | 166333 | 250 | 81.76 | 135989 | 54.71 | 0 | — | 0 |

REFERENCES

1. Smits, L. P., Bouter, K. E. C., de Vos, W. M., Borody, T. J. & Nieuwdorp, M. Therapeutic Potential of Fecal Microbiota Transplantation. *Gastroenterology* 145, 946-953 (2013).
2. Vrieze, A., et al. Transfer of Intestinal Microbiota From Lean Donors Increases Insulin Sensitivity in Individuals With Metabolic Syndrome. *Gastroenterology* 143, 913-+ (2012).
3. van Nood, E., et al. Duodenal Infusion of Donor Feces for Recurrent *Clostridium difficile*. *New Engl J Med* 368, 407-415 (2013).
4. Lee, C. H., et al. Frozen vs Fresh Fecal Microbiota Transplantation and Clinical Resolution of Diarrhea in Patients With Recurrent *Clostridium difficile* Infection A Randomized Clinical Trial. *Jama-J Am Med Assoc* 315, 142-149 (2016).
5. Drekonja, D., et al. Fecal Microbiota Transplantation for *Clostridium difficile* Infection A Systematic Review. *Ann Intern Med* 162, 630-U230 (2015).
6. Colman, R. J. & Rubin, D. T. Fecal microbiota transplantation as therapy for inflammatory bowel disease: A systematic review and meta-analysis. *Journal of Crohns & Colitis* 8, 1569-1581 (2014).
7 De Leon, L. M., Watson, J. B. & Kelly, C. R. Transient Flare of Ulcerative Colitis After Fecal Microbiota Transplantation for Recurrent *Clostridium difficile* Infection. *Clin Gastroenterol H* 11, 1036-1038 (2013).
8. Kelly, C. R., Kahn, S. A. & Kashyap, P. Update on Fecal Microbiota Transplantation 2015: Indications, Methodologies, Mechanisms, and Outlook (vol 149, pg 223, 2015). *Gastroenterology* 149, 1644-1644 (2015).
9. Khoruts, A. & Sadowsky, M. J. Therapeutic transplantation of the distal gut microbiota. *Mucosal Immunol* 4, 4-7 (2011).
10. Manichanh, C., et al. Reshaping the gut microbiome with bacterial transplantation and antibiotic intake. *Genome Res* 20, 1411-1419 (2010).
11. Rea, M. C., et al. Effect of broad- and narrow-spectrum antimicrobials on *Clostridium difficile* and microbial diversity in a model of the distal colon. *Proceedings of the National Academy of Sciences of the United States of America* 108, 4639-4644 (2011).
12. Li, S. S., et al. Durable coexistence of donor and recipient strains after fecal microbiota transplantation. *Science* 352, 586-589 (2016).
13. Zuo, T., et al. Bacteriophage transfer during faecal microbiota transplantation in *Clostridium difficile* infection is associated with treatment outcome. *Gut*, gutjnl-2017-313952 (2017).
14. Chehoud, C., et al. Transfer of Viral Communities between Human Individuals during Fecal Microbiota Transplantation. *mBio* 7(2016).
15. Broecker, F., et al. Long-term changes of bacterial and viral compositions in the intestine of a recovered *Clostridium difficile* patient after fecal microbiota transplantation. *Molecular Case Studies* 2, a000448 (2016).
16. Limon, J. J., Skalski, J. H. & Underhill, D. M. Commensal Fungi in Health and Disease. *Cell host & microbe* 22, 156-165 (2017).
17. Iliev, I. D. & Leonardi, I. Fungal dysbiosis: immunity and interactions at mucosal barriers. *Nat Rev Immunol* 17, 635-646 (2017).
18. Jiang, T. T., et al. Commensal Fungi Recapitulate the Protective Benefits of Intestinal Bacteria. *Cell host & microbe* 22, 809-816 e804 (2017).
19. Leffler, D. A. & Lamont, J. T. *Clostridium difficile* Infection. *New Engl J Med* 373, 287-288 (2015).

20. Flevari, A., Theodorakopoulou, M., Velegraki, A., Armaganidis, A. & Dimopoulos, G. Treatment of invasive candidiasis in the elderly: a review. *Clin Interv Aging* 8, 1199-1208 (2013).
21. Moyes, D. L., et al. Candidalysin is a fungal peptide toxin critical for mucosal infection. *Nature* 532, 64-+ (2016).
22. Fan, D., et al. Activation of HIF-1 alpha and LL-37 by commensal bacteria inhibits *Candida albicans* colonization. *Nat Med* 21, 808-+(2015).
23. Mason, K. L., et al. Interplay between the Gastric Bacterial Microbiota and *Candida albicans* during Post-antibiotic Recolonization and Gastritis. *Infection and immunity* 80, 150-158 (2012).
24. Dollive, S., et al. Fungi of the Murine Gut: Episodic Variation and Proliferation during Antibiotic Treatment. *PloS one* 8(2013).
25. Downward, J. R. E., Falkowski, N. R., Mason, K. L., Muraglia, R. & Huffnagle, G. B. Modulation of Post-Antibiotic Bacterial Community Reassembly and Host Response by *Candida albicans*. *Sci Rep-Uk* 3(2013).
26. Mason, K. L., et al. *Candida albicans* and Bacterial Microbiota Interactions in the Cecum during Recolonization following Broad-Spectrum Antibiotic Therapy. *Infection and immunity* 80, 3371-3380 (2012).
27. Sokol, H., et al. Fungal microbiota dysbiosis in IBD. *Gut* 66, 1039-1048 (2017).
28. Sartor, R. B. & Wu, G. D. Roles for Intestinal Bacteria, Viruses, and Fungi in Pathogenesis of Inflammatory Bowel Diseases and Therapeutic Approaches. *Gastroenterology* 152, 327-+(2017).
29. Iliev, I. D., et al. Interactions Between Commensal Fungi and the C-Type Lectin Receptor Dectin-1 Influence Colitis. *Science* 336, 1314-1317 (2012).
30. Wheeler, M. L., et al. Immunological Consequences of Intestinal Fungal Dysbiosis. *Cell host & microbe* 19, 865-873 (2016).
31. Gweon, H. S., et al. PIPITS: an automated pipeline for analyses of fungal internal transcribed spacer sequences from the Illumina sequencing platform. *Methods Ecol Evol* 6, 973-980 (2015).
32. Schloss, P. D., et al. Introducing mothur: Open-Source, Platform-Independent, Community-Supported Software for Describing and Comparing Microbial Communities. *Appl Environ Microb* 75, 7537-7541 (2009).
33. McDonald, D., et al. An improved Greengenes taxonomy with explicit ranks for ecological and evolutionary analyses of bacteria and archaea. *Isme J* 6, 610-618 (2012).
34. Chen, X. H., et al. A Mouse Model of *Clostridium difficile*-Associated Disease. *Gastroenterology* 135, 1984-1992 (2008).
35. Liu, C. M., et al. FungiQuant: a broad-coverage fungal quantitative real-time PCR assay. *Bmc Microbiol* 12, 255 (2012).

What is claimed is:

1. A method for treating *Clostridium difficile* infection (CDI) by fecal microbiota transplantation (FMT), comprising the steps of:
   (i) identifying a donor candidate for FMT for treating CDI as a suitable donor upon determining *Candida albicans* level in a stool sample obtained from the candidate as no greater than 0.1% in relative abundance in the stool sample; and
   (ii) performing FMT by administering a composition comprising stool from the suitable donor identified in step (i) to a recipient having CDI to achieve resolution of diarrhea and negative *Clostridium difficile* toxin in the recipient's stool.

2. The method of claim 1, wherein the FMT recipient has inflammatory bowel disease (IBD) with concurrent CDI.

3. The method of claim 1, wherein *C. albicans* level is determined in stool samples taken from the FMT recipient before and after FMT.

4. The method of claim 1, further comprising determining *Saccharomyces* level and *Aspergillus* level in the stool sample.

5. The method of claim 1, further comprising determining *Escherichia* level and *Proteus* level in the stool sample.

6. The method of claim 1, further comprising determining total fungal load in the stool sample.

7. The method of claim 1, wherein *C. albicans* level is determined by quantitative polymerase chain reaction (PCR).

8. The method of claim 1, further comprising determining *C. albicans* level in a stool sample obtained from an FMT recipient prior to FMT.

9. The method of claim 8, wherein the *C. albicans* level is greater than 10% in relative abundance in the FMT recipient stool sample, and wherein the FMT recipient is administered an effective amount of an antifungal agent that suppresses *C. albicans* growth before FMT.

10. The method of claim 9, wherein the *C. albicans* level is determined in a stool sample obtained from the FMT recipient after the antifungal agent is administered and prior to FMT.

11. The method of claim 9, wherein the antifungal agent is fluconazole.

12. The method of claim 1, wherein the FMT recipient is administered an effective amount of an antifungal agent that suppresses *C. albicans* growth before FMT.

13. The method of claim 12, wherein the *C. albicans* level is determined in a stool sample obtained from the FMT recipient after the antifungal agent is administered and prior to FMT.

14. The method of claim 12, wherein the antifungal agent is fluconazole.

15. The method of claim 1, wherein the composition comprises donor stool that has been dried, frozen, and placed in a capsule for oral ingestion.

\* \* \* \* \*